US011607203B2

(12) United States Patent
Kushon et al.

(10) Patent No.: US 11,607,203 B2
(45) Date of Patent: Mar. 21, 2023

(54) FLUID SAMPLING DEVICE

(71) Applicant: NEOTERYX, LLC, Torrance, CA (US)

(72) Inventors: Stuart A. Kushon, Lake Forest, CA (US); Gene Zamba, Valencia, CA (US); Carolyn Jaring, Carson, CA (US); Yibo Guo, Torrance, CA (US); David A Nyberg, II, Frazier Park, CA (US)

( * ) Notice: Subject to any disclaimer, the term of this patent is extended or adjusted under 35 U.S.C. 154(b) by 487 days.

(21) Appl. No.: 15/836,998

(22) Filed: Dec. 11, 2017

(65) Prior Publication Data

US 2018/0161018 A1 Jun. 14, 2018

Related U.S. Application Data

(60) Provisional application No. 62/432,991, filed on Dec. 12, 2016.

(51) Int. Cl.
| | | |
|---|---|---|
| *A61B 5/00* | (2006.01) | |
| *A61B 10/00* | (2006.01) | |
| *A61B 5/15* | (2006.01) | |
| *G01N 1/10* | (2006.01) | |
| *A61B 5/157* | (2006.01) | |
| *G01N 1/02* | (2006.01) | |
| *G01N 1/00* | (2006.01) | |

(52) U.S. Cl.
CPC .......... *A61B 10/0045* (2013.01); *A61B 5/157* (2013.01); *A61B 5/150022* (2013.01); *A61B 5/150251* (2013.01); *A61B 5/150305* (2013.01); *A61B 5/150343* (2013.01); *A61B 5/150358* (2013.01); *G01N 1/10* (2013.01); *A61B 5/15087* (2013.01); *A61B 10/007* (2013.01); *A61B 10/0051* (2013.01); *A61B 2010/0009* (2013.01); *G01N 1/02* (2013.01); *G01N 2001/007* (2013.01); *G01N 2001/028* (2013.01)

(58) Field of Classification Search
CPC .... G01N 33/49; G01N 33/56972; G01N 1/10; G01N 1/02; G01N 2001/007; G01N 2001/028; A61B 5/14532; A61B 5/02438; A61B 10/0045; A61B 5/157; A61B 5/150022; A61B 5/150343; A61B 5/150305; A61B 5/150251; A61B 5/150358; A61B 10/0051; A61B 2010/0009; A61B 10/007; A61B 5/15087
USPC ......... 600/300, 573, 575, 578; 700/213, 214
See application file for complete search history.

(56) References Cited

U.S. PATENT DOCUMENTS 3,718,133 A * 2/1973 Perry ............... A61B 5/150786
600/578
3,930,398 A 1/1976 Levina et al.
(Continued)

FOREIGN PATENT DOCUMENTS

WO WO2016028497 2/2016

OTHER PUBLICATIONS

PCT/US2017/065505 Filed Dec. 11, 2017; WO 2018/111739 A1; Published Jun. 21, 2018 ; and Search Report and Written Opinion dated Apr. 4, 2018.

*Primary Examiner* — May A Abouelela
(74) *Attorney, Agent, or Firm* — Patent Law Agency, LLC; Peter Ganjian

(57) ABSTRACT

An absorbent member, and a recorder that identifies a time and a date of fluid absorbed by the absorbent member.

4 Claims, 76 Drawing Sheets

(56) References Cited

U.S. PATENT DOCUMENTS

| | | | | |
|---|---|---|---|---|
| 3,993,452 | A * | 11/1976 | Moulding | B01L 3/5453 346/80 |
| 7,252,642 | B2 * | 8/2007 | Kislev | B01L 3/502 422/82.05 |
| 8,924,005 | B2 | 12/2014 | Kern | |
| 2008/0031774 | A1 * | 2/2008 | Magnant | G01N 35/00722 422/63 |
| 2010/0129789 | A1 * | 5/2010 | Self | B01L 9/06 435/5 |
| 2011/0196218 | A1 * | 8/2011 | Nomura | G01N 33/48792 600/365 |
| 2012/0123233 | A1 * | 5/2012 | Cohen | A61B 10/007 600/345 |
| 2013/0116597 | A1 * | 5/2013 | Rudge | A61B 5/150305 600/575 |
| 2013/0123696 | A1 | 5/2013 | Kern | |
| 2013/0158482 | A1 * | 6/2013 | Davis | A61M 37/0015 604/173 |
| 2013/0164781 | A1 * | 6/2013 | Lefebvre | G01N 1/312 435/40.52 |
| 2014/0038306 | A1 | 2/2014 | Berthier et al. | |
| 2014/0066726 | A1 * | 3/2014 | Costello | A61B 5/073 600/302 |
| 2014/0073990 | A1 * | 3/2014 | Holmes | A61B 5/15113 600/575 |
| 2014/0320807 | A1 * | 10/2014 | Thangaraju | A61B 5/14532 351/206 |
| 2014/0323911 | A1 * | 10/2014 | Sloan | A61B 5/150343 600/573 |
| 2014/0336083 | A1 | 11/2014 | Khattak et al. | |
| 2015/0164398 | A1 * | 6/2015 | Ko | A61B 10/0045 600/573 |
| 2015/0216471 | A1 * | 8/2015 | Goldstein | A61B 5/4848 600/373 |
| 2015/0346212 | A1 * | 12/2015 | Mor | A61F 13/505 435/287.2 |
| 2015/0351728 | A1 * | 12/2015 | Stewart | A61B 10/0096 600/573 |
| 2016/0038068 | A1 * | 2/2016 | Chickering, III | A61B 5/15186 600/583 |
| 2016/0069847 | A1 | 3/2016 | Stripp | |
| 2016/0303558 | A1 | 10/2016 | Lehane et al. | |
| 2017/0122846 | A1 * | 5/2017 | Holmes | G01N 33/491 |
| 2017/0265789 | A1 | 9/2017 | Naseri et al. | |
| 2019/0343438 | A1 * | 11/2019 | Gibson | A61B 5/150022 |

\* cited by examiner

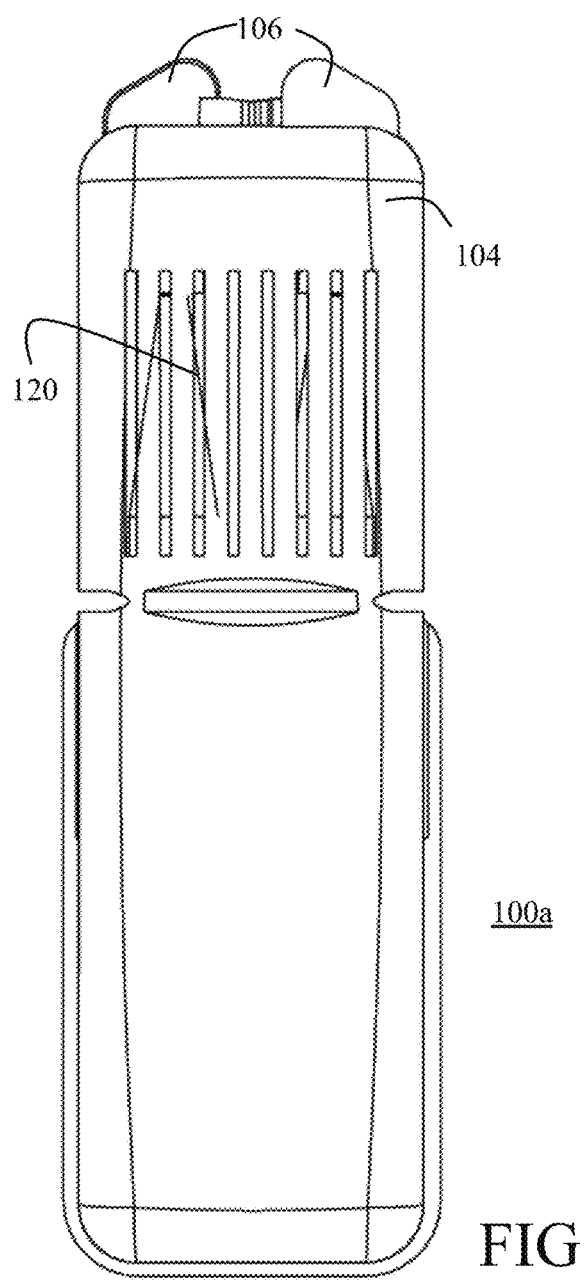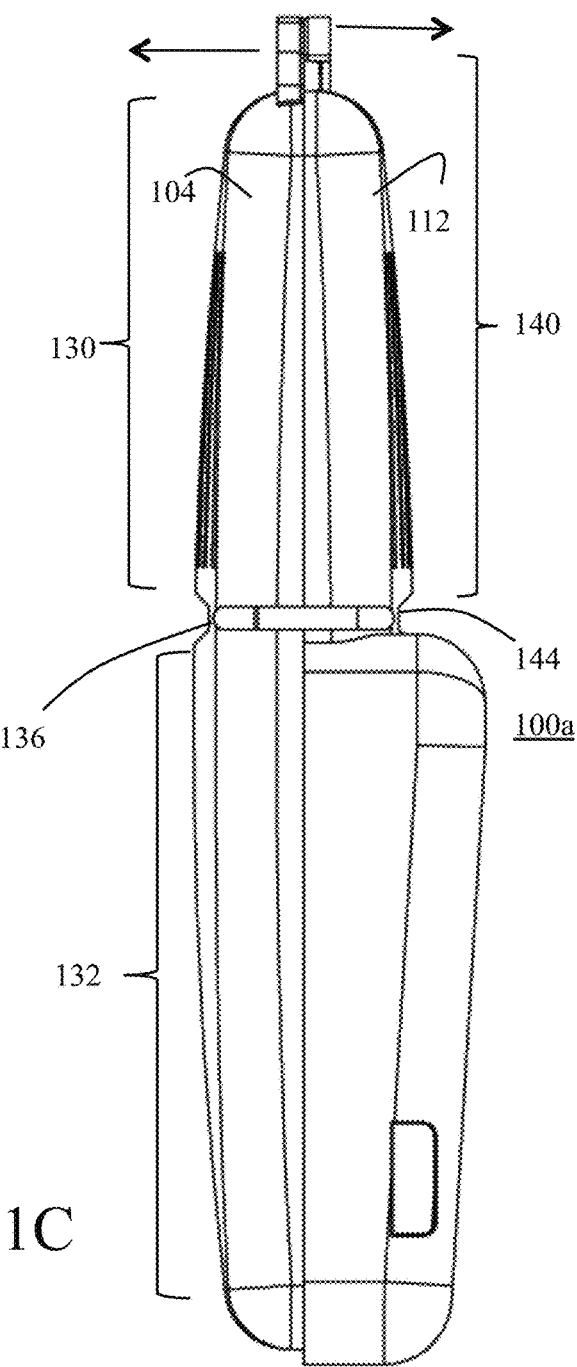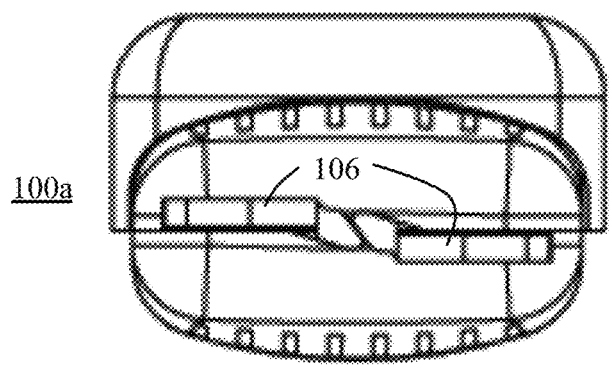
FIG. 1C
FIG. 1D
FIG. 1E

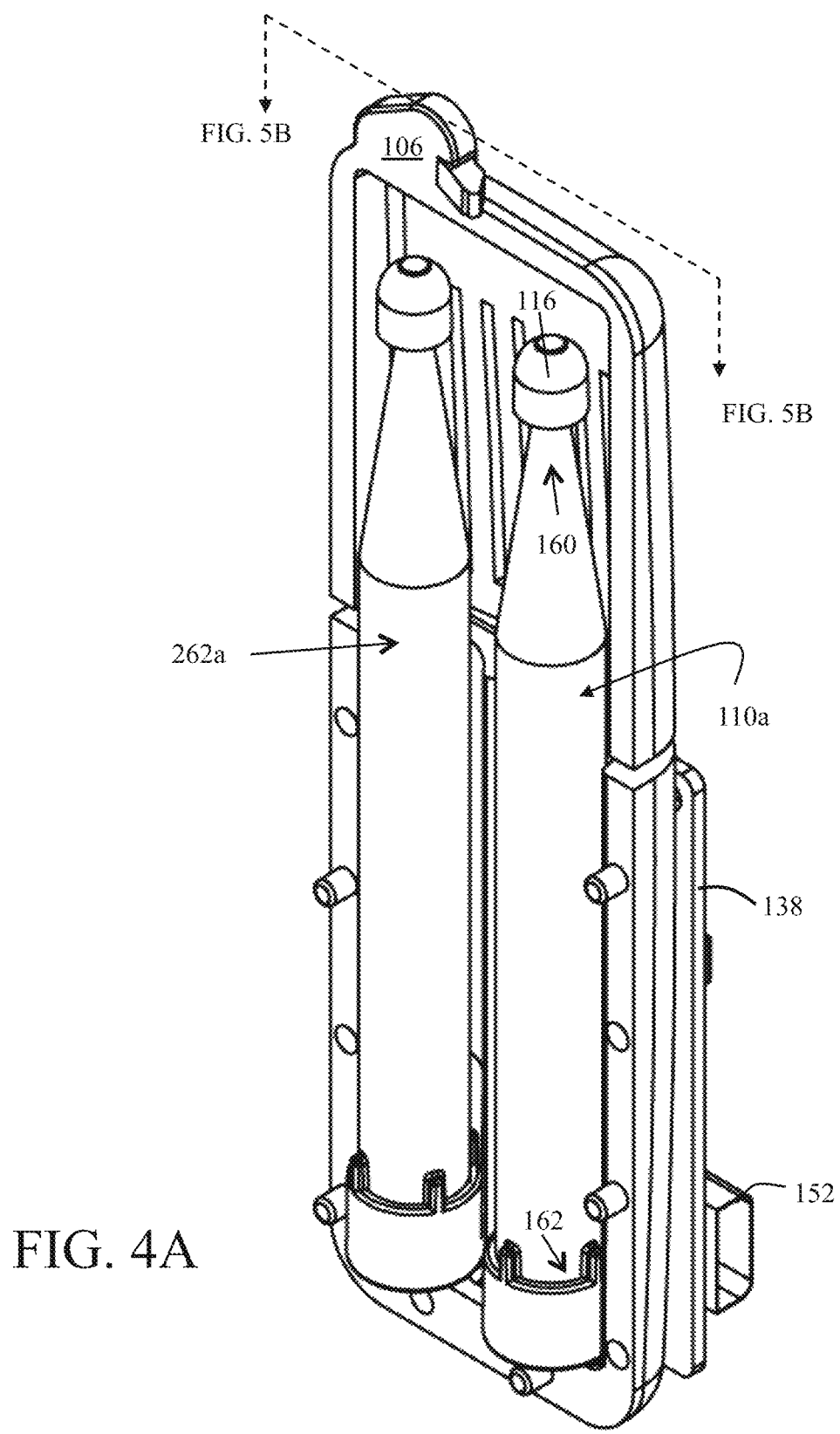

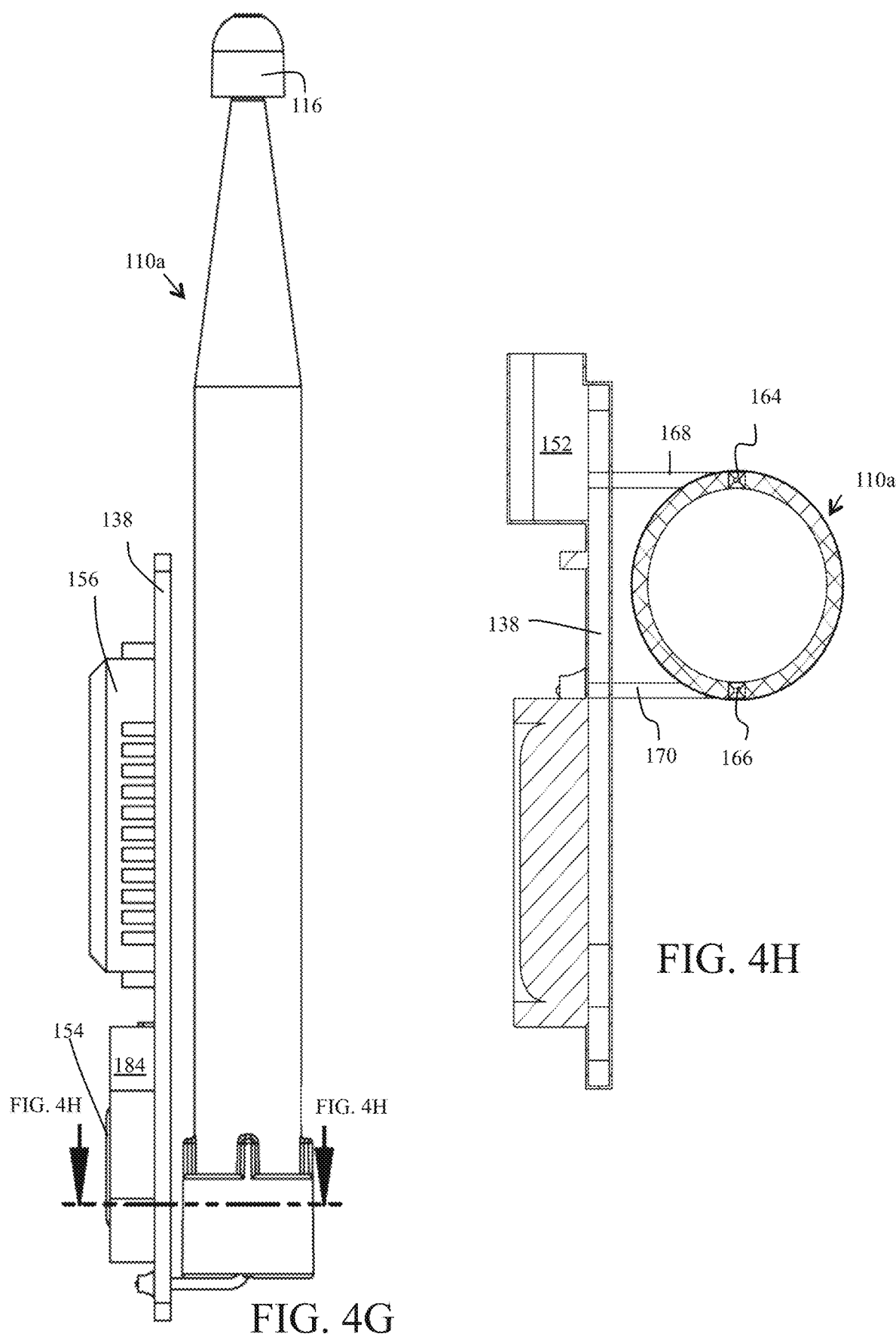

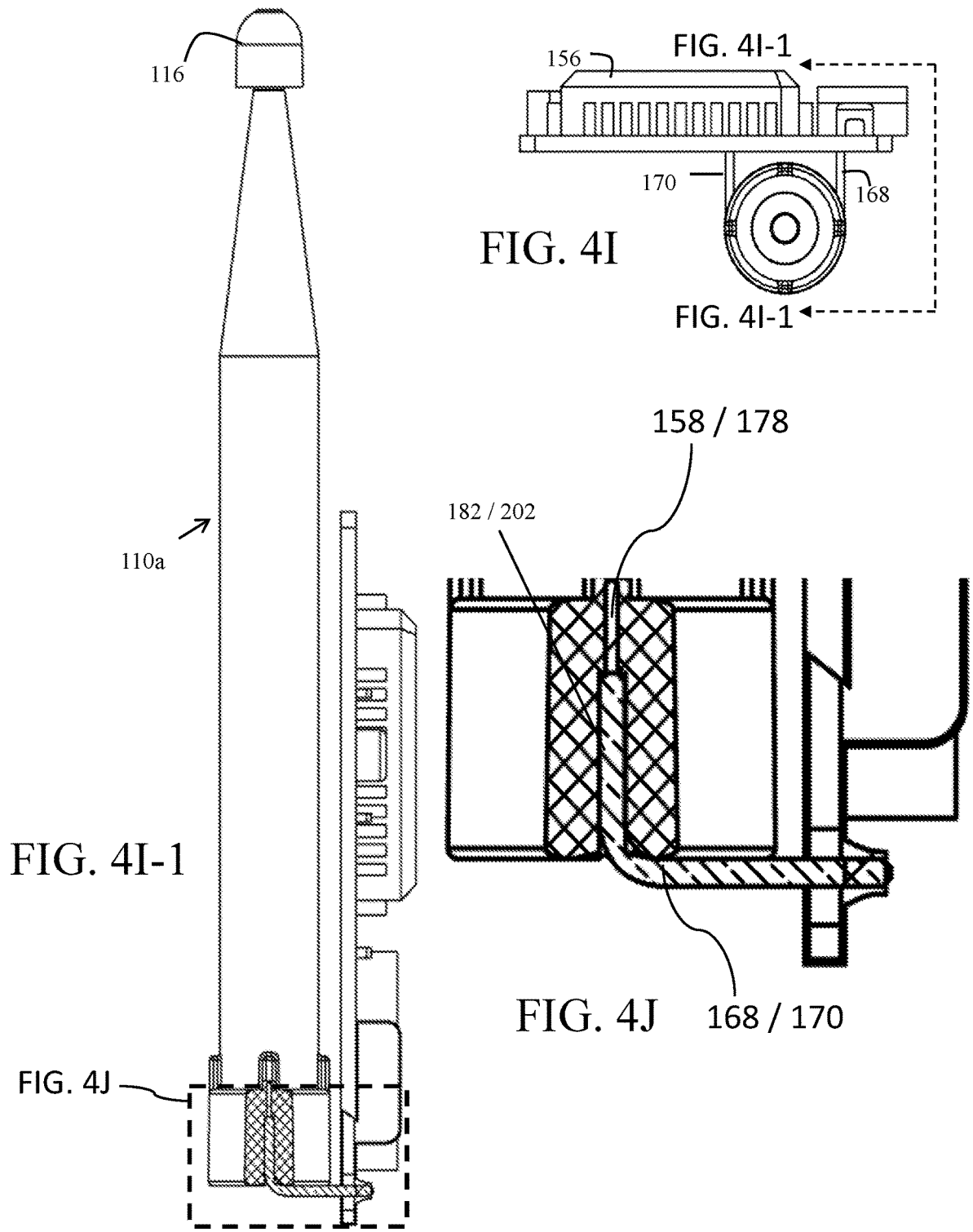

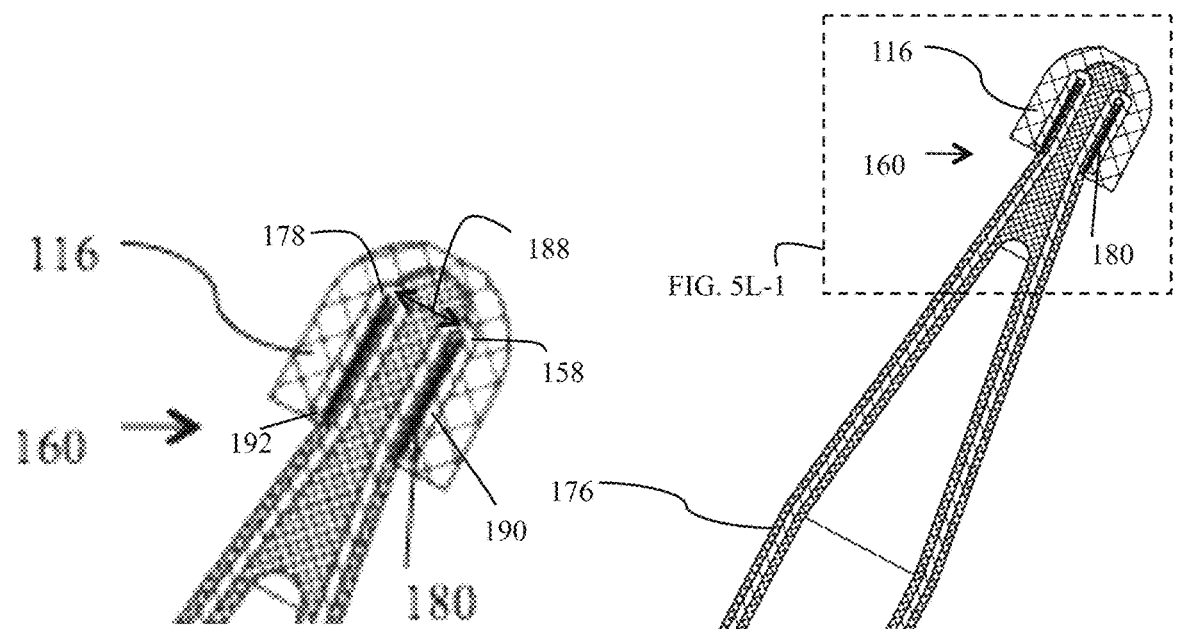
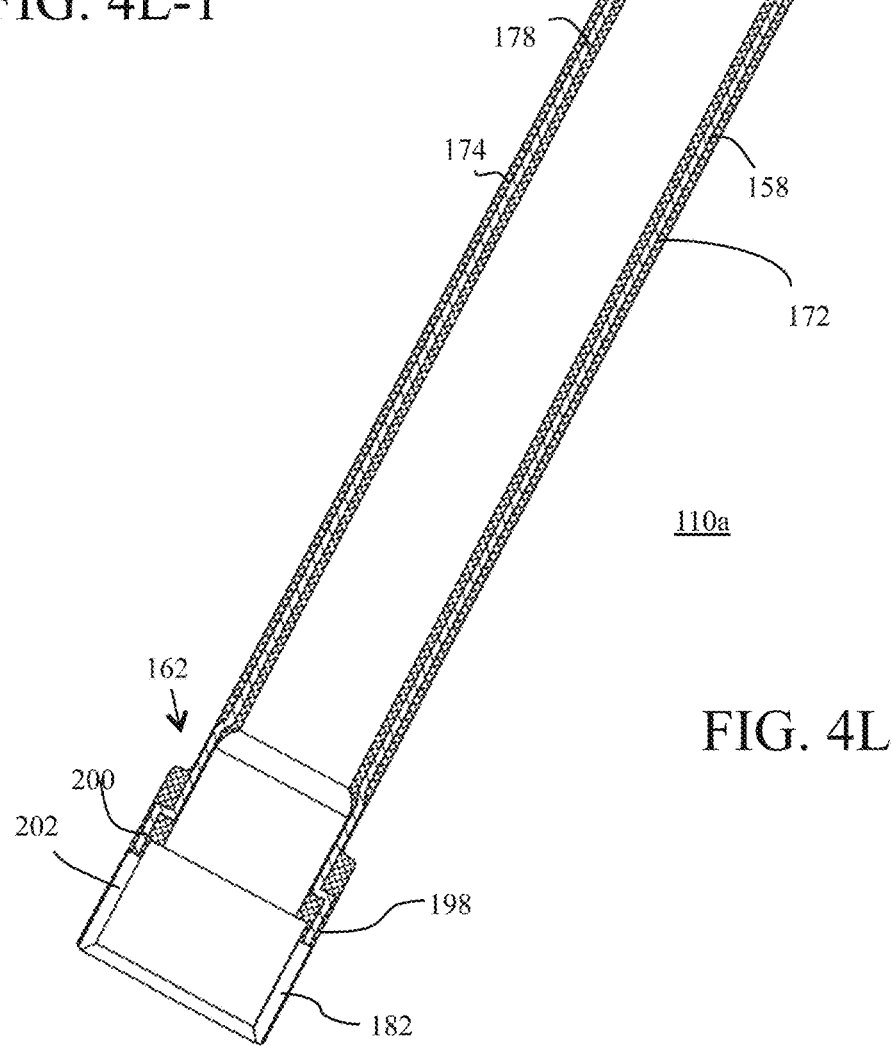
FIG. 4L-1
FIG. 4L

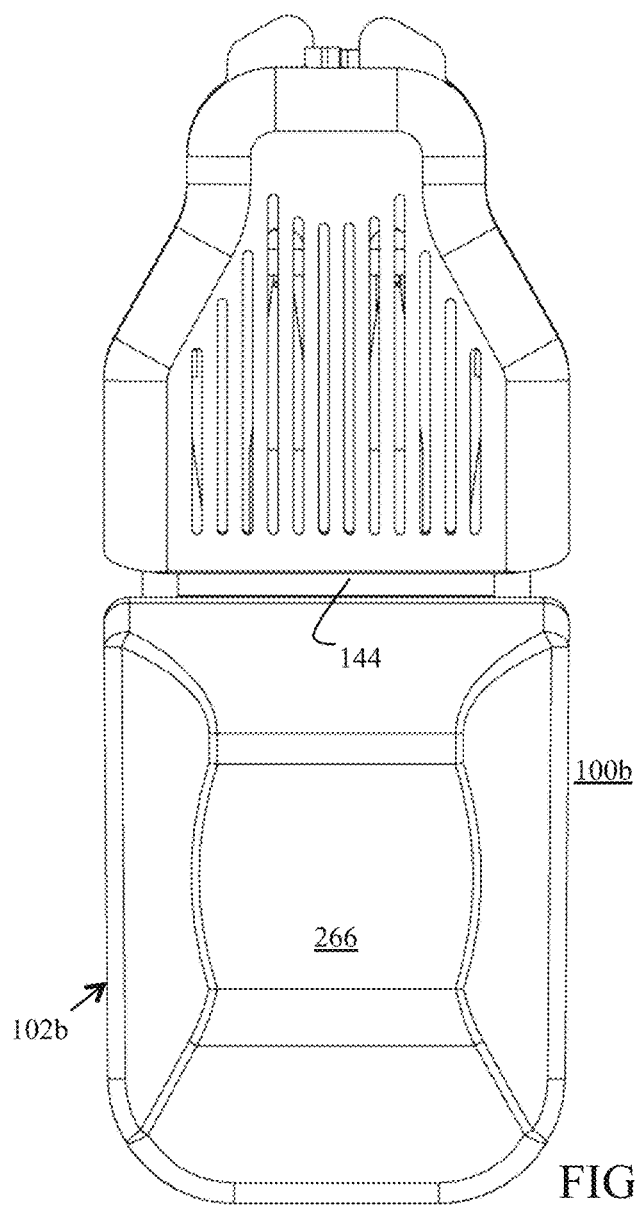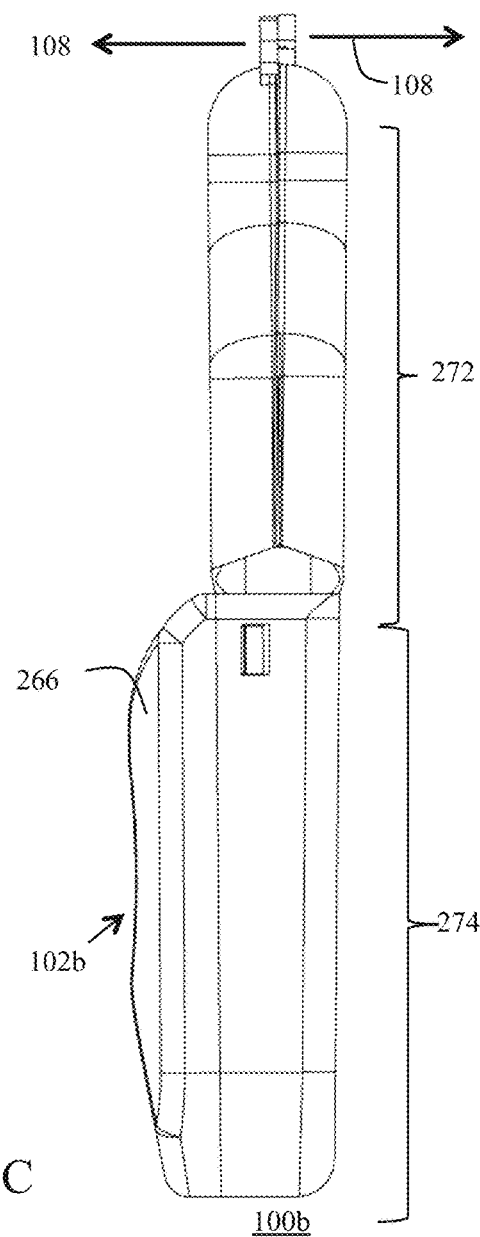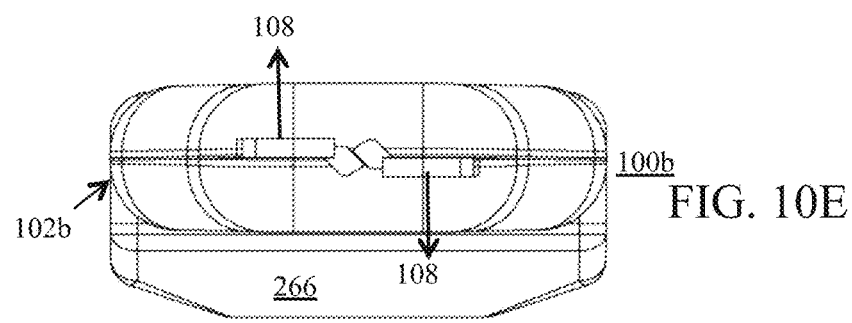
FIG. 10C
FIG. 10D
FIG. 10E

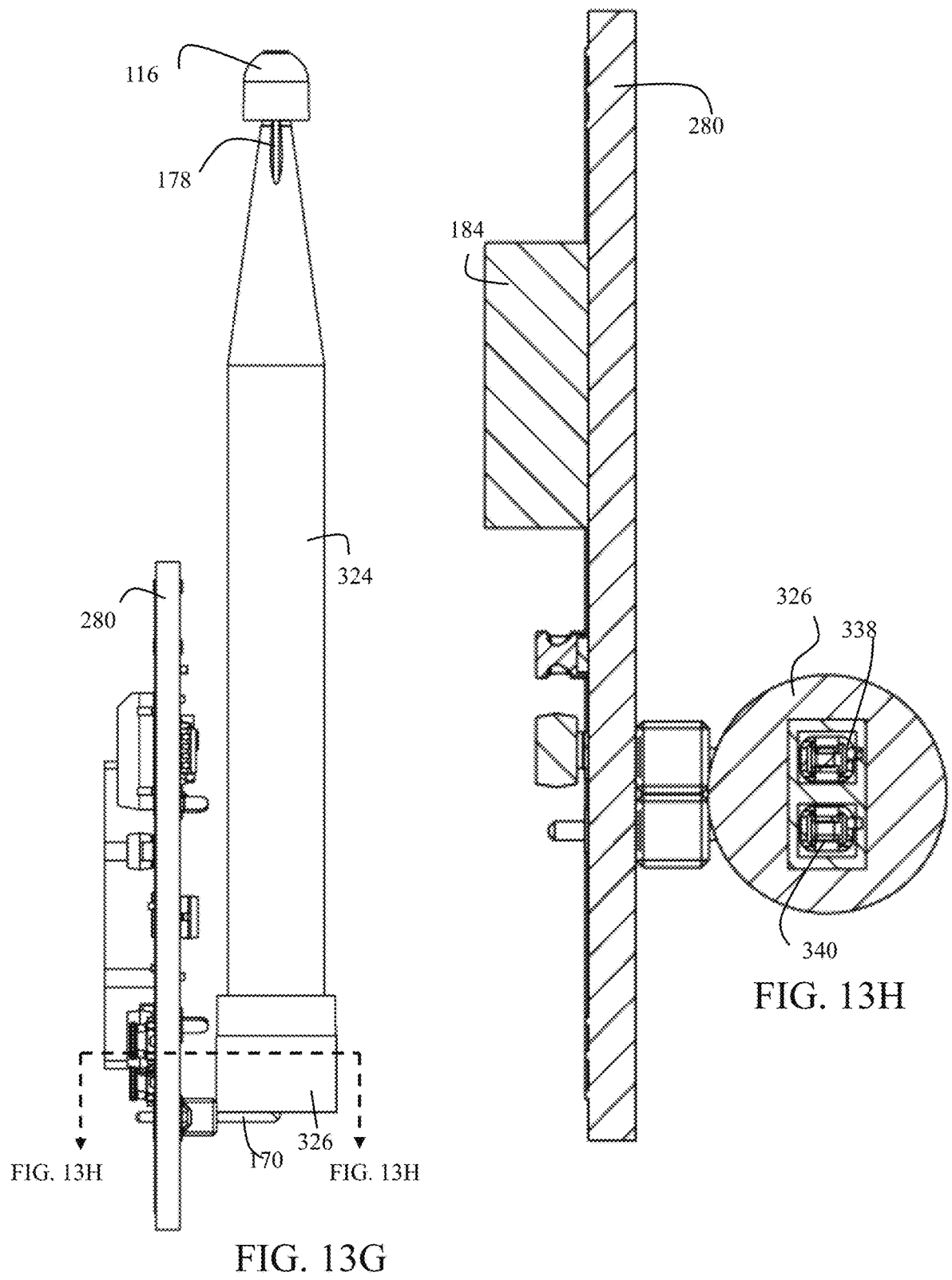

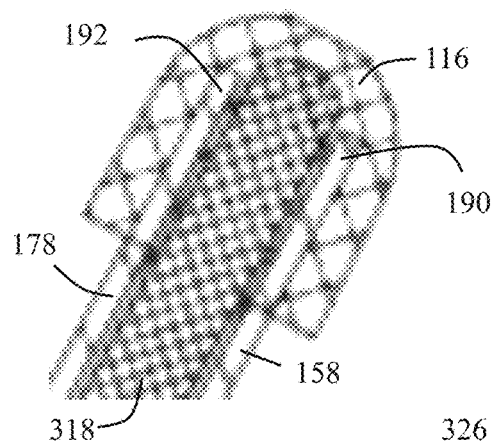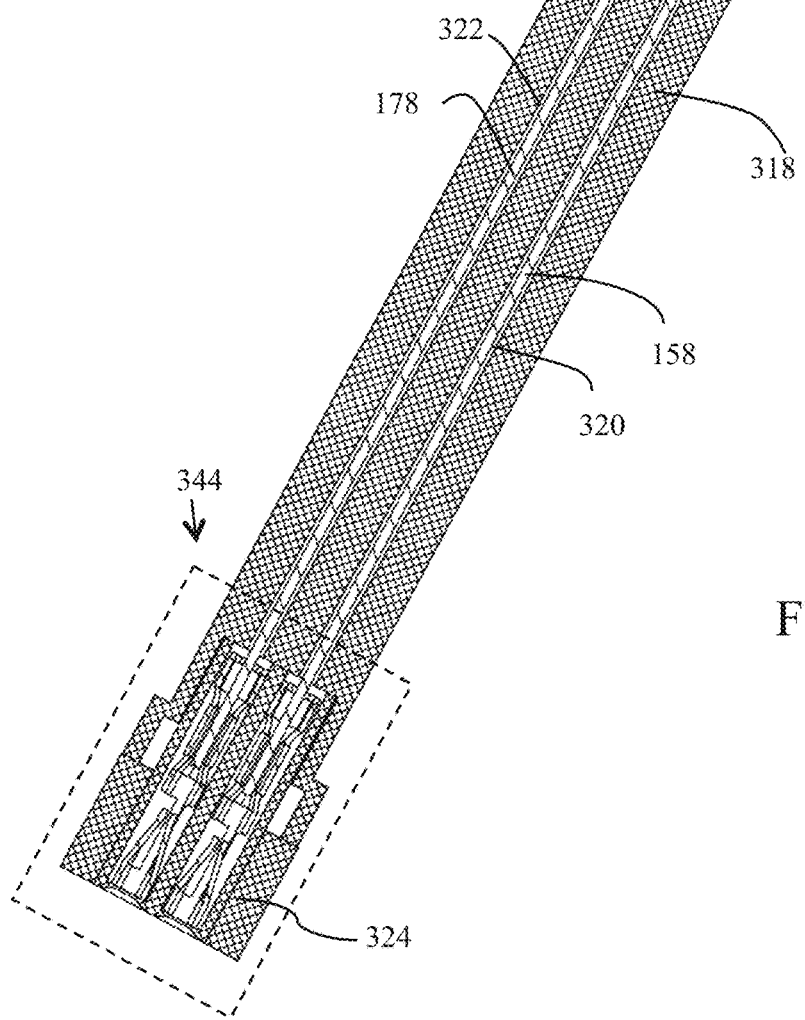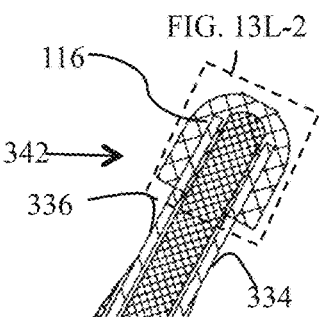
FIG. 13L-2
FIG. 13L-1

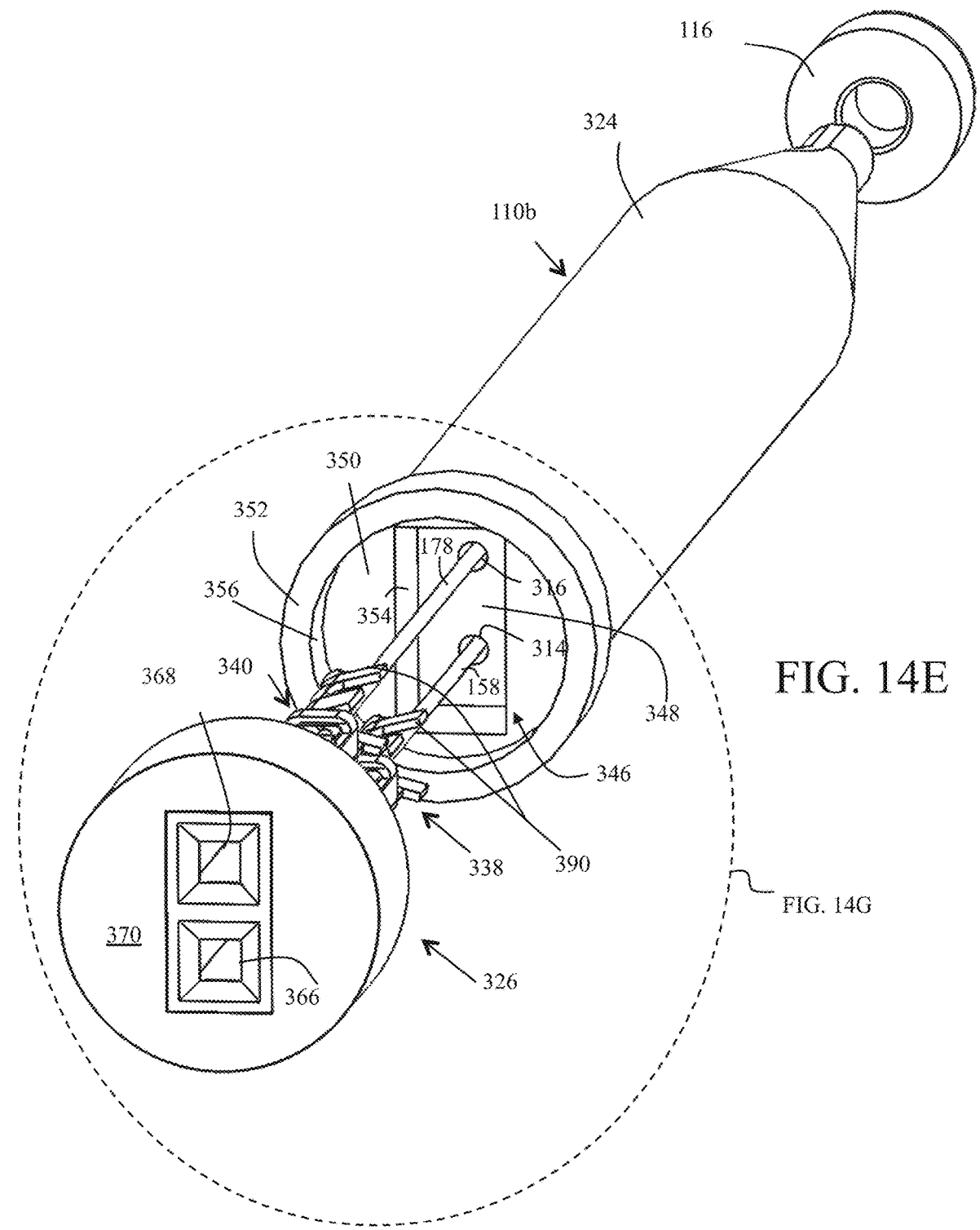

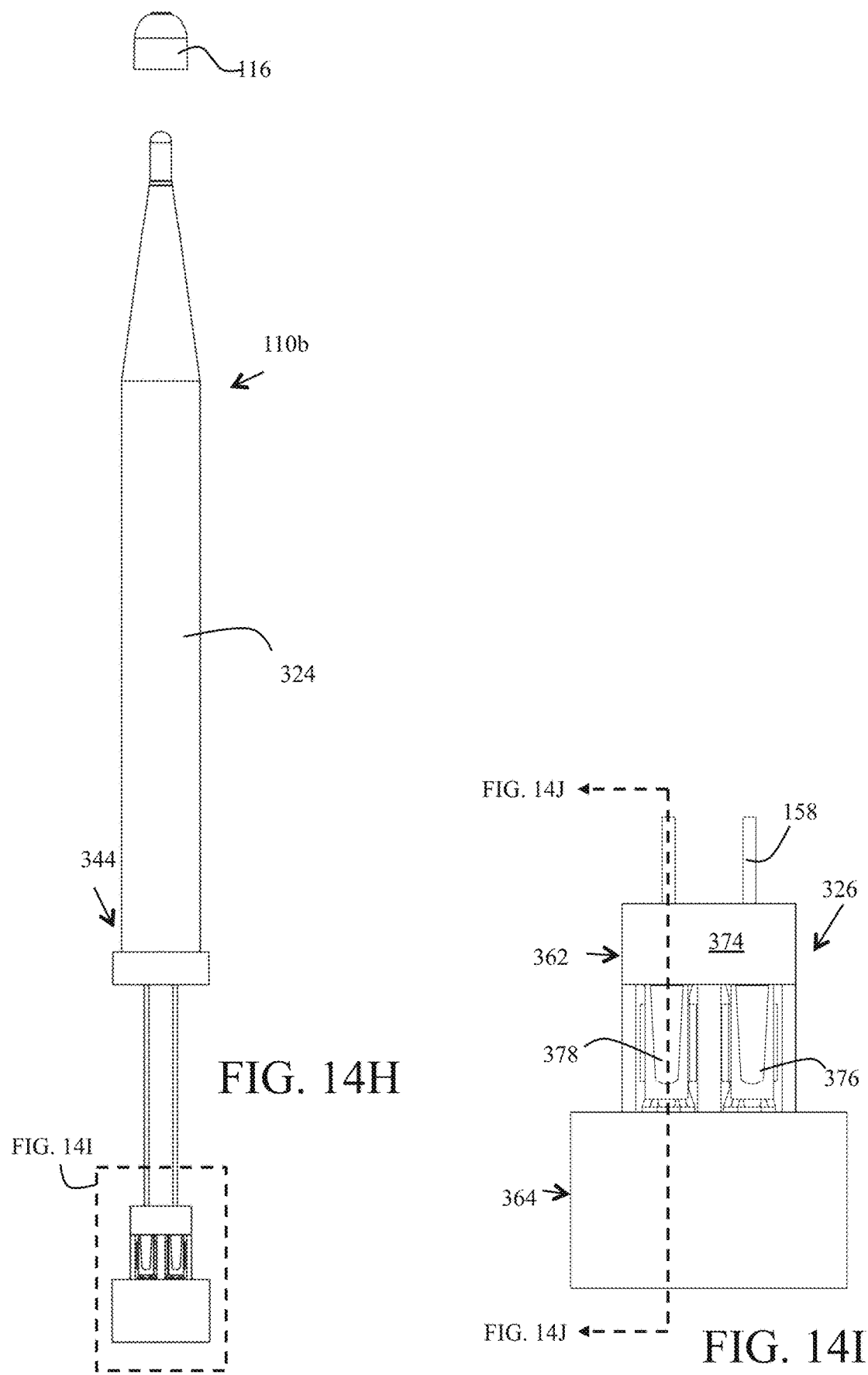

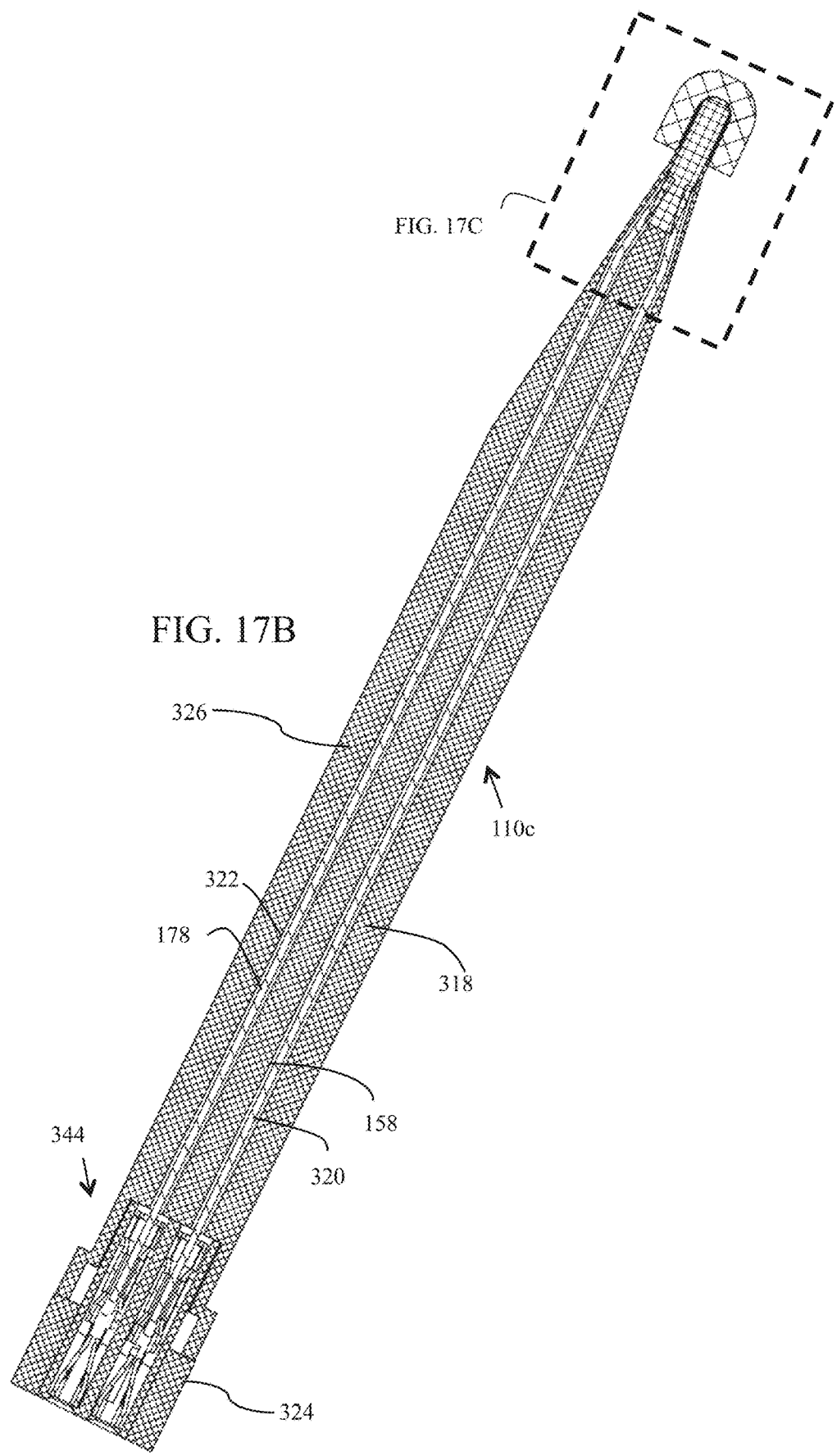

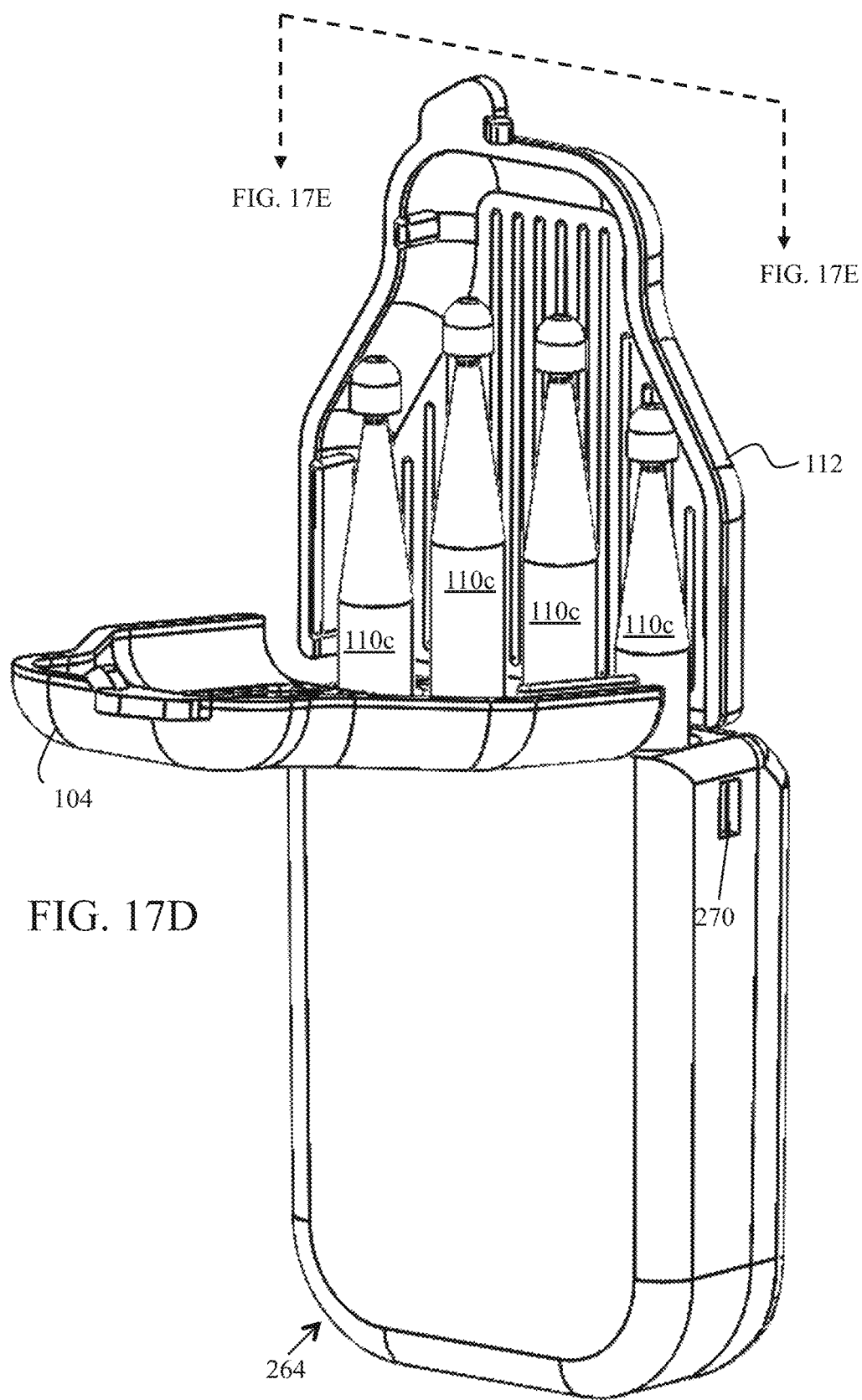

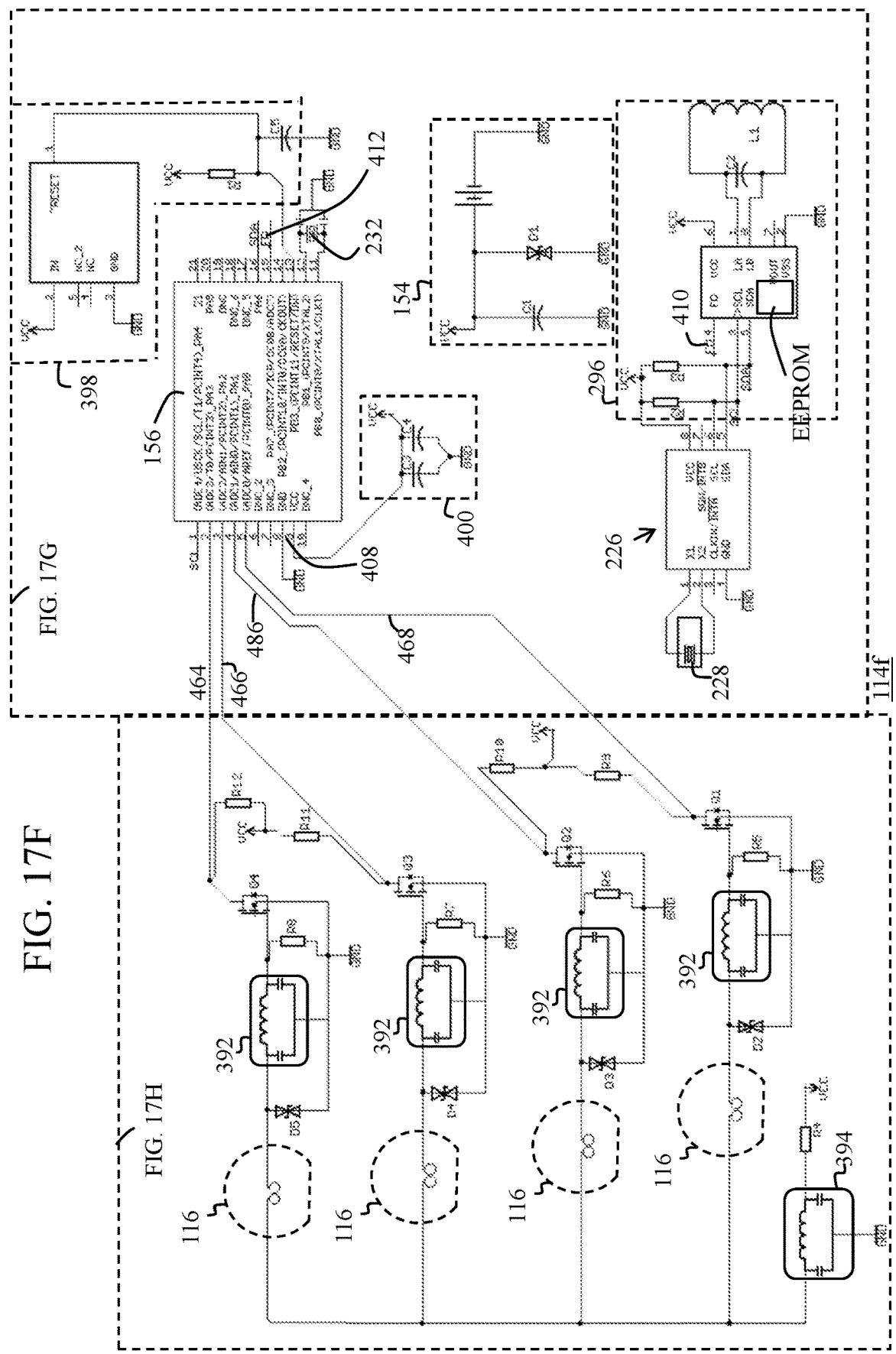

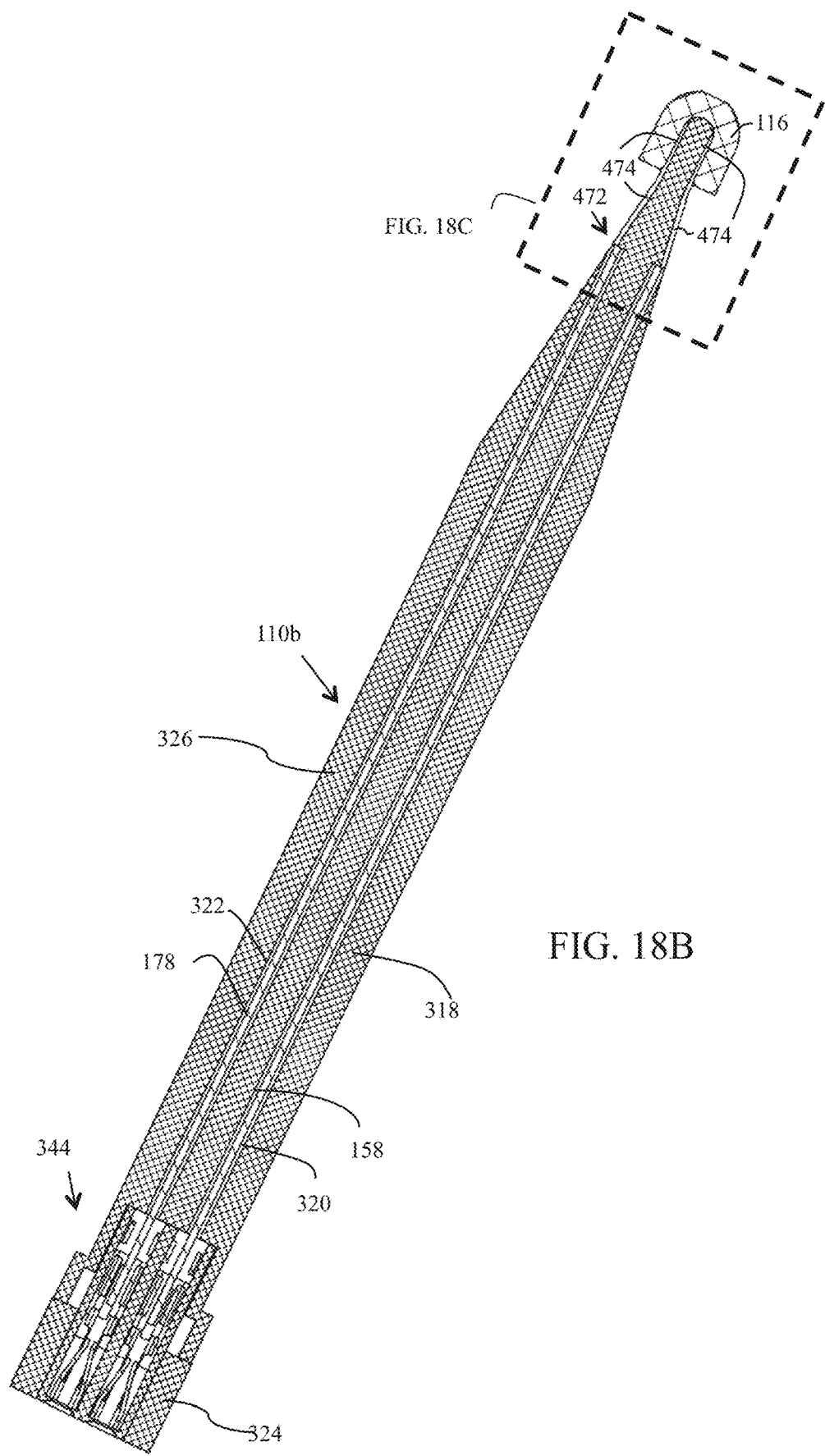

FLUID SAMPLING DEVICE

CROSS-REFERENCE TO RELATED APPLICATIONS

This Application claims the benefit of priority of U.S. Utility Provisional Patent Application 62/432,991, filed 12 Dec. 2016, the entire disclosure of which is expressly incorporated by reference in its entirety herein.

All documents mentioned in this specification are herein incorporated by reference to the same extent as if each individual document was specifically and individually indicated to be incorporated by reference.

It should be noted that throughout the disclosure, where a definition or use of a term in any incorporated document(s) is inconsistent or contrary to the definition of that term provided herein, the definition of that term provided herein applies and the definition of that term in the incorporated document(s) does not apply.

BACKGROUND OF THE INVENTION

Field of the Invention

One or more embodiments of the present invention relate to fluid sampling devices and, more particularly, to a fluid sampling device that provides timestamp data associated with sampled fluid.

Description of Related Art

Conventional methods to acquire fluid samples for pharmacokinetics analyses have no mechanism to determine the actual time and date at which points samples are acquired. Determining accurate sampling time point of a sample is important because there are time sensitive fluid components that may kinetically change when in the process of absorbing or rapidly excreting a drug. Accordingly, inaccurate recording of time and date at which point a sample is taken may completely change the pharmacokinetic analysis.

Accordingly, in light of the current state of the art and the drawbacks to current sampling schemes and methods, a need exists for a fluid sampling device that provides timestamp data associated with actual time and date of sample acquisition.

BRIEF SUMMARY OF THE INVENTION

A non-limiting, exemplary aspect of an embodiment of the present invention provides a fluid sampling device, comprising:
an absorbent member; and
a recorder that is triggered to generate data when fluid is absorbed by the absorbent member;
the data includes time and date of sample acquisition.

Another non-limiting, exemplary aspect of an embodiment of the present invention provides a fluid sampling device, comprising:
an absorbent member; and a recorder that identifies a time and a date of fluid absorbed by absorbent member.

Yet another non-limiting, exemplary aspect of an embodiment of the present invention provides a fluid sampling device, comprising:
an absorbent member; and
a recorder associated with the absorbent member;
wherein: the recorder is triggered to generate data in relation to fluid absorbed by the absorbent member; the generated data includes timestamp data that identifies time and date fluid was absorbed by the absorbent member.

A further non-limiting, exemplary aspect of an embodiment of the present invention provides a fluid sampling device, comprising:
a cartridge that includes:
one or more absorbent members;
a recorder associated with at least one absorbent member.

Still a further non-limiting, exemplary aspect of an embodiment of the present invention provides a fluid sampling device, comprising:
a cartridge that includes:
a handler probe with an absorbent member; and
a recorder associated with the absorbent member of the handler probe;
the recorder generating and recording timestamp data when sufficient fluid is absorbed by the absorbent member.

Another non-limiting, exemplary aspect of an embodiment of the present invention provides a fluid sampling device, comprising:
a handler probe with an absorbent member;
a pair of electrodes that are associated with the handler probe and a recorder device; and
an active mode signal generator that outputs an active mode signal when the pair of electrodes are bridged by fluid;
the recorder device includes:
a microcontroller unit (MCU) that is driven from a non-active mode to an active mode by the active mode signal;
a Real Time Clock that outputs a timestamp information when instructed by the MCU;
the timestamp information is stored in a non-volatile memory, and output by an output device.

Yet another non-limiting, exemplary aspect of an embodiment of the present invention provides a fluid sampling device, comprising:
a handler probe comprised of a main and a connector-receptacle piece that friction-fits within a bottom cavity of main;
the main includes:
a body with a solid interior that includes a first and a second orifice within which reside respective a first and a second electrode;
the first and the second electrodes extending from top lateral openings of the main, with a first distal ends of the first and the second electrode capped by an absorbent member at top of the main;
the electrodes extending from bottom openings of the main, with second distal ends of the first and the second electrode coupled with the connector-receptacle piece;
the connector-receptacle piece includes:
the connector-receptacle piece a first and second through-openings that house respective first and second female crimper-connectors.

These and other features and aspects of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" may be used to mean "serving as an example, instance, or illustration," but the absence of the term "exemplary" does not denote a limiting embodiment. Any embodiment described as "exemplary" is not necessarily to be construed as preferred or advantageous over other embodiments. In the drawings, like reference character(s) present corresponding part(s) throughout.

FIGS. 9A to 9B-2 are non-limiting, exemplary electrical schematic illustrations and flowchart diagram of a recorder and MCU operations with an external Real Time Clock (RTC) and an external non-volatile memory, including use of different types of communications portals in accordance with another embodiment of the present invention;

FIGS. 17A to 17I are non-limiting, exemplary illustrations of a fluid sampling device in accordance with another embodiment of the present invention; and FIGS. 18A to 18C are non-limiting, exemplary illustrations of a handler probe in accordance with another embodiment of the present invention.

DETAILED DESCRIPTION OF THE INVENTION

Figure 1A:
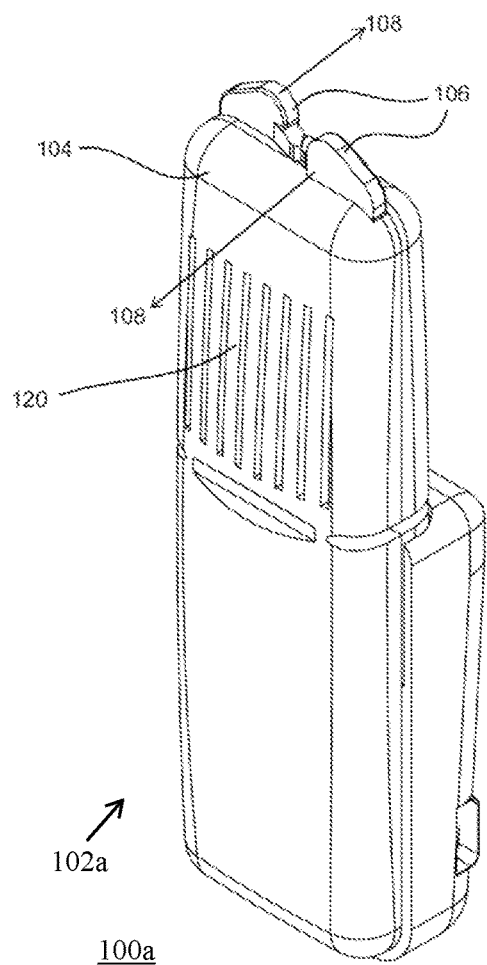
FIGS. 1A to 6C are non-limiting, exemplary illustrations of a fluid sampling device in accordance with one or more embodiments of the present invention.
Figure 1B:
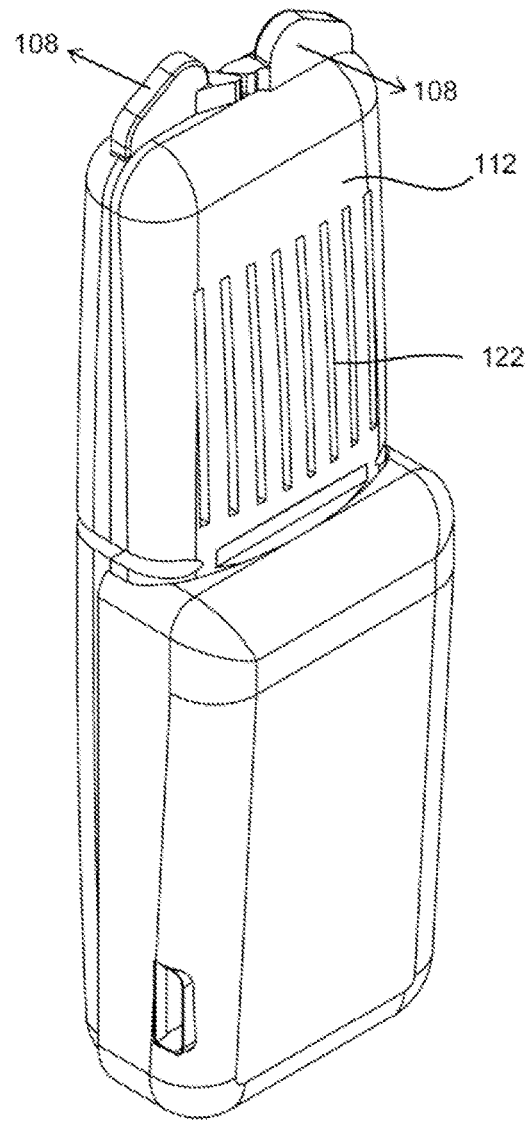

The detailed description set forth below in connection with the appended drawings is intended as a description of presently preferred embodiments of the invention and is not intended to represent the only forms in which the present invention may be constructed and or utilized.

It is to be appreciated that certain features of the invention, which are, for clarity, described in the context of separate embodiments, may also be provided in combination in a single embodiment. Conversely, various features of the invention that are, for brevity, described in the context of a single embodiment may also be provided separately or in any suitable sub-combination or as suitable in any other described embodiment of the invention. Stated otherwise, although the invention is described below in terms of various exemplary embodiments and implementations, it should be understood that the various features and aspects described in one or more of the individual embodiments are not limited in their applicability to the particular embodiment with which they are described, but instead can be applied, alone or in various combinations, to one or more of the other embodiments of the invention.

For purposes of illustration, programs and other executable program components are illustrated herein as discrete blocks, although it is recognized that such programs and components may reside at various times in different storage components, and are executed by the data processor(s) of the computers. Further, each block within a flowchart (if a flowchart is used) may represent both method function(s), operation(s), or act(s) and one or more elements for performing the method function(s), operation(s), or act(s). In addition, depending upon the implementation, the corresponding one or more elements may be configured in hardware, software, firmware, or combinations thereof.

In the description given below and or the corresponding set of drawing figures, when it is necessary to distinguish the various members, elements, sections/portions, components, parts, or any other aspects (functional or otherwise) or features or concepts or operations of a device(s) or method(s) from each other, the description and or the corresponding drawing figures may follow reference numbers with a small alphabet character such as (for example) "fluid sampling device 100a, 100b, and etc." If the description is common to all of the various members, elements, sections/portions, components, parts, or any other aspects (functional or otherwise) or features or concepts or operations of a device(s) or method(s) such as (for example) to all fluid sampling devices 100a, 100b, etc., then they may simply be referred to with reference number only and with no alphabet character such as (for example) "fluid sampling device 100."

The present invention defines timestamp as data that amongst others identifies when a certain event occurred. It should be noted that timestamp in accordance with one or more embodiments of the present invention is not just the time at which an event is recorded, but also the time of the event itself.

Throughout the disclosure, references to timestamp are meant as illustrative, for convenience of example, and for discussion purposes only. That is, the present invention is not limited to only providing timestamp data in relation to time and date record or data but may also be used (without much modifications, if any) for other data related to other information in the context within which the present invention is used. For example, in a clinical setting, patient information may also accompany "timestamp data."

One or more embodiments of the present invention provide a fluid sampling device with time-stamping capability that ensures that a sampled fluid is associated with actual time and date of sample acquisition.

As detailed below, one or more embodiments of the present invention provide a fluid sampling device 100, comprising an absorbent member 116 and a recorder 114 associated with the absorbent member 116. Recorder 114 is automatically activated or triggered to generate data in relation to fluid 118 absorbed by absorbent member 116, with the generated data including (amongst others) timestamp data that identifies when (actual time and date) fluid 118 was absorbed by absorbent member 116.

FIGS. 1A to 1E are non-limiting, exemplary illustrations of a fluid sampling device in a non-limiting, exemplary form-factor of a cartridge that is illustrated in the closed position in accordance with one or more embodiments of the present invention. FIGS. 2A to 2D are non-limiting, exemplary illustrations of the fluid sampling device shown in FIGS. 1A to 1E, but with the cartridge illustrated in the open position in accordance with one or more embodiments of the present invention. FIGS. 2A to 2D also progressively illustrate a non-limiting, exemplary method of use of the fluid sampling device in accordance with one or more embodiments of the present invention.

As illustrated in FIGS. 1A to 2D, fluid sampling device 100a is packaged within a cartridge 102a that includes a pair of covers or lids 104 and 112 with a pair of tabs 106 that when maneuvered (pulled away from each other) in the direction shown by arrows 108 open and allows access (FIGS. 2A to 2D) to a pair of handler probes 110a and 262a in cartridge 102a. As best illustrated in FIGS. 2A to 2D, cartridge 102a houses the pair of handler probes 110a and 262a, one or both of which may be associated with a recorder device 114a, which may record (amongst others) timestamp data when activated (detailed below). As detailed below, it should be noted that the number of handler probes need not be limited to only one or two, but may be more than the two illustrated.

Figure 2A:
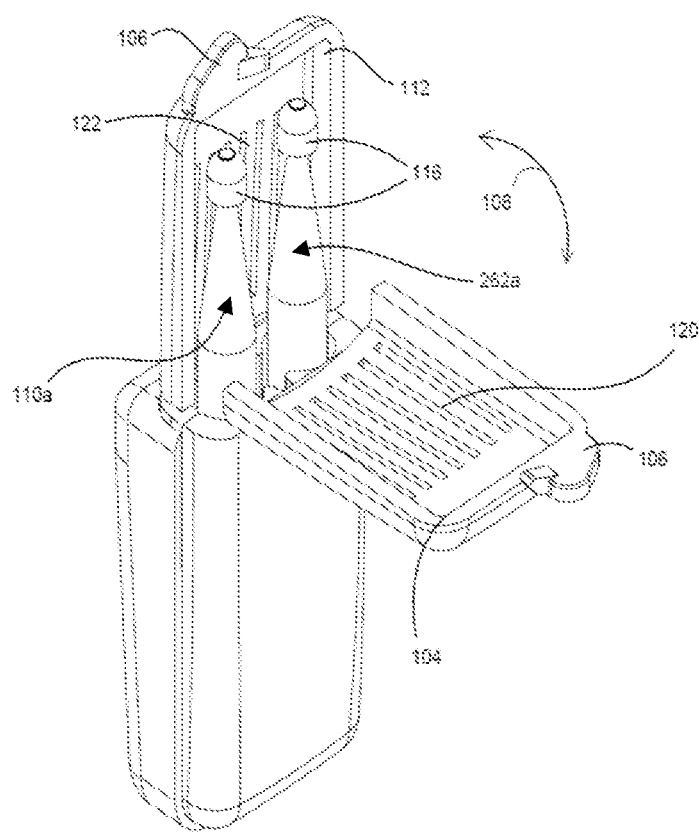
Figure 2B:
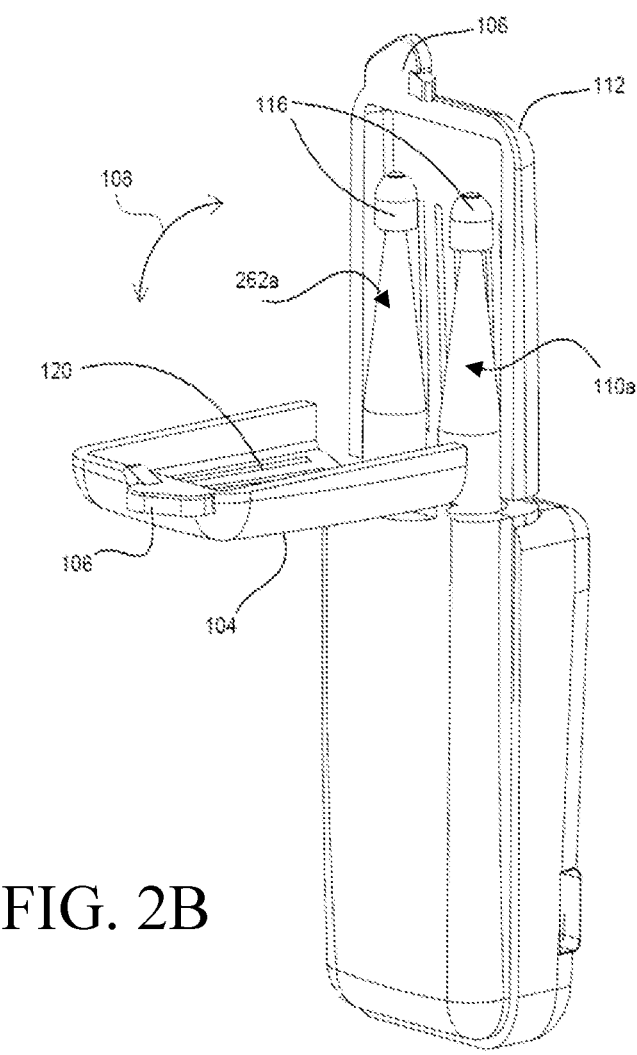
Figure 2C:
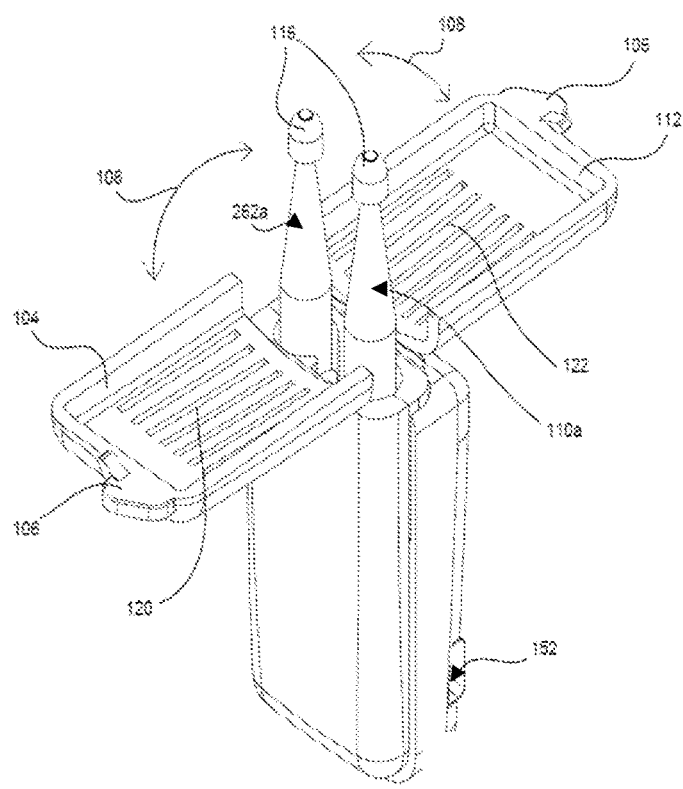
Figure 2D:
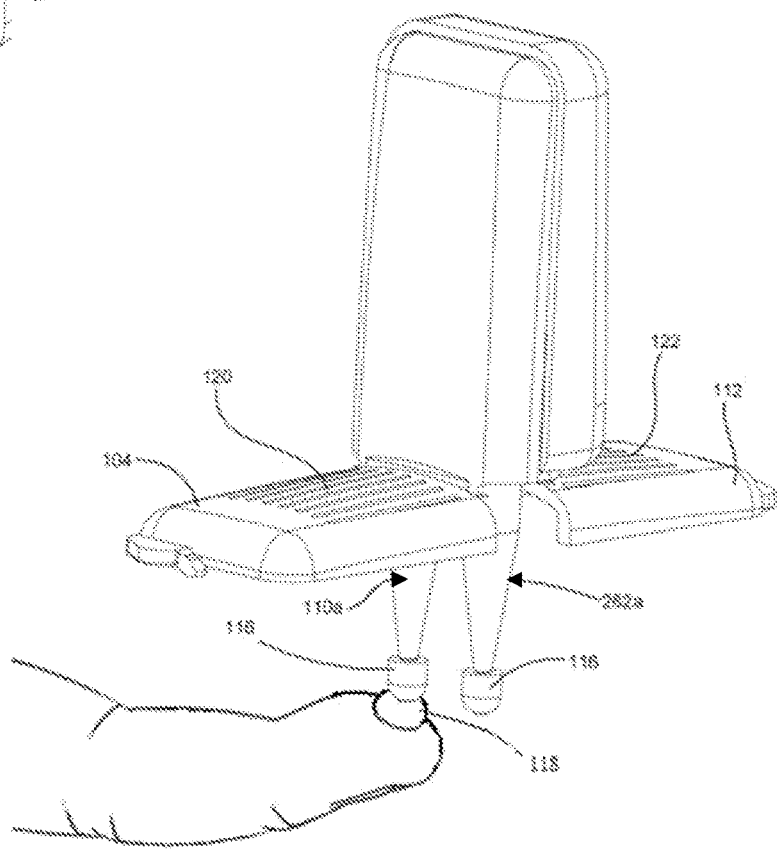

As best illustrated in FIG. 2D, users simply dip an absorbent member 116 of both handler probes 110a and 262a into a fluid sample source 118 (for example, from cut of finger) to sample fluid. As detailed below, sufficient absorption of fluid 118 by absorbent member 116 for handler probe 110a that is connected to recorder 114 automatically and immediately triggers recorder device 114 housed within cartridge 102a to generate an actual time and date of sample acquisition (e.g., time at 13:05:22 with date 4 July 2016). Thereafter, users may simply close off the covers 104 (tabs 106 snapping back into closed latched position shown in FIGS. 1A to 1E), enabling fluid loaded absorbent members 116 of both handler probes 110a and 262a to dry via vent openings 120 and 122 of covers 104 and 112. The entire cartridge 102a may then be sent to a lab for assay, including extraction of recorded data (including data related to timestamp information—detailed below).

Non-limiting, non-exhaustive listing of examples of materials for absorbent member 116 may comprise of pores plastic, ceramic, carbon, etc. so long as the absorbent members 116 are highly hydrophilic or chemically changed to become hydrophilic. Non-limiting, non-exhaustive listing of examples of absorbent members 116 that may be used within one or more embodiments of the present invention as absorbent members 116 may include those that are disclosed in U.S. Patent Application Publication 2013/0116597 to Rudge et al., U.S. Patent Application Publication 2017/0043346 to Emmet Welch, U.S., U.S. Patent Application Publication 2017/0023446 to Gijbertus G. Rietveld, the entire disclosures of all of which are expressly incorporated by reference in their entirety herein.

It should be noted that handler probes 110a and 262a are adapted to be operated by well known automated instruments for fluid sample analysis and hence, need not be handled or operated by individuals for assay. The external structure or external construct of handler probes 110a and 262a are detailed in U.S. Patent Application Publication 2013/0116597 to Rudge et al., U.S. Patent Application Publication 2017/0043346 to Emmet Welch, U.S., U.S. Patent Application Publication 2017/0023446 to Gijbertus G. Rietveld, the entire disclosures of all of which are expressly incorporated by reference in their entirety herein. However, the internal construct or internal structure of handler probe 110a in accordance with one or more embodiments of the present invention are disclosed in detail in FIGS. 4A to 4N-1, with handler probe 262a identical to those disclosed in the above referenced publications.

It should further be noted that it is preferred to have two or more handler probes 110a and 262a with absorbent members 116, which would enable collection of multiple samples within a very close time frame for multiple assays. This would enable application of multiple tests on the collected samples and provide for validation of data integrity. For example, it is a conventional laboratory practice to use two or more collected fluid samples for the same type of assay for validation and data integrity. Alternatively, each collected fluid sample may be used for different types of assays without having to ask patient for more samples. Extra samples may also be stored for later use. Accordingly, handler probe 110a that is connected to recorder 114a may be of a different color, instructing or indicating to a patient to first use that handler probe 110a, which would allow for recordation of date and time of collection of sample and immediately thereafter, use the other handler probe 262a. This way, two or more samples may be collected from the same fluid source approximately within a few seconds of each other where the timestamp data from the first (i.e., connected) handler probe 110a would still be correctly applicable to the other handler probe 262a.

As further detailed below, it should further be noted that since electrodes 158 and 178 (FIG. 4B) and are comprised of metal and physically, directly contact absorbent member 116 (best shown in FIG. 4L-1), potential does exists for leaching of material from electrodes 158 and 178 and onto absorbent member 116, mixed with collected fluid sample. Leaching from electrodes 158 and 178 may therefore obviously contaminate the collected fluid sample. Therefore, it would be preferable if absorbent member 116 of handler probe 110a contacting electrodes 158 and 178 is only used for generating timestamp information rather than for assay. The other absorbent members 116 of the other handler probes 262a that do not have any electrodes may be used for assay in any well-known conventional manner.

Figure 3A:
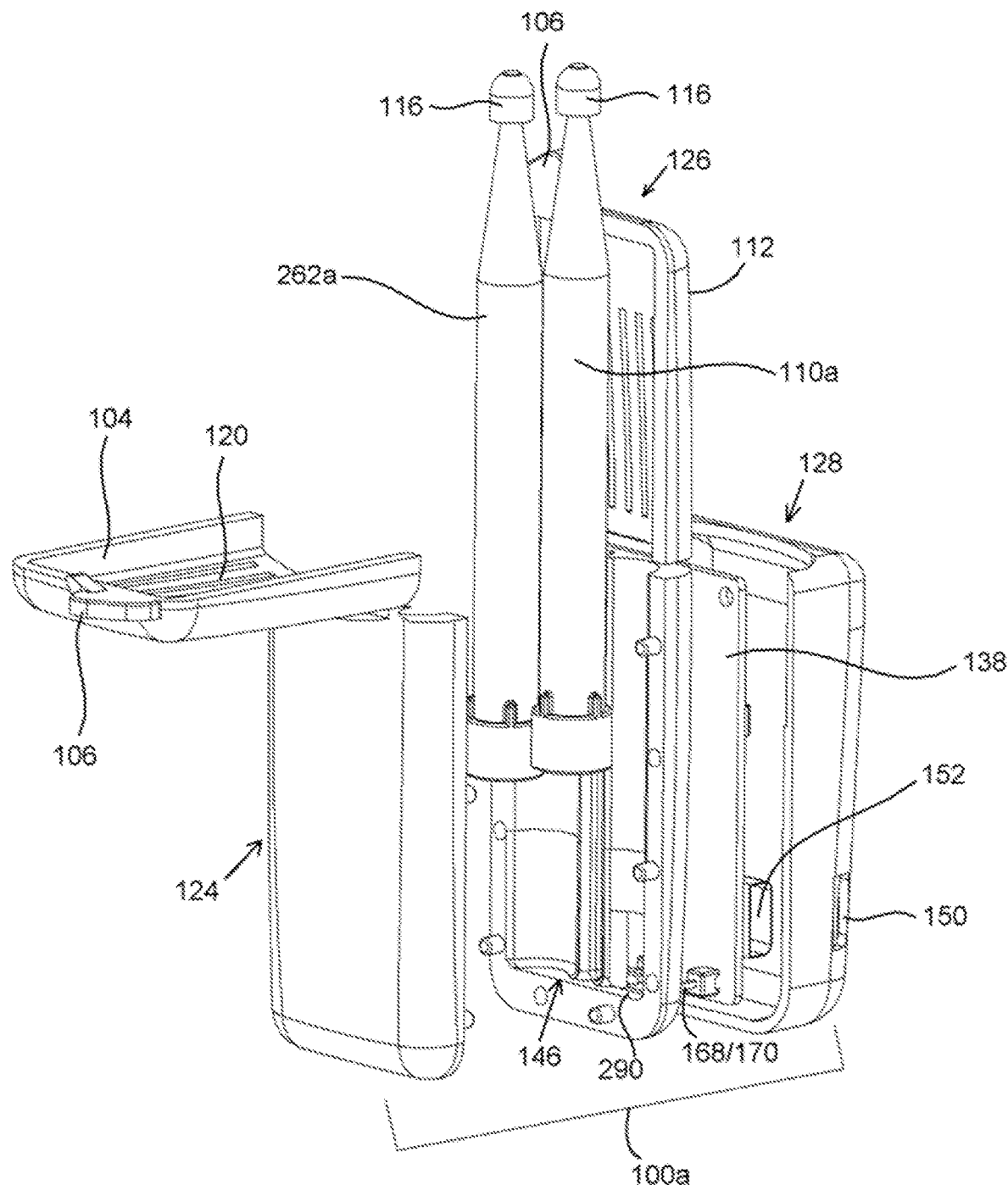
Figure 3B:
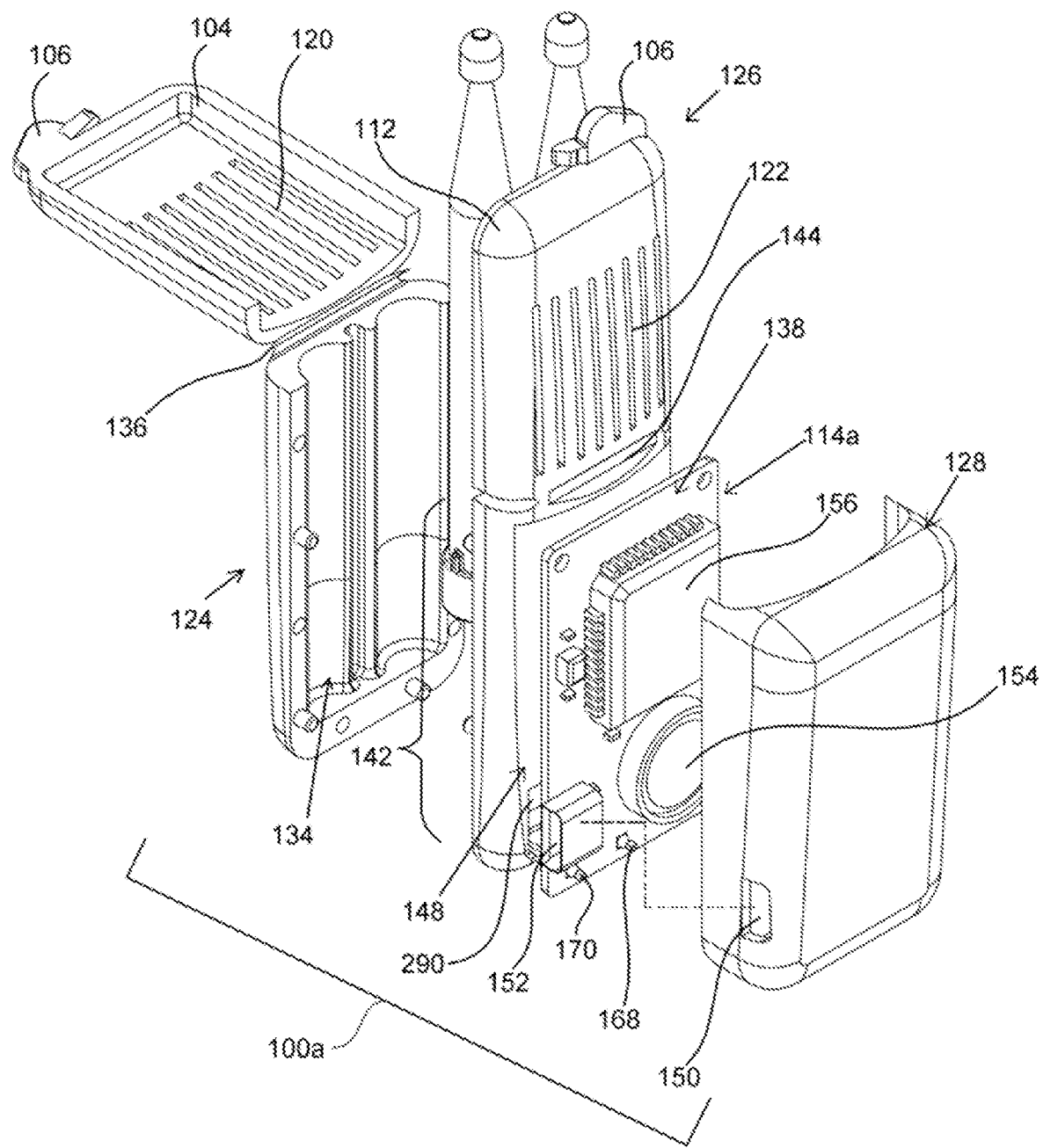

FIGS. 3A and 3B are non-limiting exemplary exploded view illustrations of the cartridge shown in FIGS. 1A to 2D in accordance with one or more embodiments of the present invention. The exploded views shown in FIGS. 3A and 3B illustrate disassembled, separated pieces of cartridge 102a that show the cooperative working relationship, orientation, positioning, and exemplary manner of assembly of the pieces in accordance with one or more embodiments of the present invention.

As illustrated in FIGS. 3A and 3B, cartridge 102a of fluid sampling device 100a is comprised of a first lateral piece 124, a center piece 126, and a second lateral piece 128. All pieces may be connected together by a variety of well known methods non-limiting examples of which may include well-known "snap" connections with projections from one piece being snapped into corresponding engagement or interlocking recesses in another, by ultrasonic welding, or other well known methods, etc.

First lateral piece 124 includes a first upper portion 130 (FIG. 1D) that comprises first cover 104 and a first lower portion 132 that houses handler probes 110a. Interior side 134 (FIG. 3B) of lower portion 132 of first lateral piece 124 of cartridge 102a is configured to securely accommodate handler probes 110a and 262a. As illustrated, first cover 104 is associated with first lower portion 132 by a living hinge 136, with cover 104 including vent opening 120 to allow for ventilation, which facilitates drying of fluid loaded absorbent members 116.

Center piece 126 of cartridge 102a of fluid sampling device 100a also accommodates handler probes 110a and 262a in addition to electronics (one or more Printed Circuit Board—PCBs) 138 of recorder device 114a required for recording of data related to sampled fluid. Center piece 126 of cartridge 102a includes a second upper portion 140 (FIG. 1D) that comprises a second cover 112 associated with second lower portion 142 (FIG. 3B) of cartridge by living hinge 144, with second lower portion 142 housing handler probes 110a, 262a, and electronics (Printed Circuit Board-PCB) 138. As illustrated, second cover 112 also includes vent openings 122 to allow for ventilation, which facilitates drying of fluid loaded absorbent members 116.

First side 146 (FIG. 3A) of second lower portion 142 of center piece 126 of cartridge 102a is configured to securely accommodate handler probes 110a, 262a and includes an opening 290 that enables access to PCB 138 (and hence, a second side 148). Opening 290 allows pins 168 and 170 to extend from PCB 138, passed second side 148 and extend out of first side 146 to connect with handler probe 110a. Second side 148 (FIG. 3B) of second lower portion 142 of center piece 126 of cartridge 102a accommodates the PCB 138, which may be mounted and secured thereon in any well known conventional method such as by use of adhesives, rivets, or other fasteners and the like.

In this non-limiting, exemplary instance, second lateral piece 128 of cartridge 102a includes one or more opening 150 for accessing various portals 152 of PCB 138 such as a Universal Serial Bus (USB) connector. Second lateral piece 128 of cartridge 102a also functions to cover over PCB 138.

As well be detailed below, recorder device 114a (the electronics of which may be fully mounted onto one or more PCBs 138) may comprise of a main power source 154 that powers recorder device 114a, including a Microcontroller Unit (MCU) 156. In this non-limiting exemplary instance, recorder device 114a includes a well known exemplary portal 152 in a form of a Universal Serial Bus (USB) that may be used to extract data and or charge the power source 154. In this non-limiting exemplary instance, the MCU 156 may comprise of DS87C530 manufactured by MAXIM DALLAS SEMICONDUCTORS or, alternatively, ATtiny814V and ATtnny817 by ATMEL. In general, MCU 156 used may include built-in Electrically Erasable Programmable Read Only Memory (EEPROM) and Real Time Clock (RTC).

As well be apparent below, one or more handler probes 110a may include conductive electrodes 158 and 178 that may be electrically and mechanically connected to recorder device 114a. In this non-limiting exemplary instance, only one absorbent member 116 of handler probe 110a is electrically connected to recorder device 114 via electrodes 158 and 178.

Figure 4B:
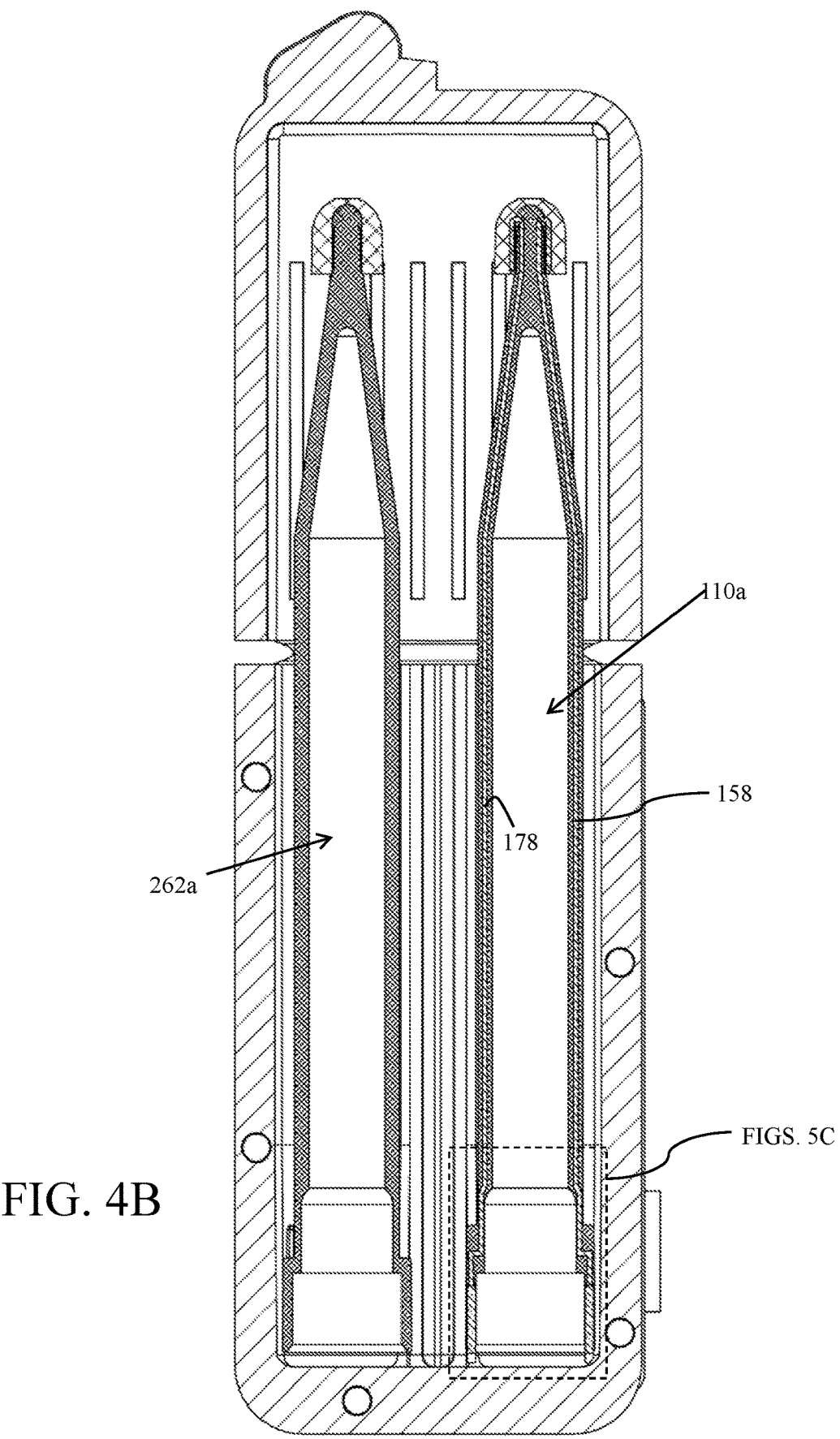
Figure 4C:
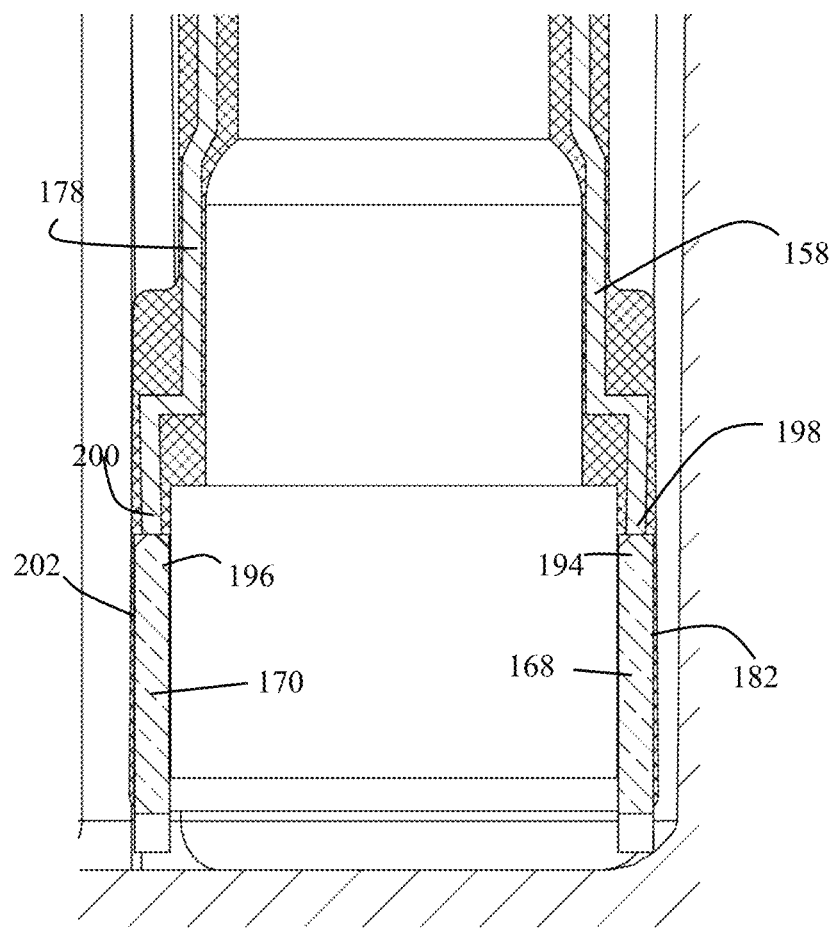
Figure 4D:
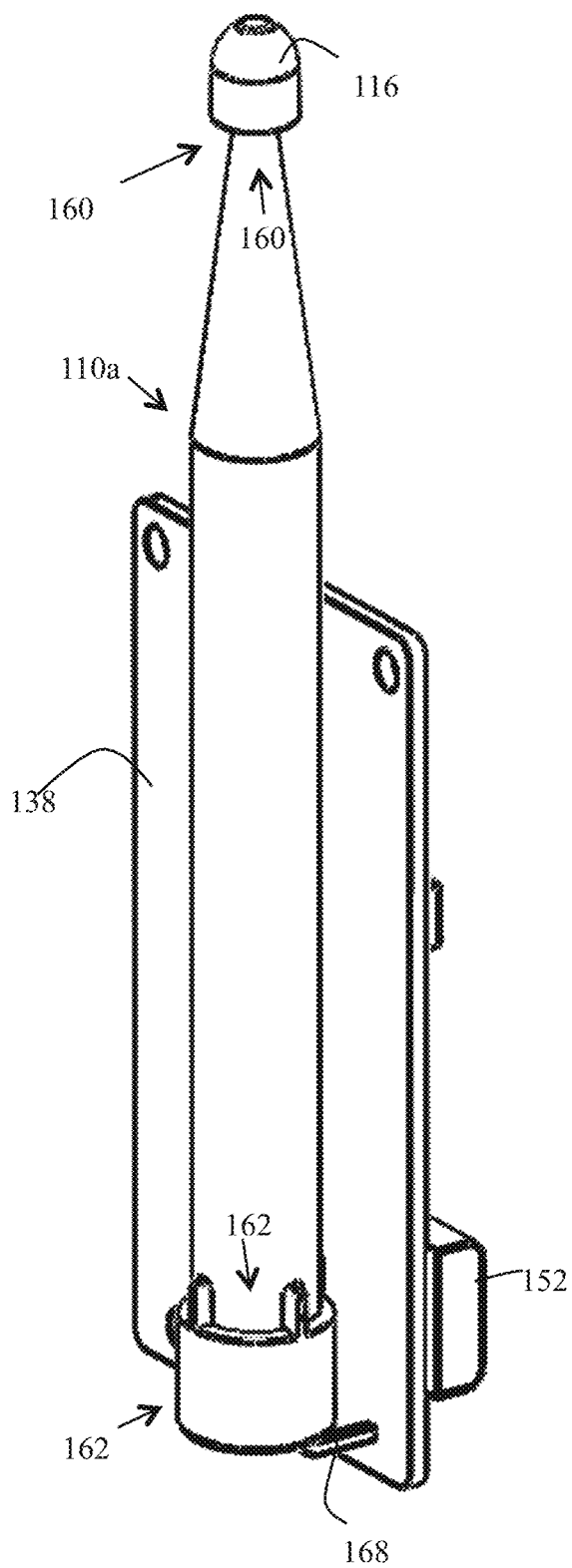
Figure 4E:
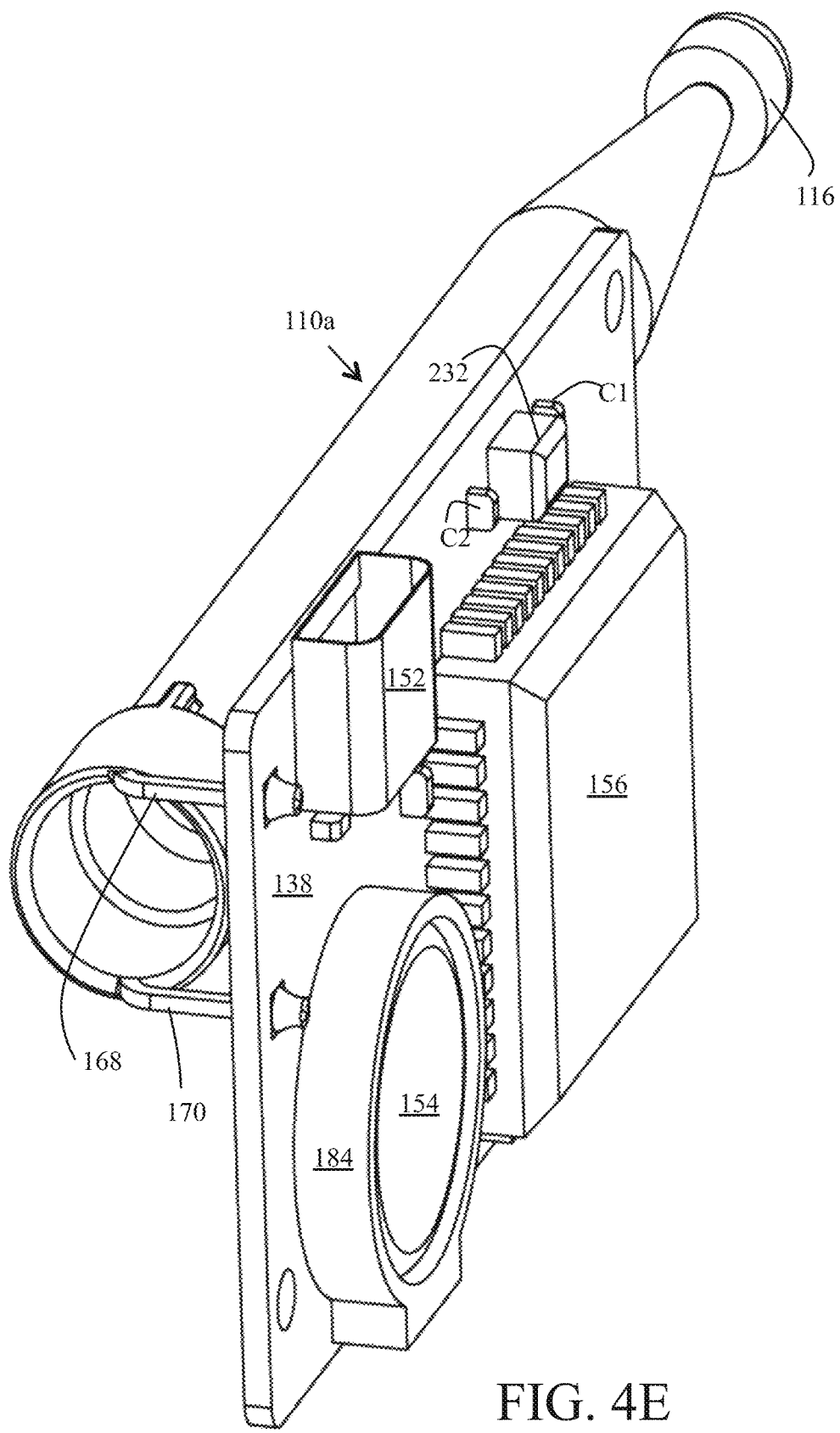
Figure 4F:
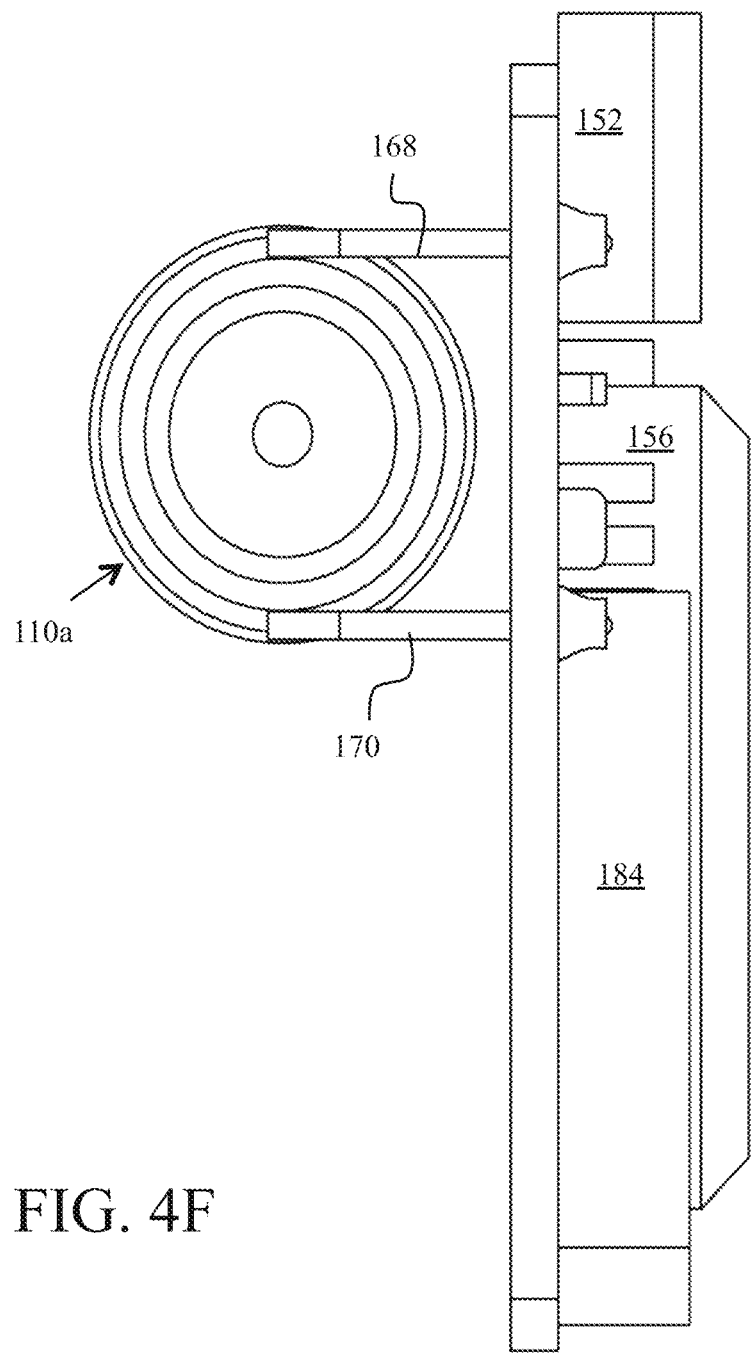
Figure 4K:
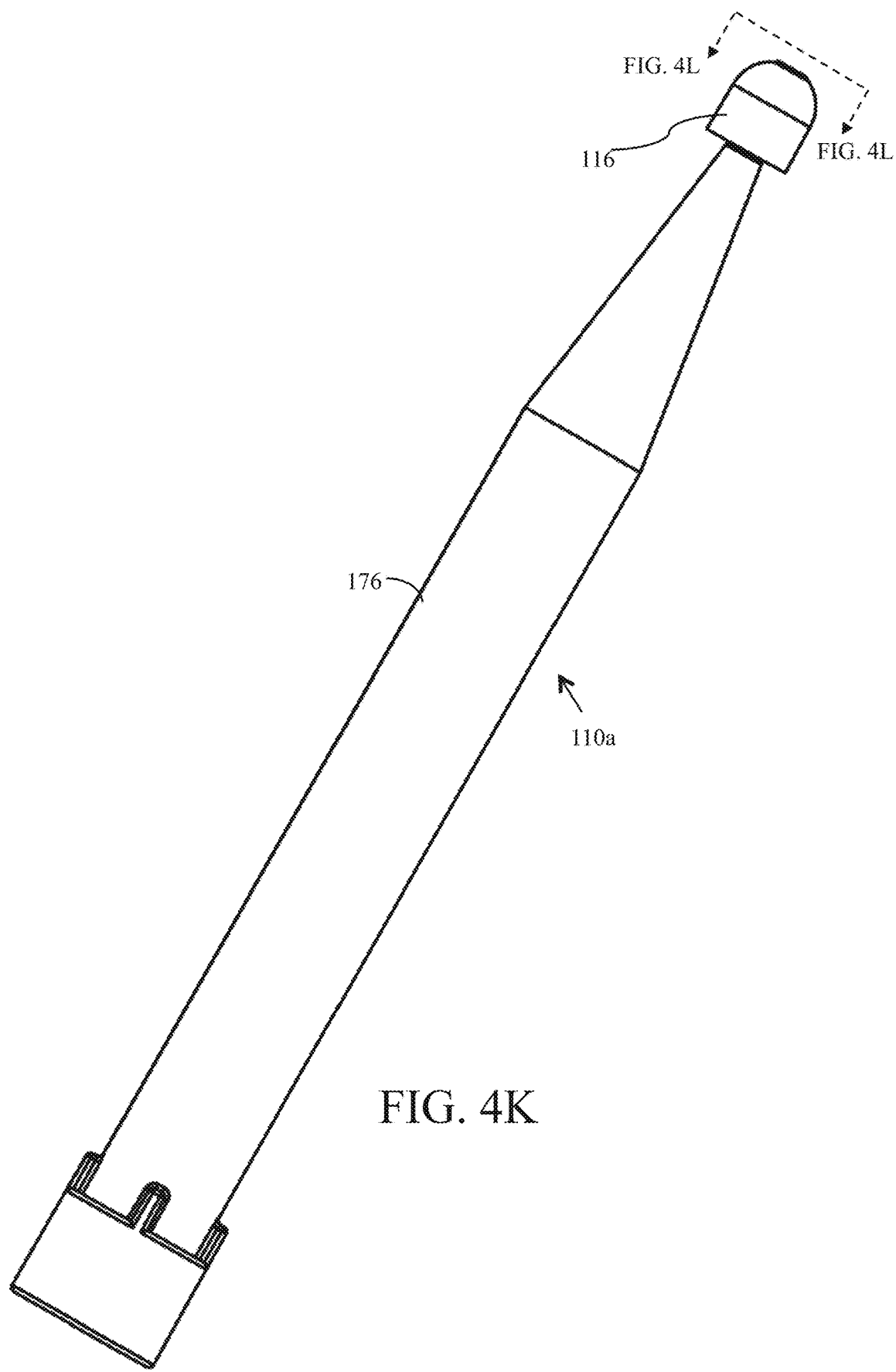
Figure 4M:
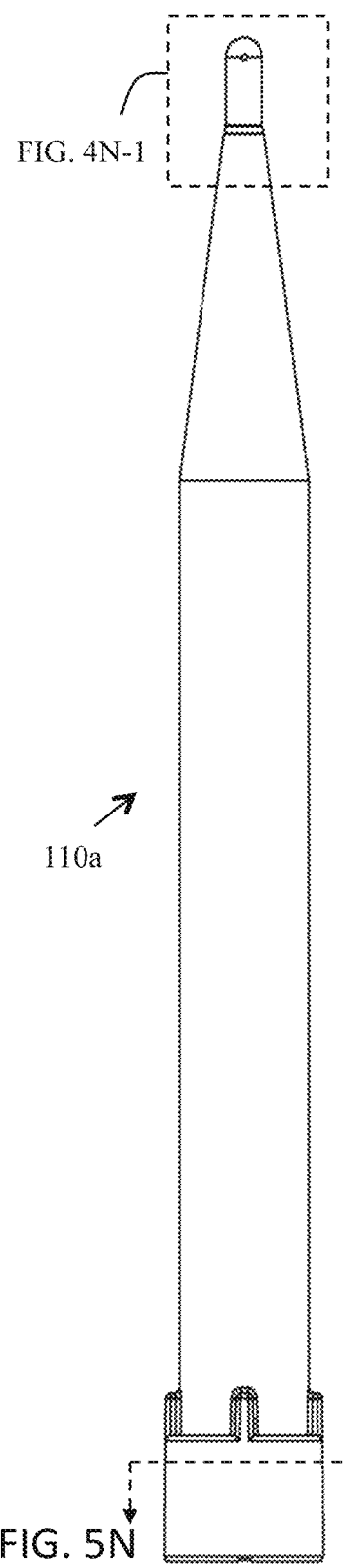
Figures 1, 4N:
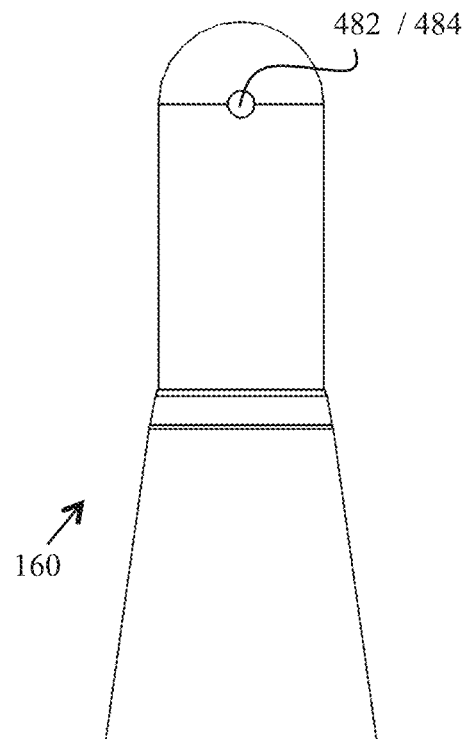
Figure 4N:
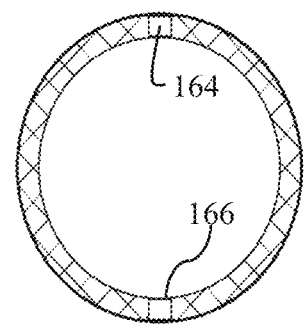
Figure 5A:
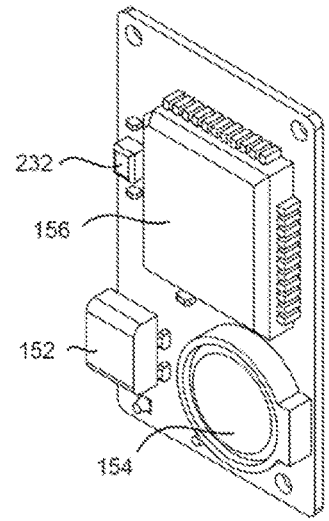
Figure 5B:
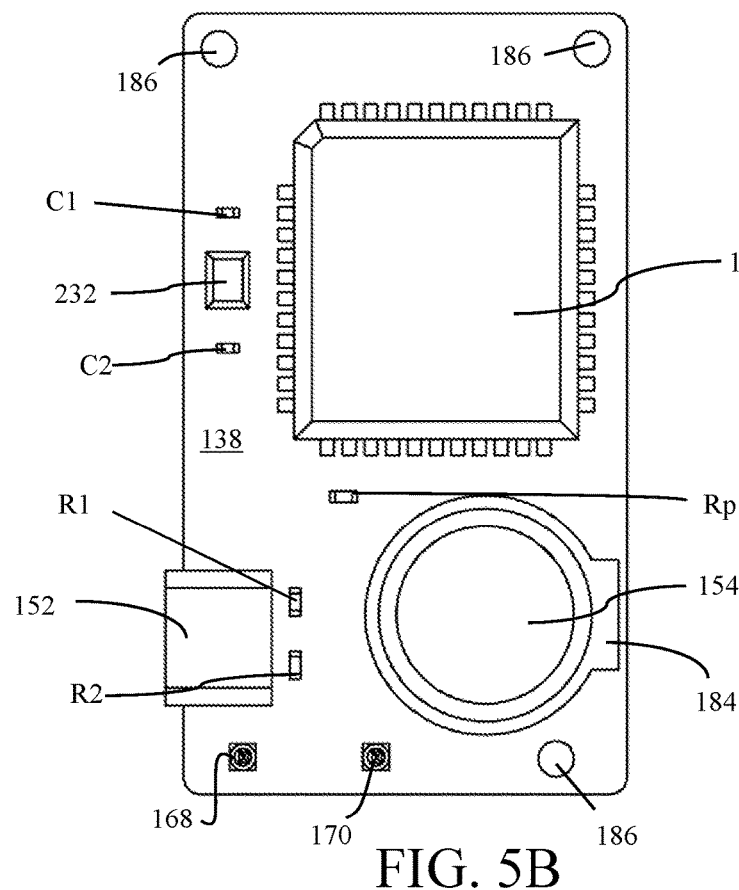
Figure 5C:
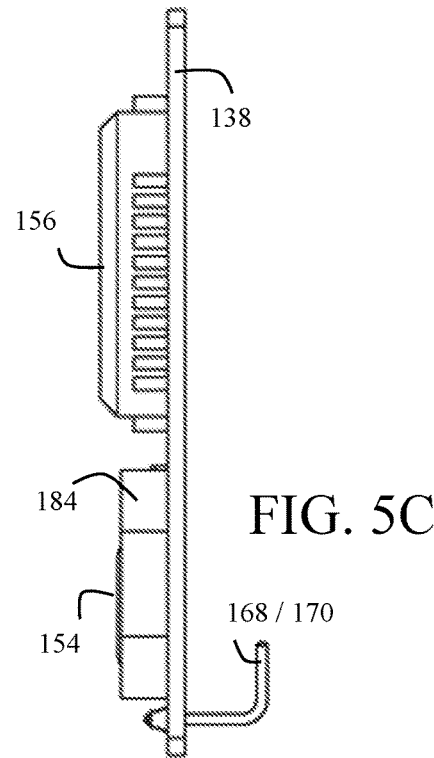
Figure 5D:
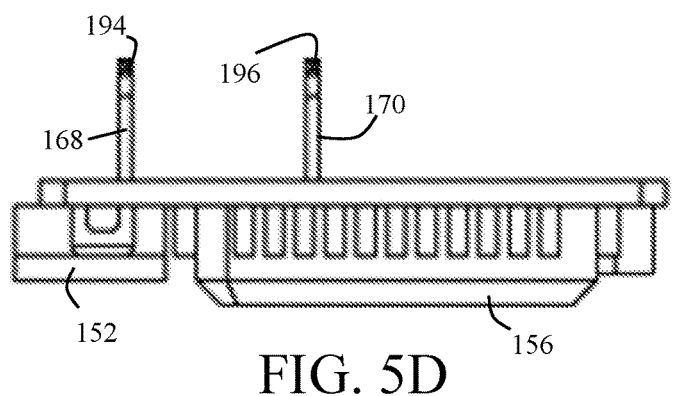

FIGS. 4A to 4N-1 are non-limiting, exemplary illustrations of a center piece, handler probes, and recorder (mounted on PCB) shown in FIGS. 1A to 3B in accordance with one or more embodiments of the present invention. More specifically, FIGS. 4A and 4B illustrate handler probes 110a and 262a in relation to both first side 146 of center piece 126 of cartridge 102a and recorder 114a while FIGS. 4C to 4J illustrate handler probe 110a in relation to recorder 114a without showing cartridge 102a for clarity. FIGS. 4K to 4N-1 illustrate the various views of handler probe 110a only.

As illustrated in FIGS. 4A to 4N-1, at least one handler probe 110a is associated with recorder 114a while housed within cartridge 102a. Handler probe 110a is comprised of a first end 160 that accommodates absorbent member 116 and a second end 162 that includes first and second openings 164 and 166 (FIG. 4H) for receiving first and second electrical engagement pins 168 and 170 of PCB 138 of recorder 114a.

Handler probe 110a further includes first and second conduits or channels (e.g., orifices) 172 and 174 (FIG. 4L) formed within body 176 of handler probe 110a that house first and second wires (electrodes) 158 and 178 that extend from second end 162 from first and second openings 164 and 166 to openings 482 and 484 at first end 160. First and second wires 158 and 178 directly, physically contact with absorbent member 116, but not one another.

First and second orifices 172 and 174 formed within body 176 form pin slots 182 and 202 (FIG. 4C) near second end 162 for insertion of engagement pins 168 and 170. Free ends 194 and 196 of pins 168 and 170 contact second distal ends 198 and 200 of first and second electrodes 158 and 178 when inserted into pin slots 182 and 202 (best shown in FIGS. 4C and 4J).

As best illustrated in FIGS. 4L and 4L-1, at first end 160, first distal ends 190 and 192 of electrodes 158 and 178 extend out of openings 482 and 484 and are bent towards second end 162 of handler probe 110a around a non-conductive protective member 180, which is a small piece of plastic between handler body 176 and absorbent member 116. Absorbent member 116 caps over the illustrated assembly, in direct, physical contact with electrodes 158 and 178. Accordingly, first and second wires 158 and 178 form a set of separate, isolated first and second electrodes within handler probe 110a.

As soon as absorbent member 116 absorbs sufficient volume of fluid 118, fluid 118 absorbed electrically bridges gap 188 (FIG. 4L-1) between first and second electrodes 158 and 178 to form an electrical connection between electrodes 158 and 178. Electrodes 158 and 178 may comprise of any medically suitable material (acceptable biocompatible material) that are conductive, non-corrosive, and may be sterilized, non-limiting examples of which may include for example a surgical grade stainless steel 316LVM wires.

FIGS. 5A to 5D are non-limiting, exemplary illustrations of a non-limiting, exemplary Printed Circuit Board (PCB) of a recorder device in accordance with one or more embodiments of the present invention. As illustrated, PCB 138 includes a battery housing 184 to securely house battery 154, a mounted MCU 156, and in this non-limiting, exemplary instance, a USB connector 152. Further included is a set of securing openings 186 used for securing PCB 138 to cartridge 102a. PCB 138 further includes various electronic components that constitute recorder 114a, details of which are provided below in relation to electrical schematic circuit diagrams in relation to FIGS. 6A to 6C.

Figure 6A:
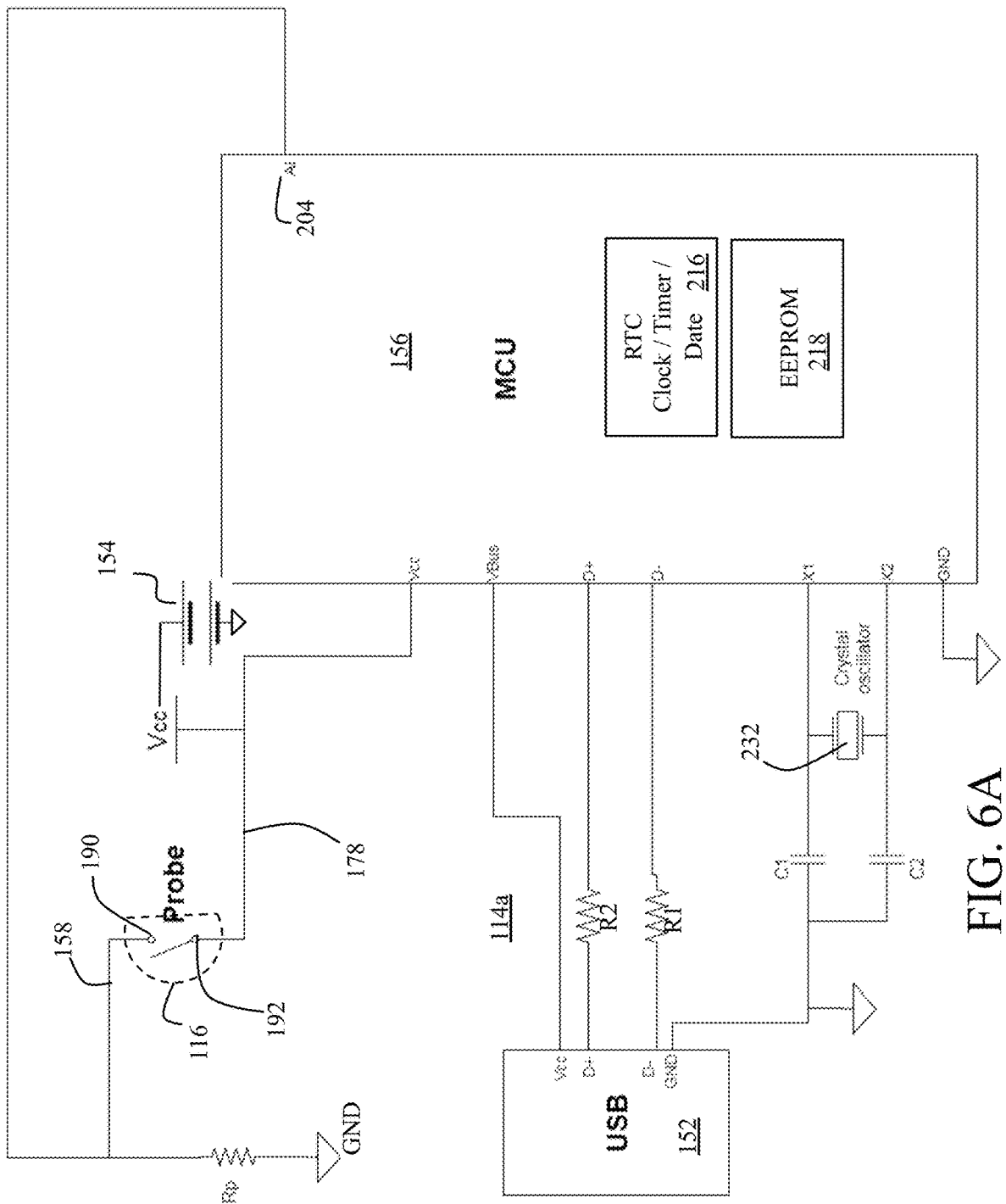
Figure 6B:
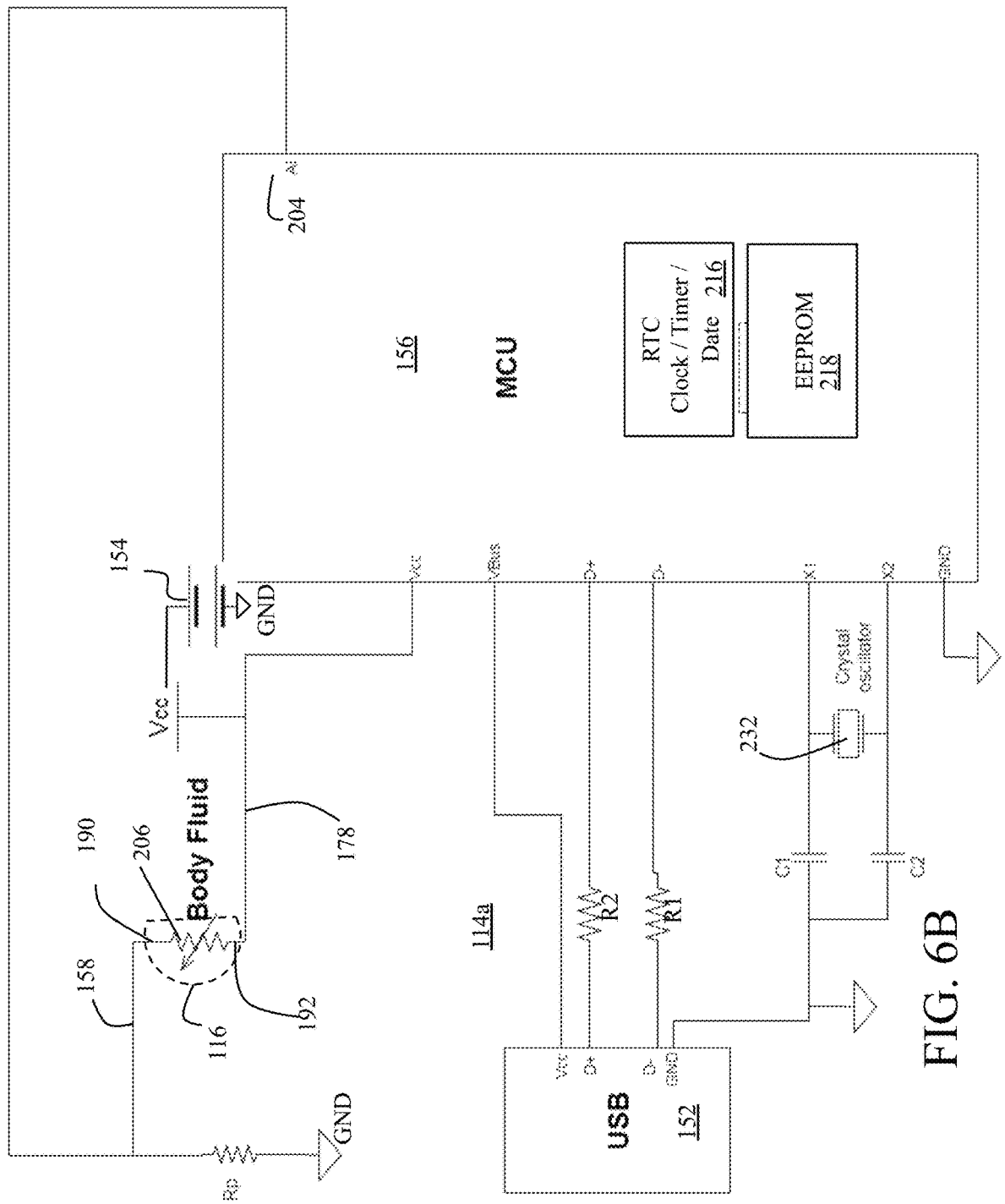
Figure 6C:
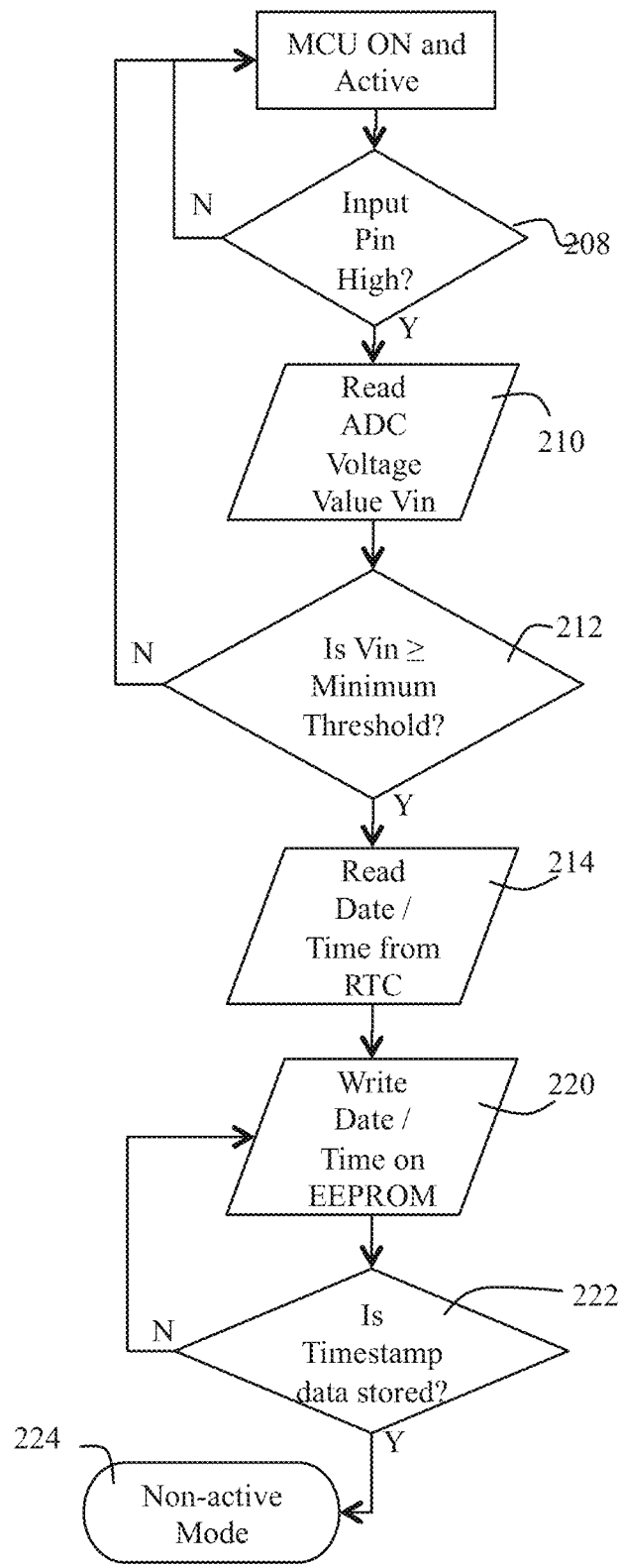

FIG. 6A is a non-limiting, exemplary illustration of an electrical schematic circuit diagram of an unused, dry probe-recorder combination shown in FIGS. 1A to 5D in accordance with one or more embodiments of the present invention. FIG. 6B is a non-limiting, exemplary illustration of the same, but with wetted absorbent member where sufficient fluid has been absorbed in accordance with one or more embodiments of the present invention. FIG. 6C is a non-limiting, exemplary illustration of a flow diagram related to microcontroller unit (MCU) operations shown in FIGS. 1A to 6B in capturing or retrieval, and saving of recorded data, including timestamp data in accordance with one or more embodiments of the present invention.

As illustrated in FIGS. 6A and 6B, first ends 190 and 192 of first and second electrodes 158 and 178 are associated with absorbent member 116 and second ends 198 and 200 of first and second electrodes 158 and 178 are associated with microcontroller unit (MCU) 156 and main power 154 via pins 168 and 170. That is, second end 200 of second electrode 178 is associated with main power input terminal (Vcc) 154 and MCU 156 and a second end 198 of first electrode 158 is associated with ground GND via a current limiting resistor Rp and an Analog to Digital Converter (ADC) input terminal 204 of MCU 156. As detailed below, when absorbent member 116 is dry (not used), first ends 190 and 192 of first and second electrodes 158 and 178 at absorbent member 116 of handler probe 110a represent an open circuit condition.

In the case illustrated in FIG. 6A, pull down resistor Rp limits the current flow between Vcc and ground GND and ensure that MCU ADC terminal 204 does not float. Accordingly, when absorbent member 116 is not wet (open switch or open circuit condition), ADC terminal 204 of MCU 156 is tied to the ground GND through resistor Rp and thus registers 0V, which is the LOW state.

ADC input terminal 204 of MCU 156 receives an analog value represented by a voltage level and converts that analog voltage value to a digital value for MCU 156 further processing. Prior to use, when absorbent member 116 is dry, the value registered (or input) to ADC input terminal 204 of MCU 156 is zero (or low) since that terminal 204 is connected to ground GND via current limiting resistor Rp.

As best illustrated in FIG. 6B, once absorbent member 116 absorbs sufficient amount of fluid 118 to form an electrical connection between electrodes 158 and 178, fluid 118 forms an electrical connection that bridges gap 188 between first and second electrodes 158 and 178 within absorbent member 116, represented by variable resistor 206. It should be noted that the reason the electrical connection is not represented by a "short-circuit" or a closed switch condition, but rather a variable resistor 206, is because fluid (and in particular blood) does have varying resistance.

In this scenario (shown in FIG. 6B), pull-down resistor Rp continues to limit the current flow between Vcc 154 and ground GND and ensure that ADC terminal 204 of MCU 156 does not float while absorbent member 116 is still not fully wet. However, when absorbent member 116 is saturated (variable resistance 206), ADC terminal 204 of MCU 156 has now a direct connection to Vcc 154 and thus registers a higher voltage output which is the HIGH state.

Figure 16A:
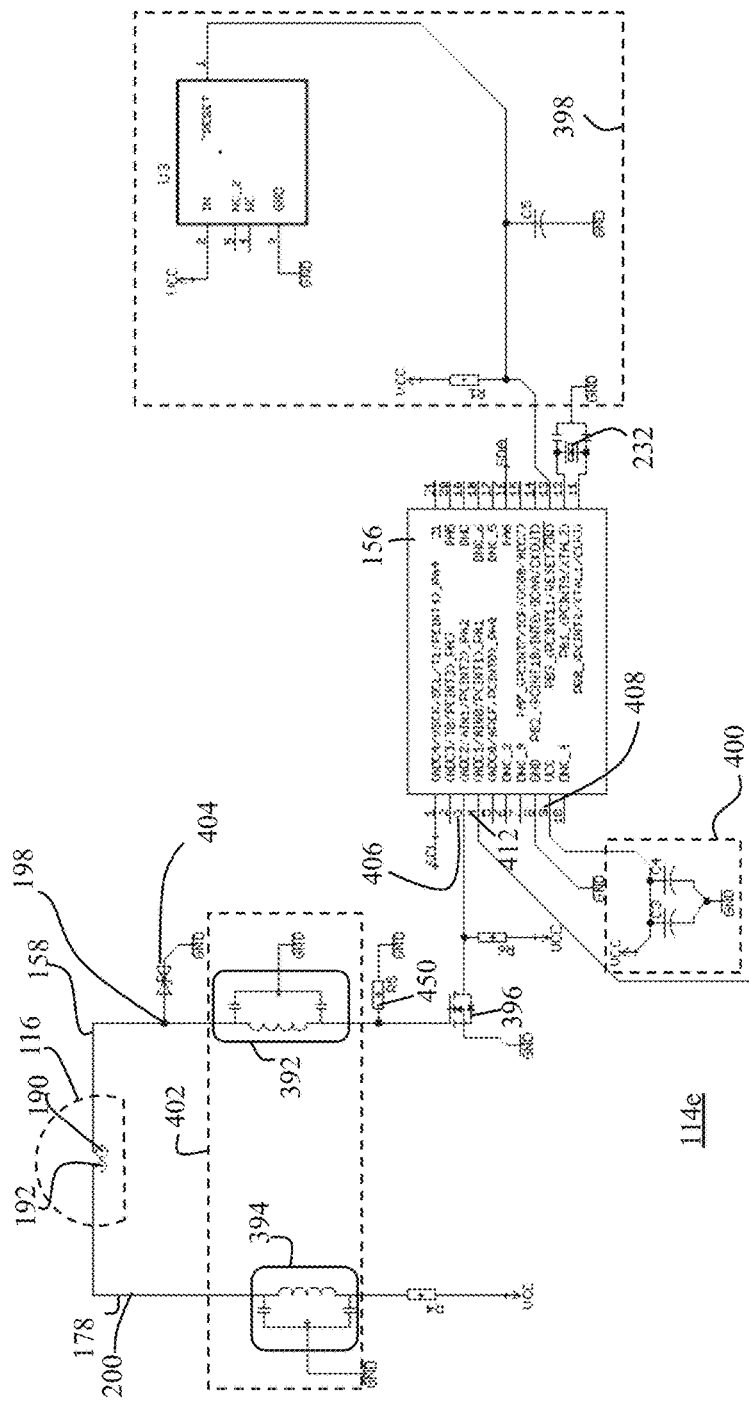
Figure 16A:
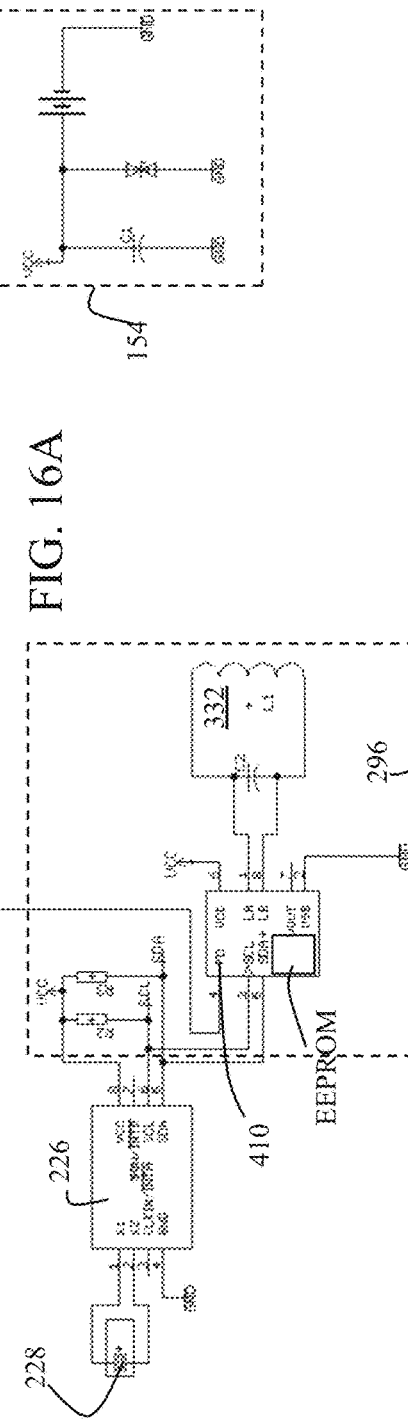

The combination of the fluid resistance 206 and pull-down resistor Rp form a voltage divider circuit, the output of which is input to Analog to Digital (AD) converter terminal 204 of MCU 156. As indicated above, in the open-circuit condition (FIG. 6A), ADC input terminal 204 of MCU 156 is low and hence, as soon as sufficient fluid 118 is absorbed by absorbent member 116 to bridge gap 188 between first and second electrodes 158 and 178 to form an electrical connection therebetween, ADC converter terminal 204 of MCU 156 converts the registered high voltage value to a digital value, triggering or activating timestamp data (detailed below). It should be noted that the actual circuitry of MCU 156 and its connectivity with USB port 152 and main power 154, including all of the illustrated periphery components such as the illustrated resistors R1 and R2, crystal oscillator 232, capacitors C1, C2 are well known. For example, the main power 154 may be a simply battery as illustrated or presented schematically as shown in FIG. 16A.

As best illustrated in the flow chart diagram of FIG. 6C, MCU 156 at operation 208 determines if terminal 204 is High. If MCU 156 determines that terminal 204 is High at operation 208, MCU 156 at operation 210 reads the ADC voltage value Vin. In other words, the voltage "High" at terminal 204 is converted into a digital voltage value Vin by the internal ADC functionality of MCU 156 and read by MCU 156.

MCU 156 at operation 212 determines if voltage Vin at ADC terminal 204 is above a minimum threshold. If MCU 156 determines that the voltage Vin at ADC terminal 204 is above the minimum threshold, MCU 156 at operation 214 reads date/time from an internal Real Time Clock (RTC) 216, and writes the date/time onto an internal EEPROM 218 of MCU 156 at operation 220. At operation 222 MCU 156 determines if all data is stored properly in a conventional manner and if so, at operation 224 MCU 156 switches to a non-active mode. The recorded timestamp data may be accessed through well known communication portals such the illustrated USB connection 152 in a conventionally well known manner.

Figure 7A:
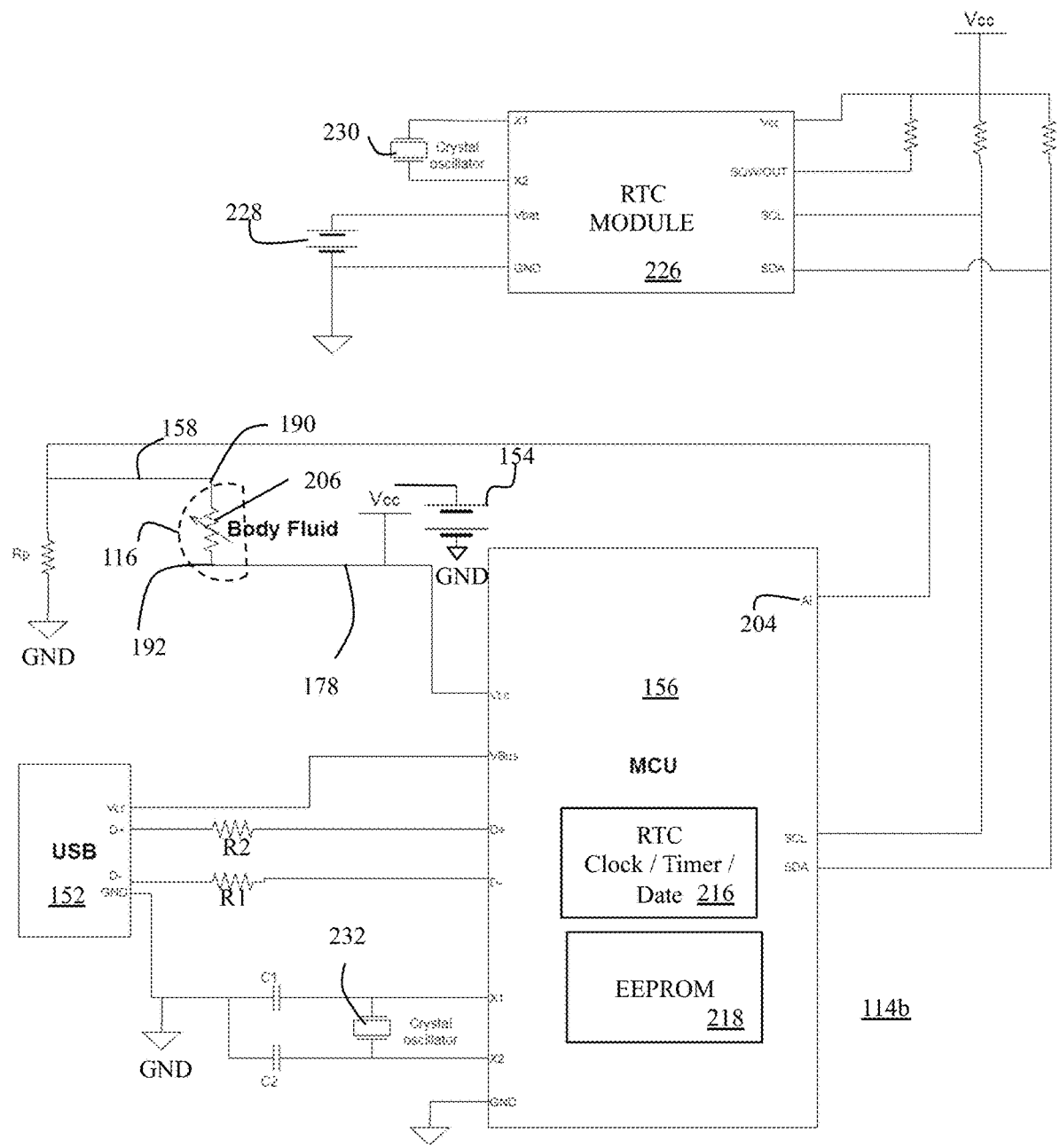
FIGS. 7A and 7B are non-limiting, exemplary electrical schematic and flowchart diagram illustrations of a recorder with an external Real Time Clock (RTC) for a fluid sampling device in accordance with another embodiment of the present invention.
Figure 7B:
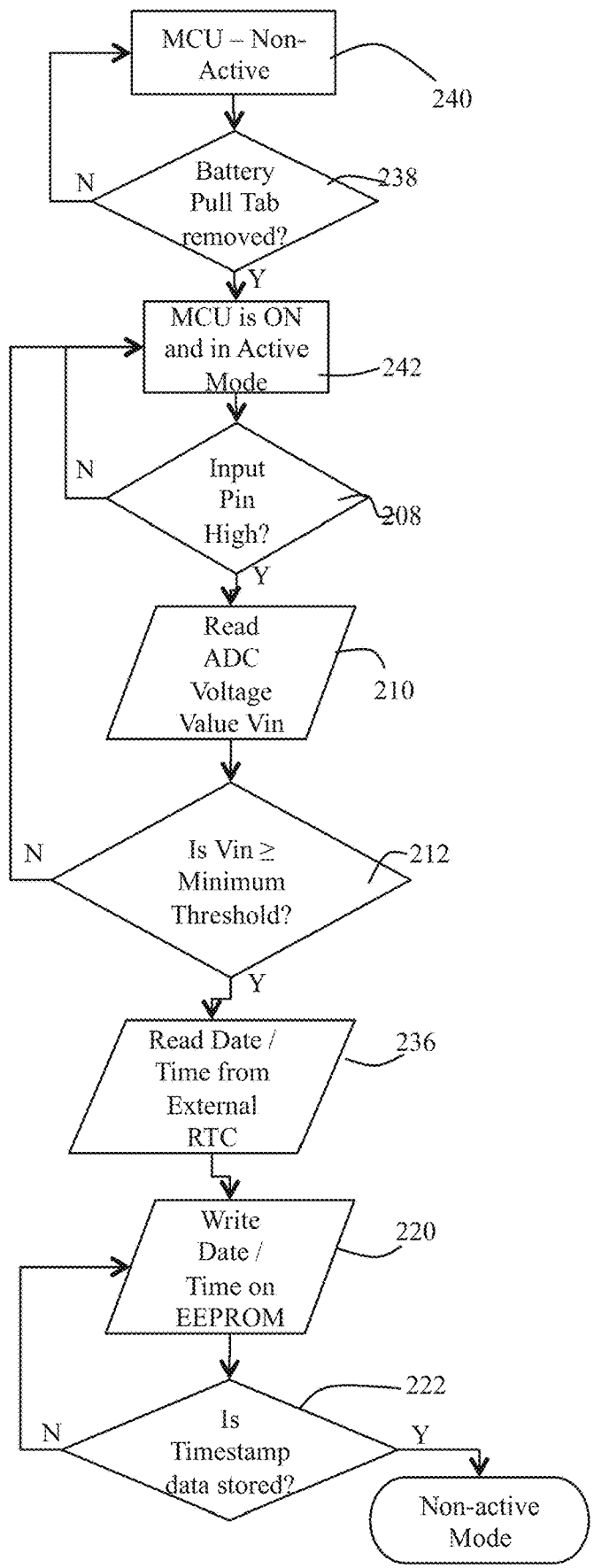

FIGS. 7A and 7B are a non-limiting, exemplary electrical schematic and flowchart diagram illustrations of a recorder with an external Real Time Clock (RTC) in accordance with another embodiment of the present invention. Recorder 114b illustrated in FIGS. 7A and 7B includes similar corresponding or equivalent components, interconnections, functional, operational, and or cooperative relationships as recorder 114a shown in FIGS. 1A to 6C, and described above. Therefore, for the sake of brevity, clarity, convenience, and to avoid duplication, the general description of FIGS. 7A and 7B will not repeat every corresponding or equivalent component, interconnections, functional, operational, and or cooperative relationships that has already been described above in relation to device 100a and its recorder 114a that are shown in FIGS. 1A to 6C but instead, are incorporated by reference herein.

As illustrated in FIGS. 7A and 7B, timestamp data is retrieved from an externally generated external RTC 226 (e.g., DS1307 Real Time Clock) by MCU 156 at operation 236 (FIG. 7B), and stored in MCU 156 internal memory EEPROM 218. MCU 156 input-output (I/O) terminals Serial Clock (SCL) and Serial Data (SDA) are connected to the corresponding I/O terminals SCL and SDA connection of external RTC 226. The same MCU 156 mentioned above in relation to FIGS. 1A to 6C may be used with this embodiment.

It should be noted that external RTC 226 continuously communicates clock (or timestamp data) signals to MCU 156, but the timestamp data is saved only when ADC terminal 204 of MCU 156 is set to High as detailed above in relation to FIG. 6C. That is, only when ADC terminal 204 registers a High digital voltage value Vin is when timestamp data from external RCT 226 is obtained by MCU I/O terminals SCL and SDA. Flow diagram of FIG. 6C is applicable to this embodiment (also shown in FIG. 7B) with the exception that operational 236 of FIG. 7B is "Read Date/Time from external RTC 226" instead of the internal RTC 216.

Use of external RTC module (an external clock) 226 is for extending the life of main power source (VCC) 154. External RTC 226 uses its own battery 228, which uses micro-amperes of current whereas MCU 156 uses milliamperes. Therefore, an external RCT module 226 may slightly increase component count and complexity of circuit, but would extend main battery 154 life of MCU 156.

In this embodiment that uses external RTC module 226, main battery 154 itself may be isolated and protected by well-known "pull-tab" schemes so that recorder 114b is powered ON (operation 242) only after the pull-tab is removed (shown at operation 238) when the fluid sampling device 100a is to be actually used. Accordingly, initially, as indicated by operation 240, MCU 156 is fully powered OFF.

Battery 228 will always power external RTC module 226 to keep track of the actual time and date. In other words, when RTC 226 is manufactured, its battery 228 powers it ON with timer and date properly set and operating. In the embodiments (FIGS. 1A to 6C) that do not use external RTC 226, MCU 156 itself will always be powered ON by main power 154, with appropriate time and date set from the time it is manufactured.

The actual circuitry of RTC 226 and its connectivity with MCU 156, including all of the illustrated periphery components such as the illustrated resistors, crystal oscillator 230, power 228, etc. is well known, including connectivity between MCU 156 and RTC 226 such as the clock signal lines SCL ports and data signal lines SDA ports. The entire electrical components illustrated in FIG. 7A may also be positioned onto one or two PCBs 138 in a well known conventional manner and still covered by second lateral piece 128 of cartridge 102*a* of fluid sampling device 100*a*.

Figure 8A:
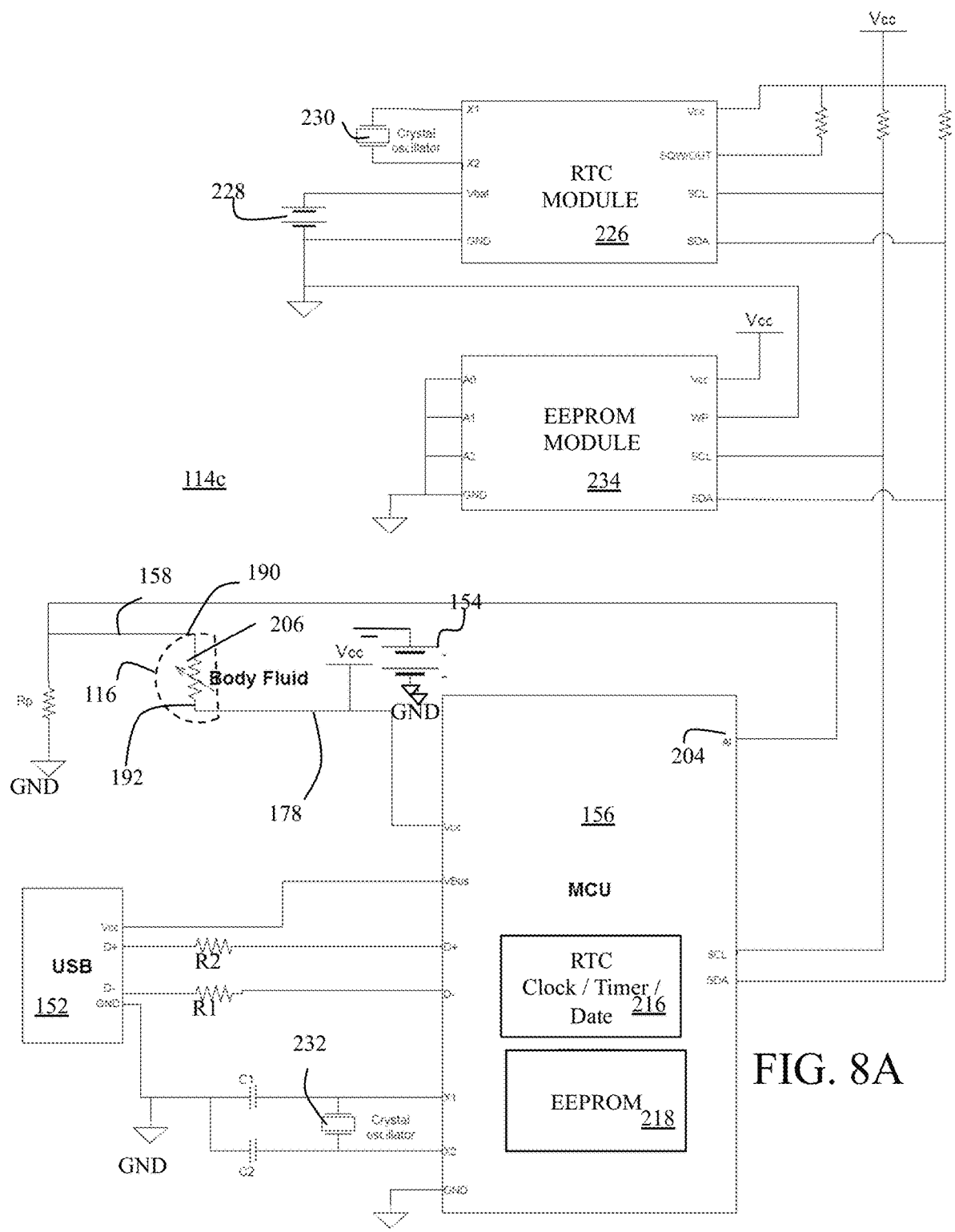
FIGS. 8A and 8B are non-limiting, exemplary electrical schematic illustrations and flowchart diagram of a recorder and MCU operations with an external Real Time Clock (RTC) and an external non-volatile memory in accordance with another embodiment of the present invention.
Figure 8B:
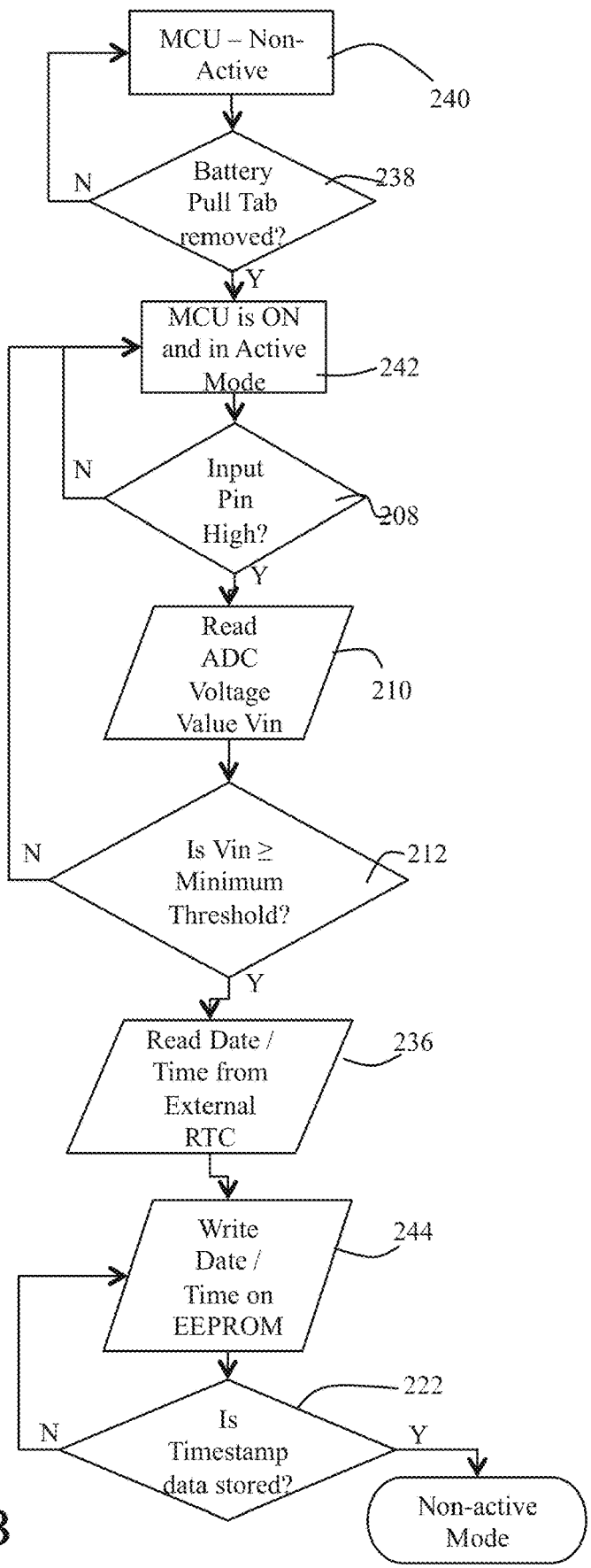

FIGS. 8A and 8B are non-limiting, exemplary electrical schematic illustrations and flowchart diagram of a recorder and MCU operations with an external Real Time Clock (RTC) module and an external memory module (e.g., Electrically Erasable Programmable Read Only Memory (EEPROM)) in accordance with another embodiment of the present invention. Recorder 114*c* illustrated in FIGS. 8A and 8B includes similar corresponding or equivalent components, interconnections, functional, operational, and or cooperative relationships as the recorders 114*a* and 114*b* shown in FIGS. 1A to 7B, and described above. Therefore, for the sake of brevity, clarity, convenience, and to avoid duplication, the general description of FIGS. 8A and 8B will not repeat every corresponding or equivalent component, interconnections, functional, operational, and or cooperative relationships that has already been described above in relation to fluid sampling device 100*a* and recorders 114*a* and 114*b* that are shown in FIGS. 1A to 7B, but instead, are incorporated by reference herein.

As illustrated in FIG. 8A, in this non-limiting, exemplary embodiment, timestamp data is saved onto an external non-volatile memory 234 in addition to being stored in MCU 156 internal memory EEPROM 218. Timestamp data is retrieved from external RTC module 226 by MCU 156 via the illustrated corresponding set of MCU 156 and RTC 226 I/O SCL/SDA terminals, and stored in external memory 234 by the MCU 156 via the illustrated MCU 156 and external memory 234 I/O SCL/SDA terminals.

It should be noted that external RTC 226 continuously communicates clock (or timestamp data) signals, but the timestamp data is saved only when ADC terminal 204 of MCU 156 is set to high. That is, only when ADC terminal 204 registers a High voltage value Vin is when timestamp data from RCT 226 is obtained by MCU 156 I/O terminals SCL and SDA, which are then stored at external memory module (Electrically Erasable Programmable Read Only Memory (EEPROM)) 234. Use of external memory module (an external EEPROM) 234 is for data integrity (backup) in case the main power source 154 is exhausted, which may potential end in loss of data within MCU 156 internal memory 218.

In this non-limiting, exemplary instance shown in FIG. 8B, respective operations 236 and 244 of "Read Date/Time from external RCT" and "Write Date/Time on EEPROM" 244 are referring to external RTC 226 and one or both internal/external EEPROM 218/234. The same MCU mentioned above in relation to FIGS. 1A to 7B may be used with this embodiment. The external RTC 226 may be a DS1307 by MAXIM DALLAS SEMICONDUCTOR and external EEPROM 234 may comprise a 24LC256 by MICROCHIP TECHNOLOGY, INC.

Figure 9A:
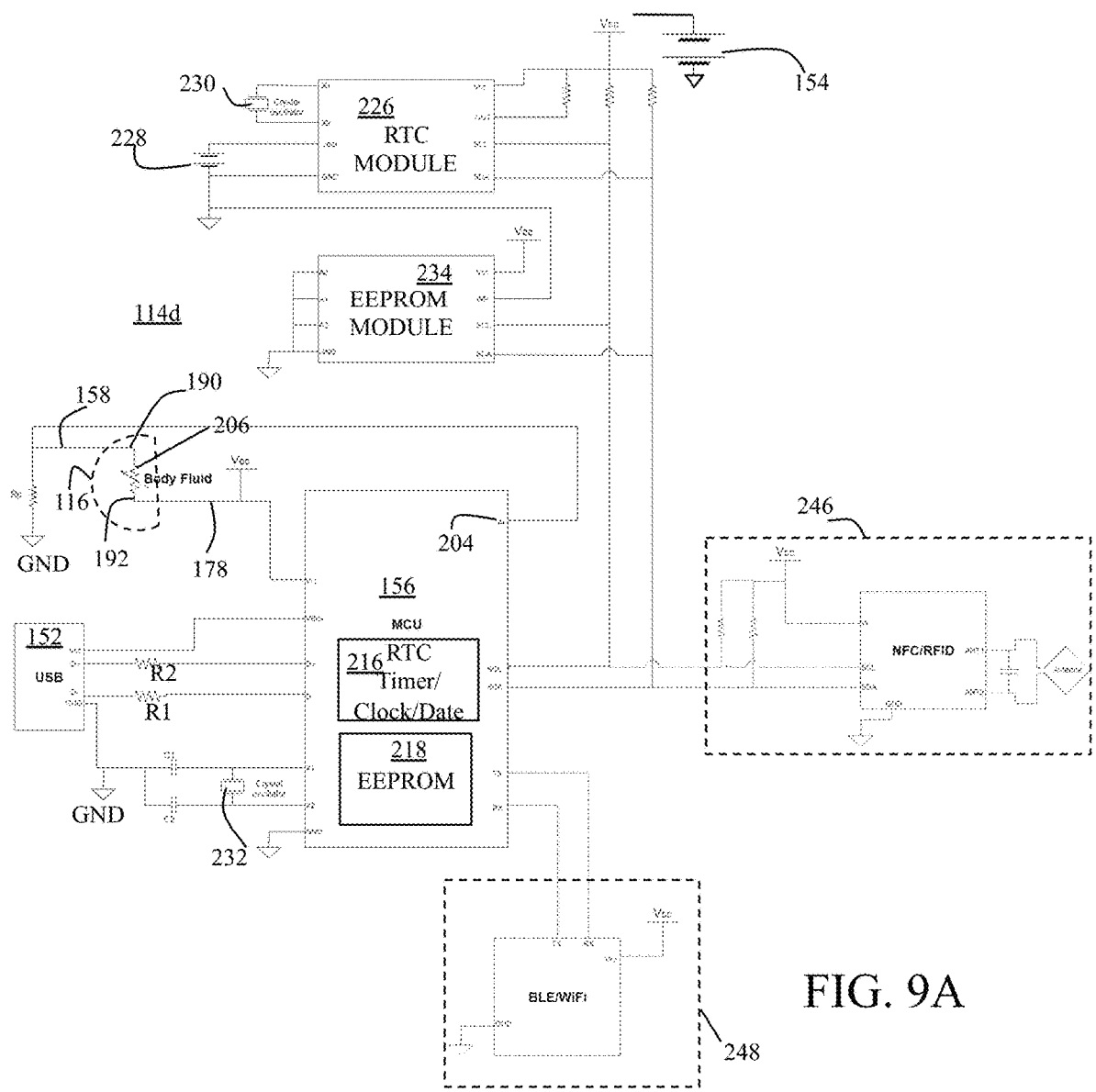
Figures 1, 9B:
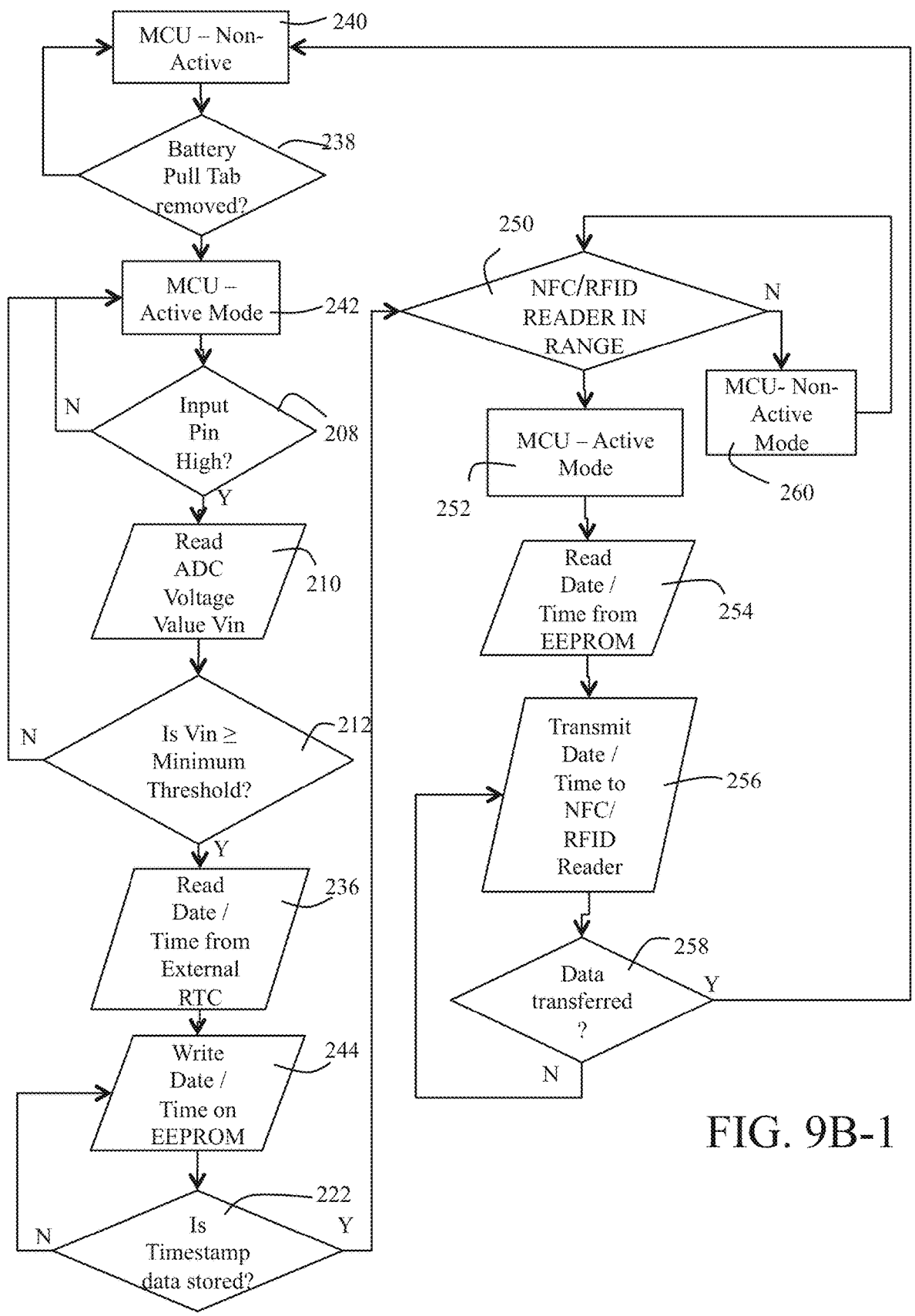
Figures 2, 9B:
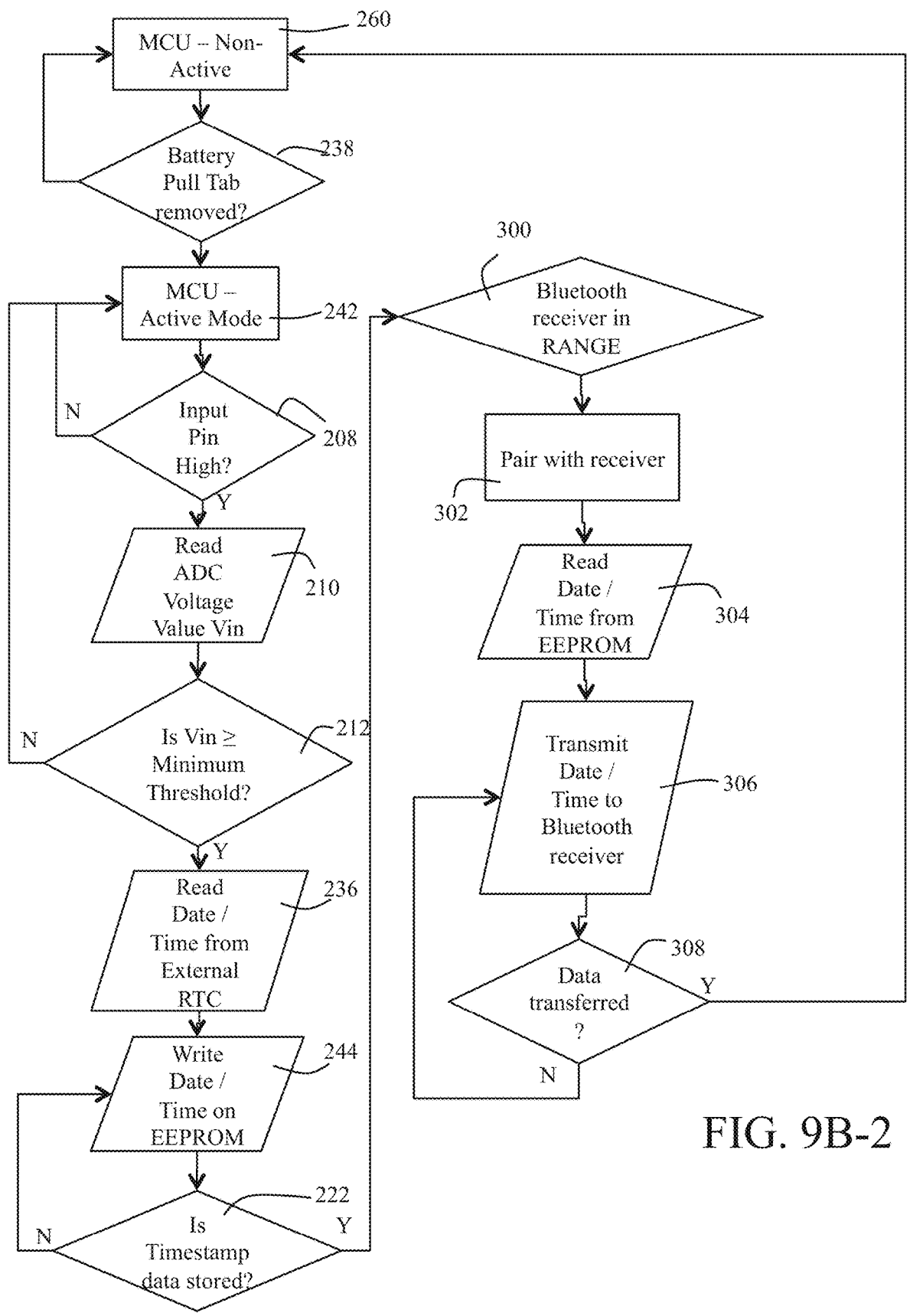

FIGS. 9A to 9B-2 are non-limiting, exemplary electrical schematic illustrations and flowchart diagram of a recorder and MCU operations with an external Real Time Clock (RTC) module and an external memory module (e.g., Electrically Erasable Programmable Read Only Memory (EEPROM)), including use of different types of communications portals in accordance with another embodiment of the present invention. Recorder 114*d* illustrated in FIGS. 9A to 9B-2 includes similar corresponding or equivalent components, interconnections, functional, operational, and or cooperative relationships as recorders 114*a*, 114*b*, and 114*c* shown in FIGS. 1A to 8B, and described above. Therefore, for the sake of brevity, clarity, convenience, and to avoid duplication, the general description of FIG. 9A to 9B-2 will not repeat every corresponding or equivalent component, interconnections, functional, operational, and or cooperative relationships that has already been described above in relation to fluid sampling device 100*a* and recorders 114*a*, 114*b*, and 114*c* that are shown in FIGS. 1A to 8B, but instead, are incorporated by reference herein.

As illustrated in FIGS. 9A to 9B-2, timestamp data may be retrieved from one or both the internal and or external memory modules 218 and or 234 by MCU 156, which outputs the same by a desired communications protocol. MCU 156 may comprise of various communications ports or portals through which it may communicate timestamp data, non-limiting, non-exhaustive listing of examples of which may include any one or more of USB 152, NFC and or RFID 246, WI-FI and or BLUETOOTH 248, etc. It should be noted that circuitry for each communication module (USB, NFC, RFID, WiFi, Bluetooth, etc.) is well known, including manner of their respective connectivity with MCU 156. In this non-limiting, exemplary instance, circuitry for NFC/RFID 246 and WiFi/Bluetooth 248 and their connections with MCU 156 are illustrated in broken lines to indicate "optional" use of various known communications protocols. Accordingly, data may be retrieved and communicated by any well known communications protocol, non-limiting, non-exhaustive listing of examples of one or more of which are exemplarily illustrated in FIGS. 9B-1 and 9B-2.

FIG. 9B-1 is a non-limiting, exemplary flow diagram that illustrations communication of data via the illustrated NFC and or RFID in FIG. 9A in accordance with one or more embodiments of the present invention. MCU 156, external RTC 226, and EEPROM 234 may be the same as above in relation to FIGS. 1A to 8B, and the NFC may comprise an RF430CL330H by TEXAS INSTRUMENTS.

In this non-limiting, exemplary instance shown in FIG. 9B-1, respective operations 250 to 260 for NFC protocols are equally applicable to RFID communication protocols. As illustrated, once timestamp data is stored within memory (internal and or external EEPROM 218 and or 234), MCU 156 determines if NFC (or an RFID) reader is within an antenna range of the illustrated NFC/RFID 246 at operation 250. If MCU 156 determines NFC (or RFID) reader is not within an antenna range of NFC/RFID 246, MCU 156 reverts back to non-active mode at operation 260 otherwise, MCU 156 switches to active-mode at operation 252.

At operations 254 and 256 illustrated in FIG. 9B-1, MCU 156 may read timestamp data from EEPROM (internal or external) 218 or 234, and transmit the same to a corresponding reader (NFC reader or RFID reader), depending on which communication device (NFC or RFID) is associated with recorder 114. At operation 258, MCU 156 determines if data transfer is complete and if so, MCU 156 reverts back to non-active mode at operation 240 otherwise, MCU 156 continues to loop through operation 256 until all data is transferred.

FIG. 9B-2 is a non-limiting, exemplary flow diagram illustration for communication of data via the illustrated Bluetooth in FIG. 9A in accordance with one or more embodiments of the present invention. In this non-limiting, exemplary instance, once MCU 156 determines that timestamp data is stored at operation 222, when fluid sampling device 100*a* is brought near Bluetooth device range at operation 300 and paired at operation 302, MCU 156 reads timestamp information from memory (internal and or external EEPROM 218 and or 234) at operation 304 and instructs transmission of the same to a Bluetooth receiver at operation 306. At operation 308 MCU 156 determines if data is transferred after which, MCU 156 becomes non-active.

As indicated above, other known communication protocols such as WiFi may also be used in well-known, conventional manner to transmit and communicate timestamp data. Accordingly, the fluid sampling device 100a may transmit timestamp data through well known communication protocols (including WiFi), a few non-limiting, non-exhaustive listings of examples of which have been illustrated.

FIGS. 10A to 16B are non-limiting, exemplary illustrations of a fluid sampling device in accordance with another embodiment of the present invention. The fluid sampling device 100b illustrated in FIGS. 10A to 16B includes similar corresponding or equivalent components, interconnections, functional, operational, and or cooperative relationships as the device 100a that is shown in FIGS. 1A to 9B-2, and described above. Therefore, for the sake of brevity, clarity, convenience, and to avoid duplication, the general description of FIGS. 10A to 16B will not repeat every corresponding or equivalent component, interconnections, functional, operational, and or cooperative relationships that has already been described above in relation to device 100a that is shown in FIGS. 1A to 9B-2 but instead, are incorporated by reference herein.

FIGS. 10A to 10E are non-limiting, exemplary illustrations of a fluid sampling device 100b in a non-limiting, exemplary form-factor of a cartridge 102b that is illustrated in the closed position in accordance with one or more embodiments of the present invention. FIGS. 11A to 11D are non-limiting, exemplary illustrations of the fluid sampling device 100b shown in FIGS. 10A to 10E, but with cartridge 102b illustrated in the open position in accordance with one or more embodiments of the present invention. FIGS. 11A to 11D also progressively illustrate a non-limiting, exemplary method of use of fluid sampling device 100b in accordance with one or more embodiments of the present invention, which is identical to fluid sampling device 100a.

As illustrated in FIGS. 10A to 11D, in this non-limiting, exemplary embodiment, four hander probes 110b and 262a with their respectively mounted absorbent members 116 are included in cartridge 102b of fluid sampling device 100b. As detailed below and best shown in FIG. 13B, handler probe 110b and 262a are housed within cartridge 102b at different elevation levels so that their respective absorbent members 116 are positioned at different heights. Positioning absorbent members 116 in different height elevations facilitates in preventing potential contact of other absorbent members 116 with other fingers of the hand, while one absorbent member 116 is in contact with fluid sample 118 (best shown in FIG. 11D). Accordingly, as detailed below, handler probe 110b has height 310 (defined along its longitudinal axis, FIG. 13K) that is longer in span than height 312 (FIG. 12A) of handler probes 262a or 110a.

Figure 12A:
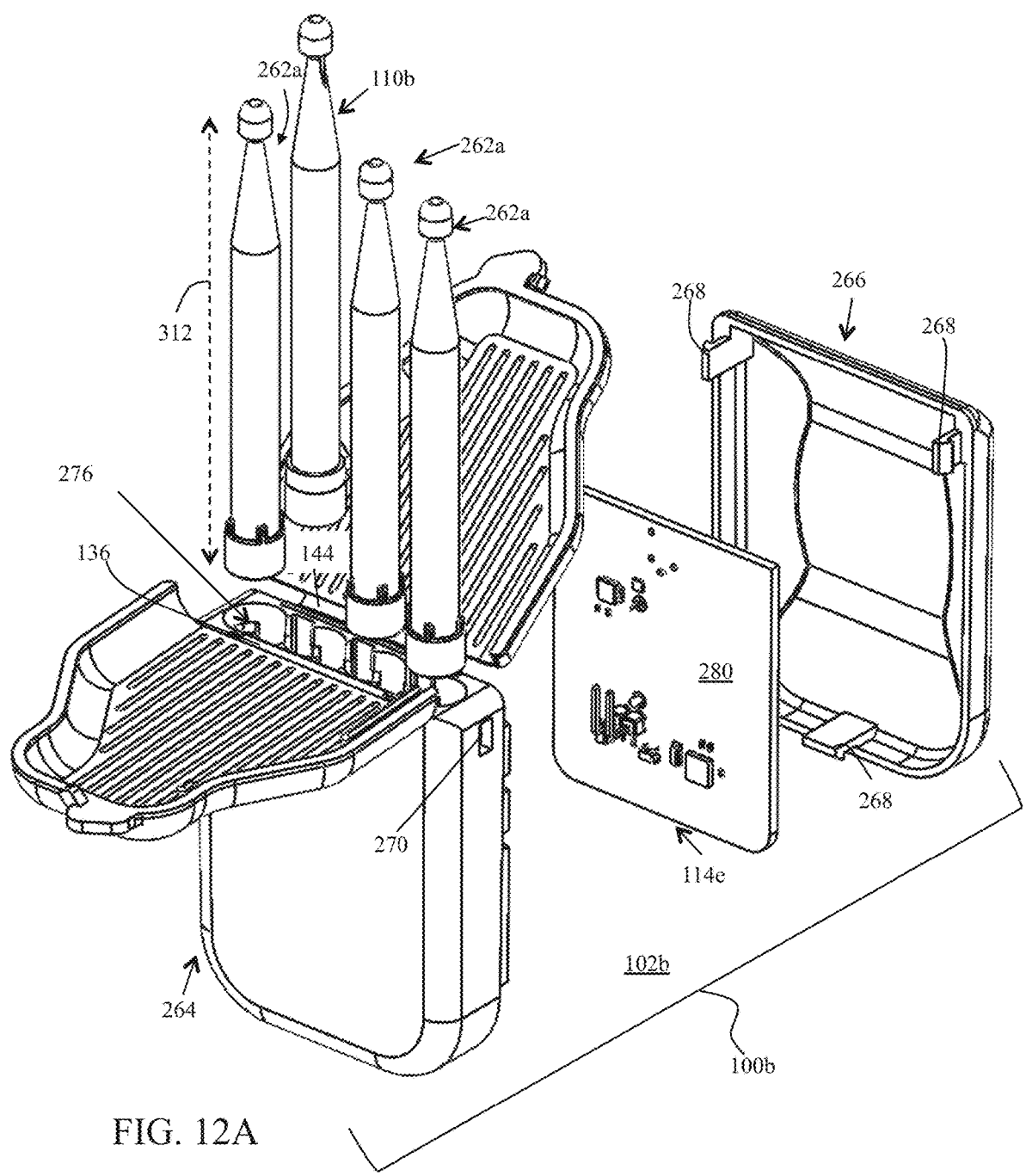
Figure 12B:
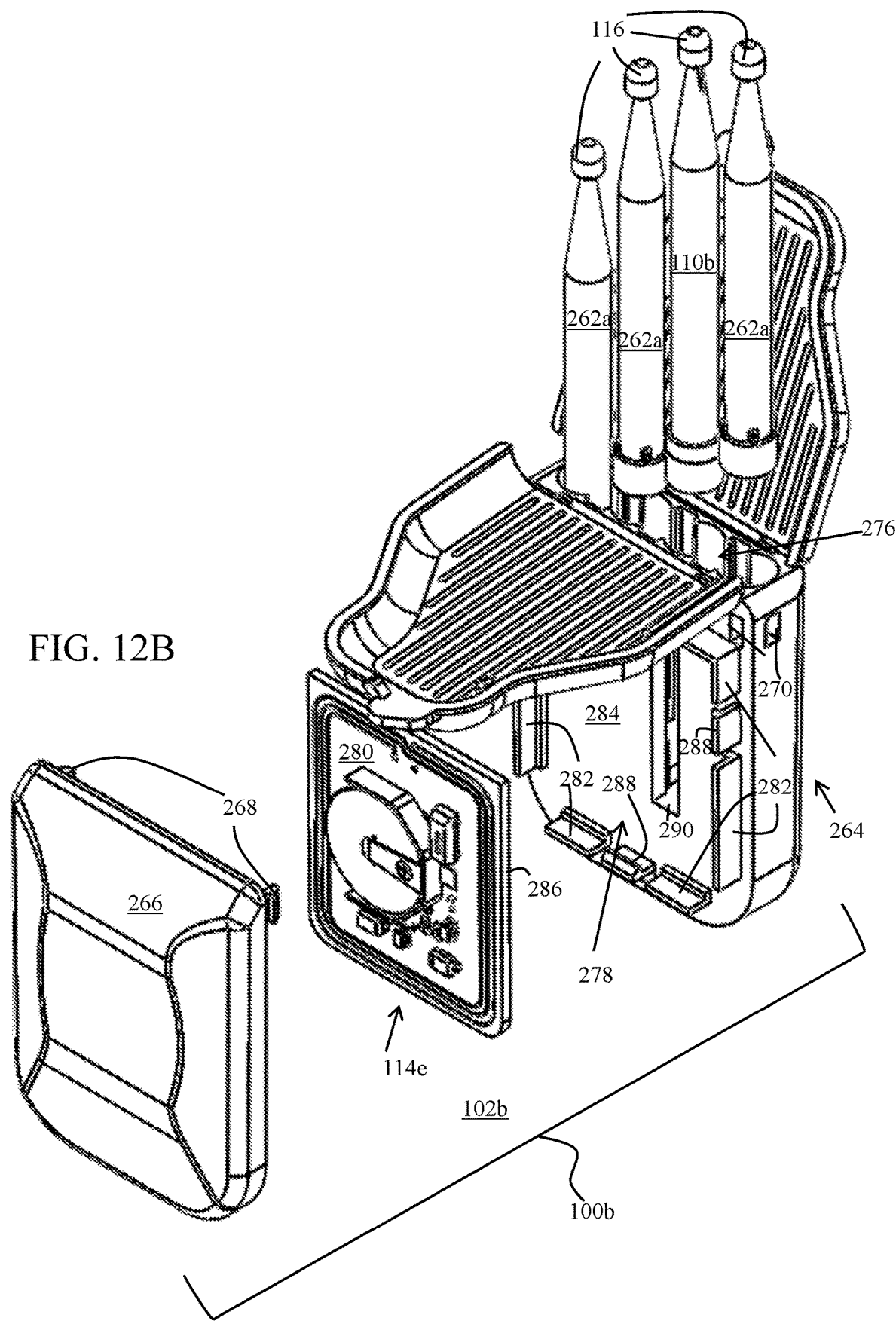

FIGS. 12A and 12B are non-limiting exemplary exploded view illustrations of the cartridge shown in FIGS. 10A to 11D in accordance with one or more embodiments of the present invention. The exploded views shown in FIGS. 12A and 12B illustrate disassembled, separated pieces of cartridge 102b that show the cooperative working relationship, orientation, positioning, and exemplary manner of assembly of the pieces in accordance with one or more embodiments of the present invention.

As illustrated in FIGS. 12A and 12B, cartridge 102b of fluid sampling device 100b is comprised of a housing 264 with a cover 266 that covers over PCB 280 of recorder 114e. Cover 266 may be connected with housing 264 by a variety of well known methods non-limiting examples of which may include well-known "snap-fit" joints or connections with hook-type projections 268 from one piece being snapped into corresponding interlocking recesses or openings 270 in another, by annular snap fits, or by other well known methods.

Cartridge 102b includes an upper portion 272 (FIG. 10D) that comprises first and second covers 104 and 112 and a lower portion 274 that houses handler probes 110b and 262a. Interior side 276 (FIG. 12A) of lower portion 274 of cartridge 102b is configured to securely accommodate handler probes 110a and 262a. As illustrated, first and second covers 104 and 112 are associated with lower portion 272 by living hinge 136 and 144, with covers 104 and 112 including vent opening 120 and 122 to allow for ventilation, which facilitates drying of fluid loaded absorbent members 116.

A side 278 (FIG. 12B) of lower portion 274 of cartridge 102b of fluid sampling device 100b accommodates electronics (one or more Printed Circuit Board-PCBs) 280 of recorder device 114e required for recording of data related to sampled fluid. As best illustrated in FIG. 12B, side 278 includes a set of periphery walls 282 extending vertically from base 284 of side 278 that are oriented to surround, encompass, or "frame" PCB 280, and allow for a tight fit of the periphery edges 286 of PCB 280.

Side 278 further includes hook-type projections 288 enable part of edges 286 along the four sides of PCB 280 to snap and be secured onto side 278. Side 278 further includes opening 290 that enables access to PCB 280 (and hence, interior side 276). Opening 290 allows pins 168 and 170 to extend from PCB 280 through opening 290 and connect with handler probe 110b. It should be noted that PCB 280 may also be mounted and secured to side 278 by other well known conventional method such as by use of adhesives, rivets, or other fasteners and the like.

As well be detailed below, recorder 114e is similar to recorders 114a to 114d mentioned above in relation to previously described embodiments however, recorder 114e further comprises other electronics including for example a voltage regulator 292, and various signal processing filters 294 and 298. The electronics of recorder 114e may be fully mounted onto one or more PCBs 280 as best illustrated in FIGS. 15A to 15E. In this non-limiting exemplary instance, recorder device 114e includes a well-known Dynamic Near Field Communication (DNFC) unit 296 that may be used to transmit timestamp data to a corresponding NFC reader.

As well be apparent below, one or more handler probes 110b may include conductive electrodes 158 and 178 that may be electrically and mechanically connected to recorder device 114e. In this non-limiting exemplary instance, only one absorbent probe 116 of handler probe 110b is electrically connected to recorder device 114e via electrodes 158 and 178.

Figure 13A:
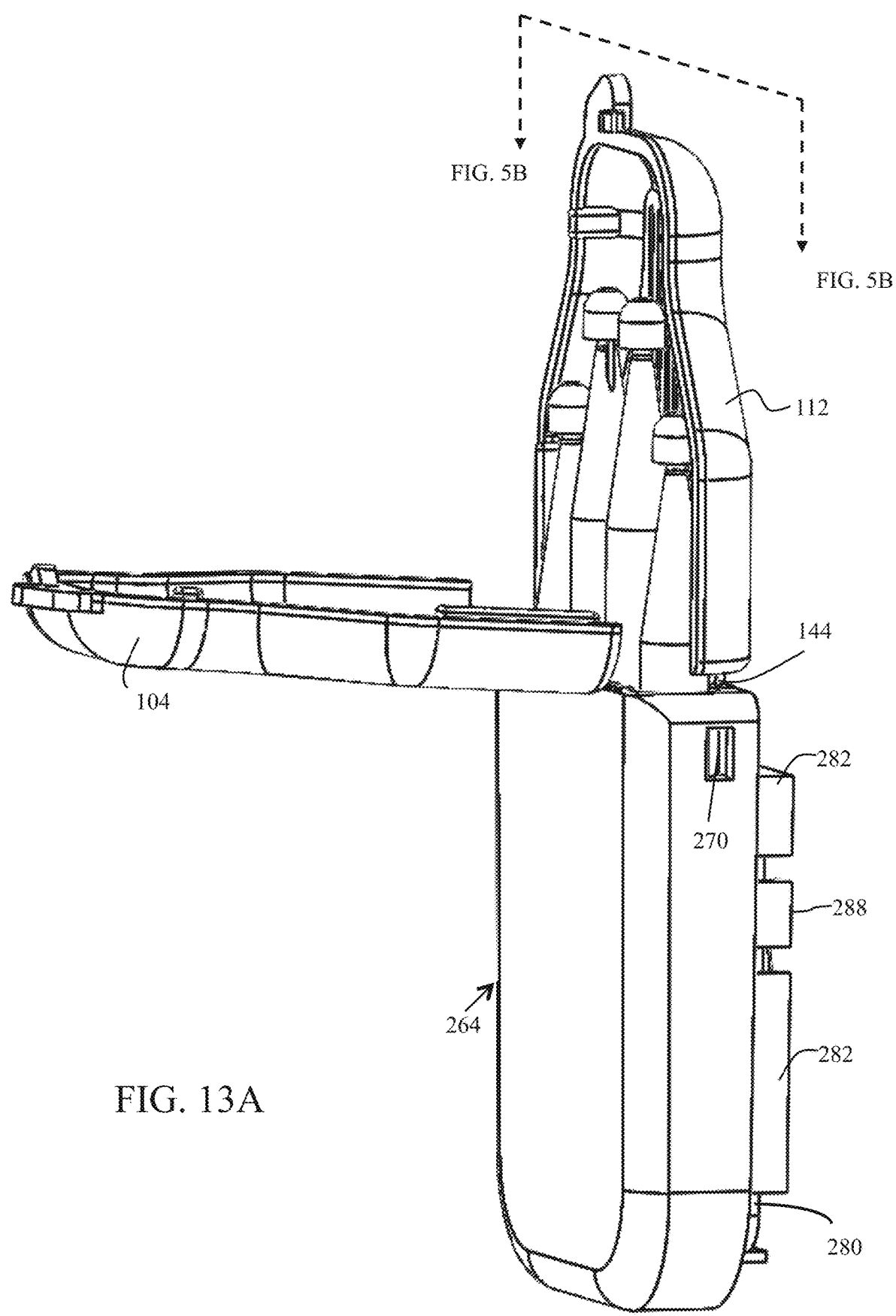
Figure 13B:
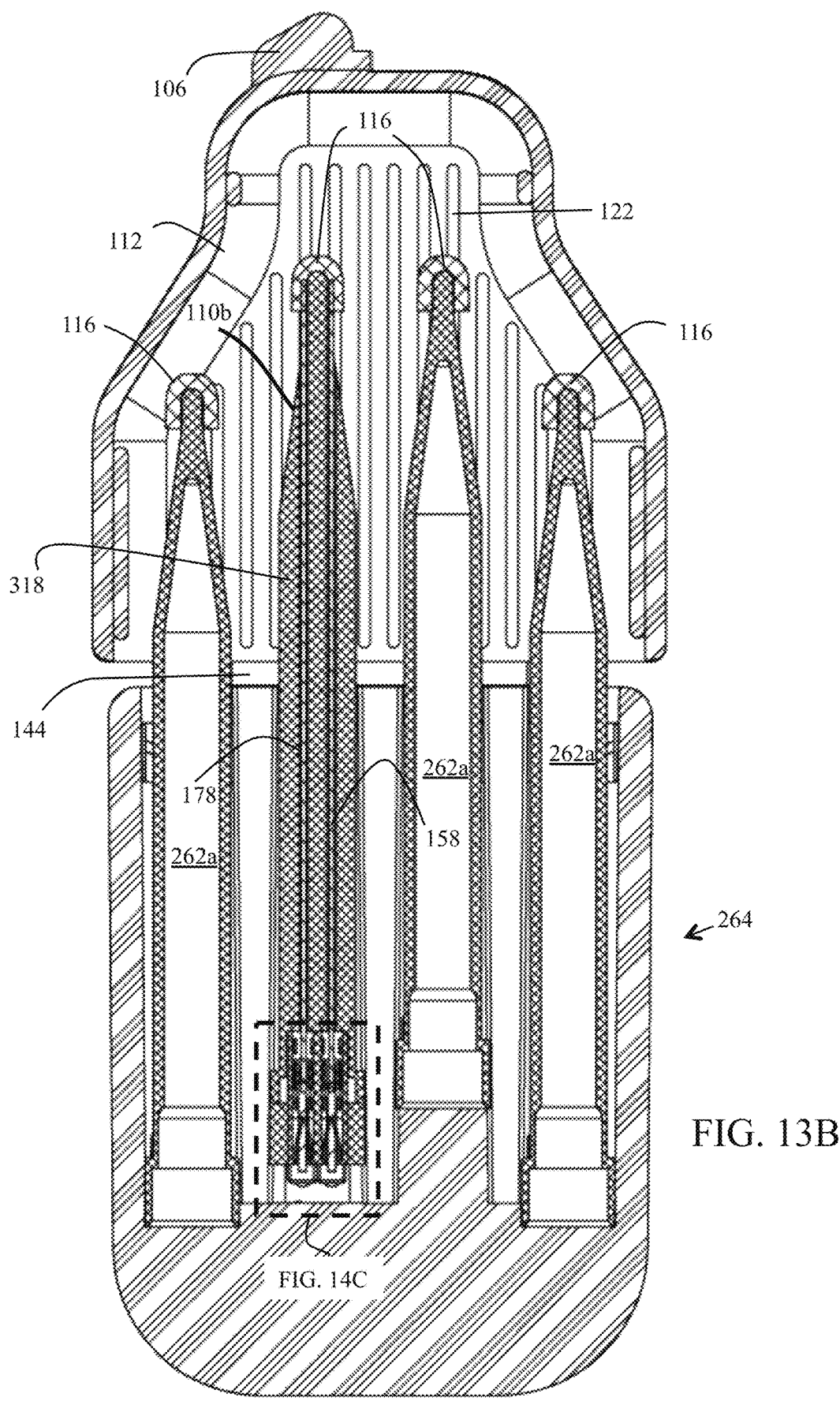
Figure 13C:
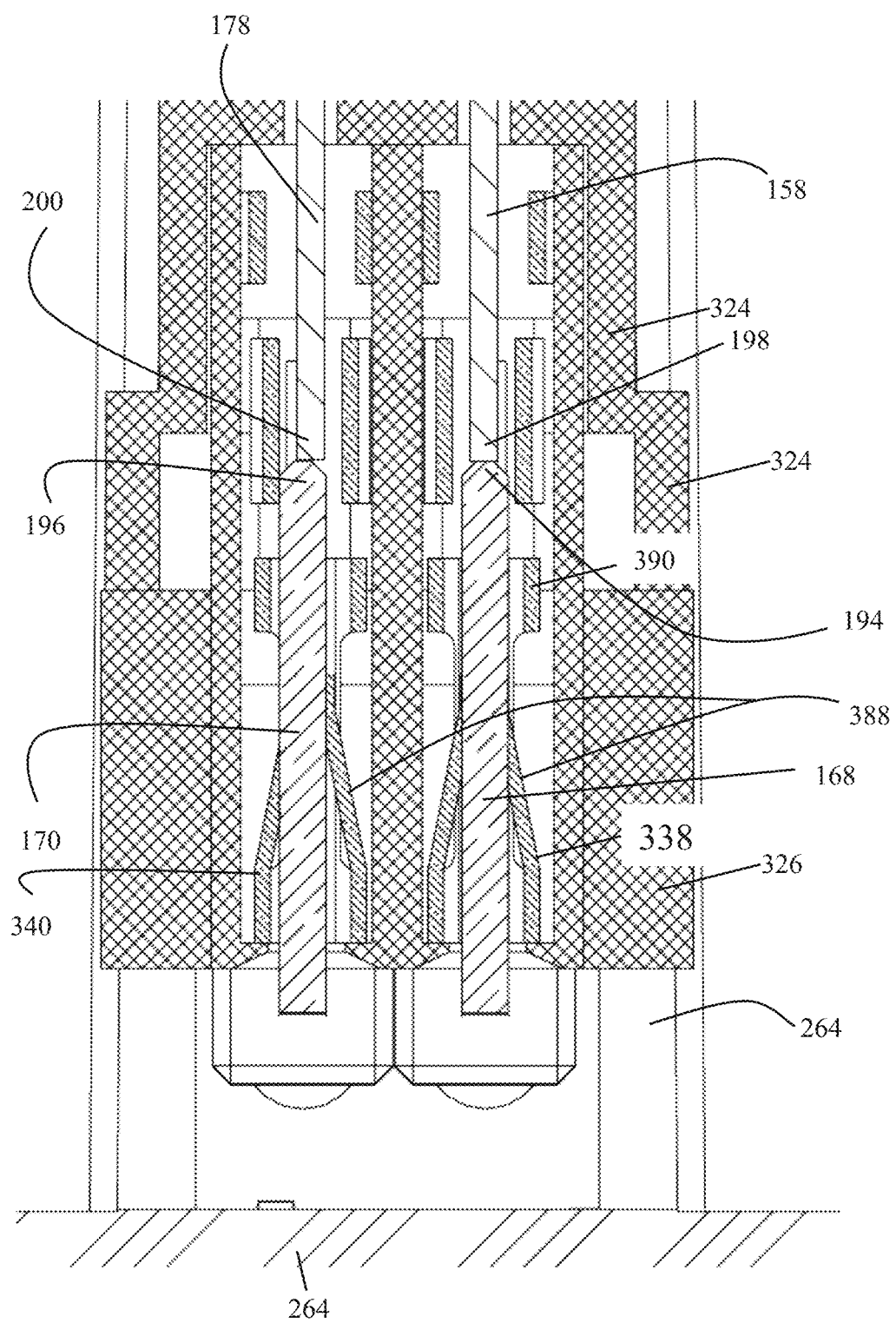
Figure 13D:
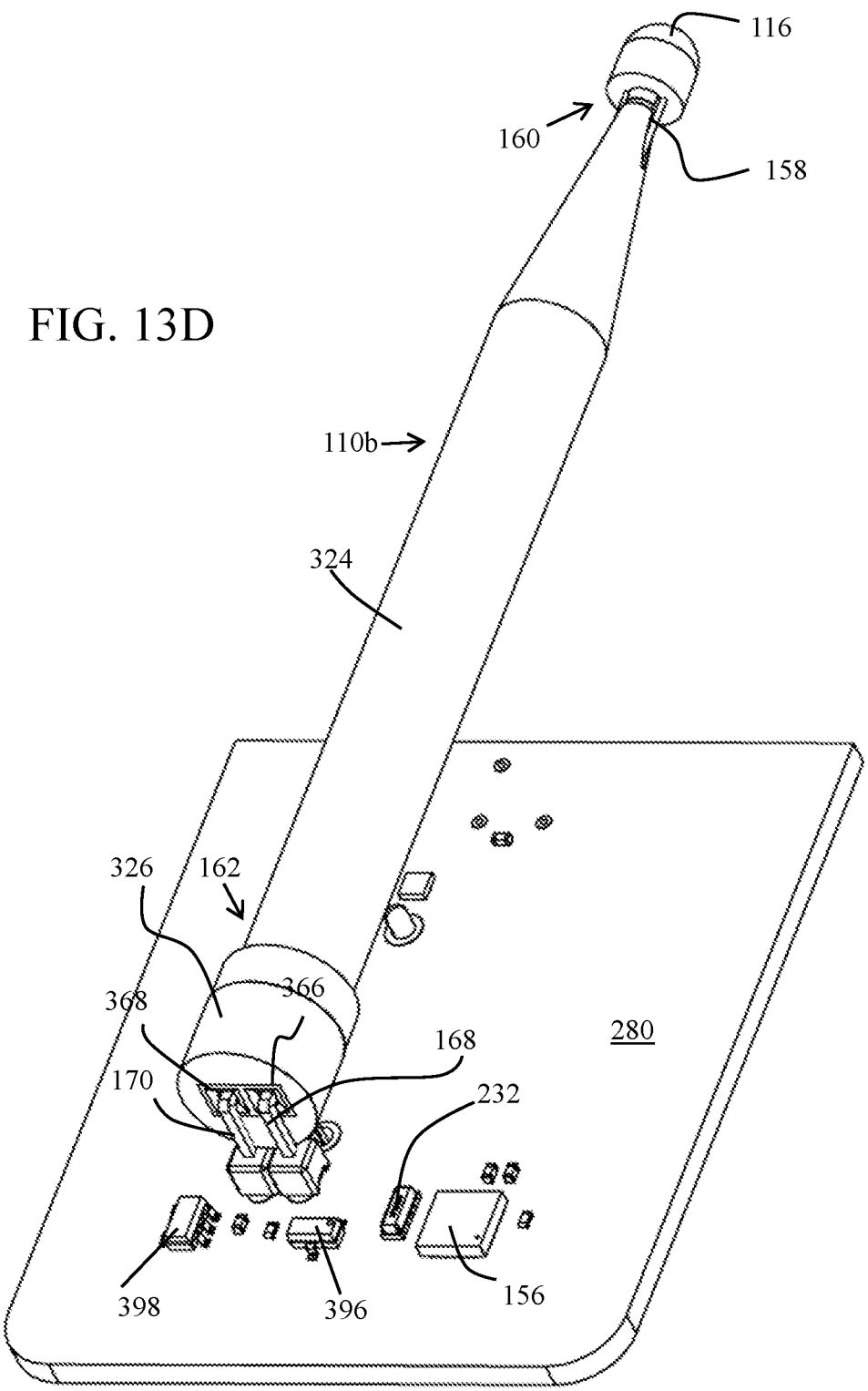
Figure 13E:
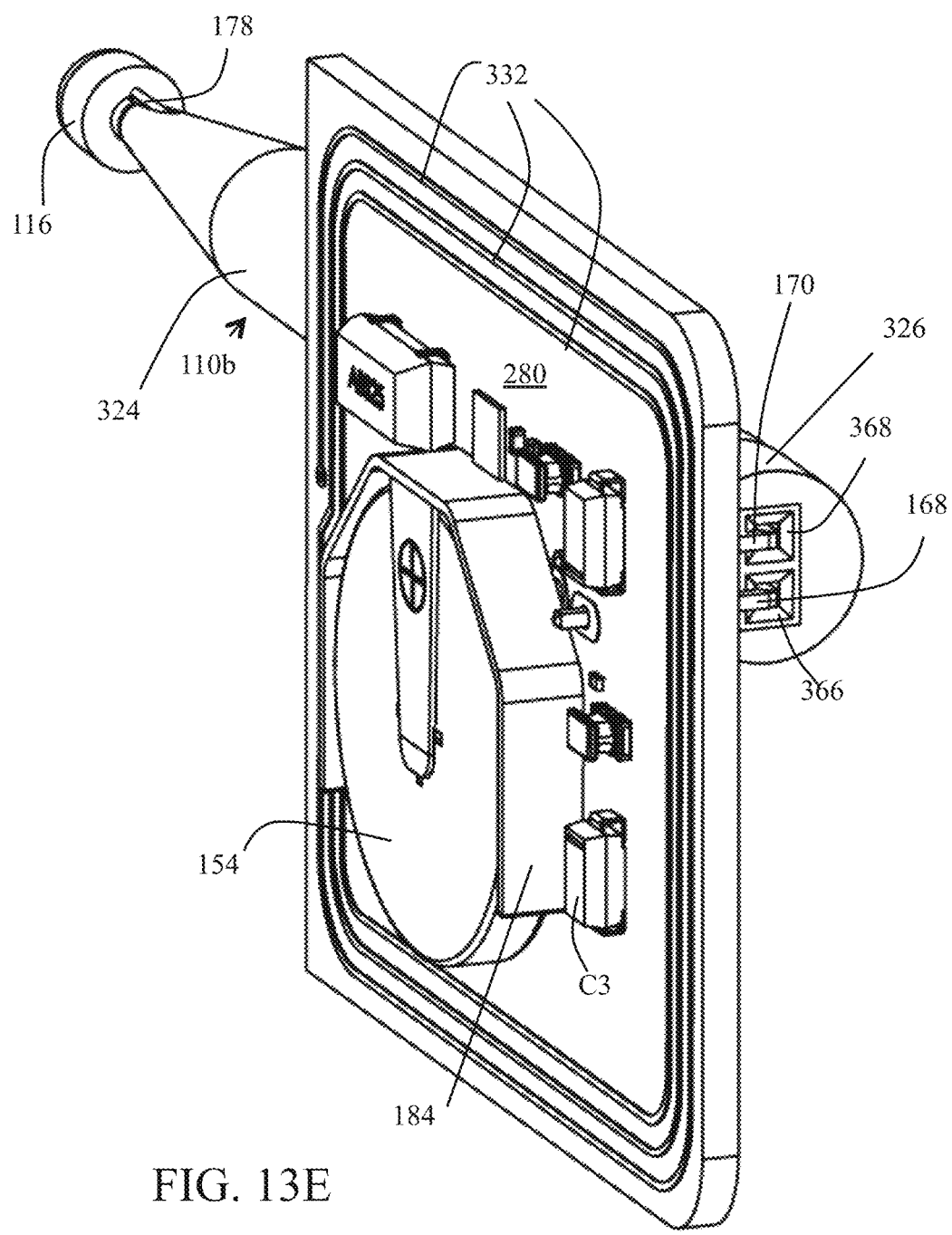
Figure 13F:
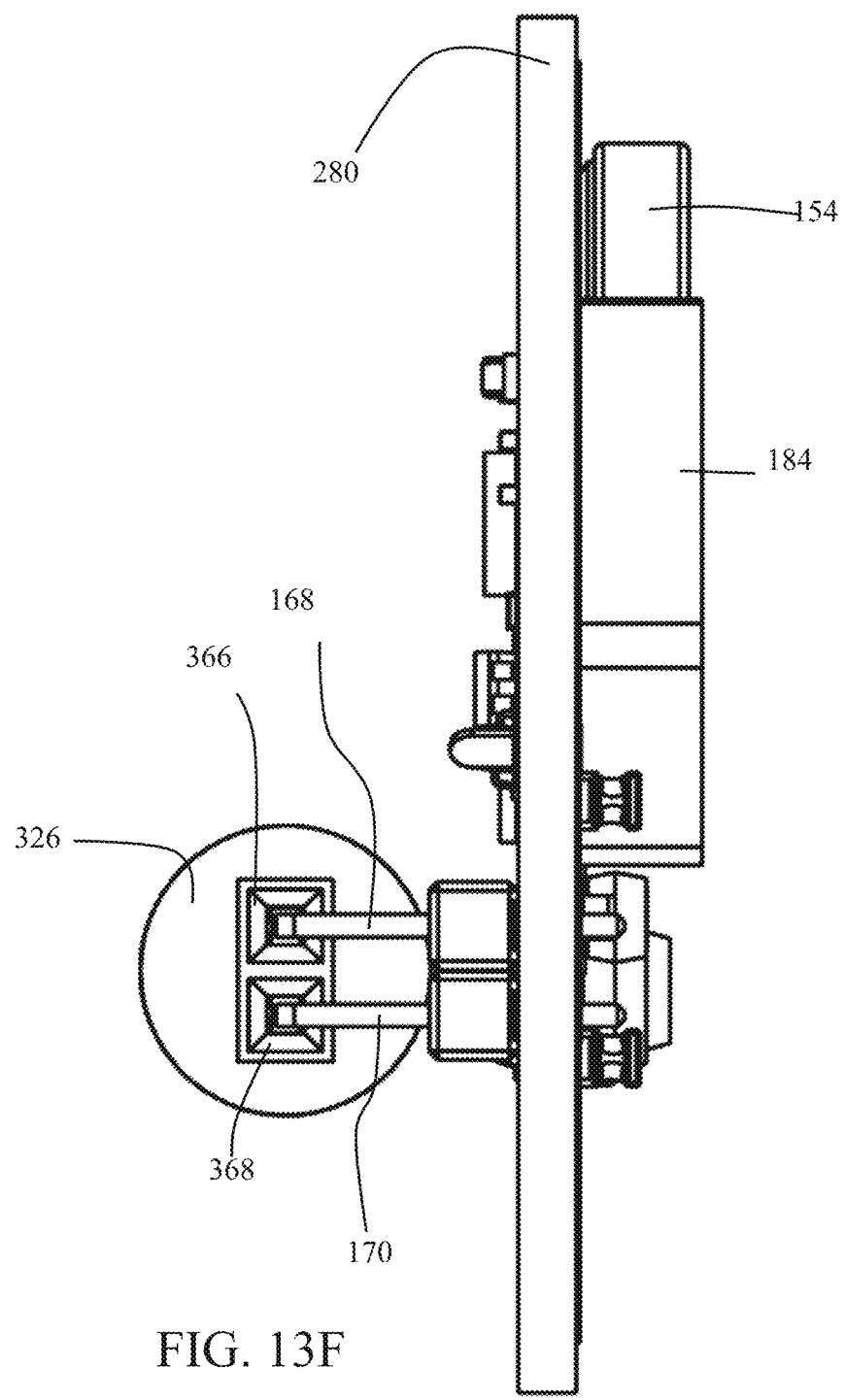
Figure 13I:
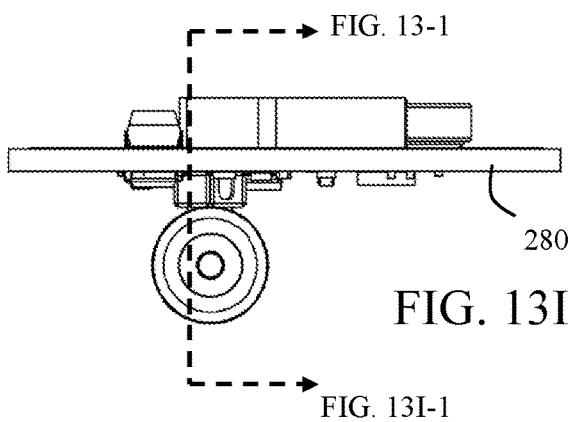
Figures 1, 13I:
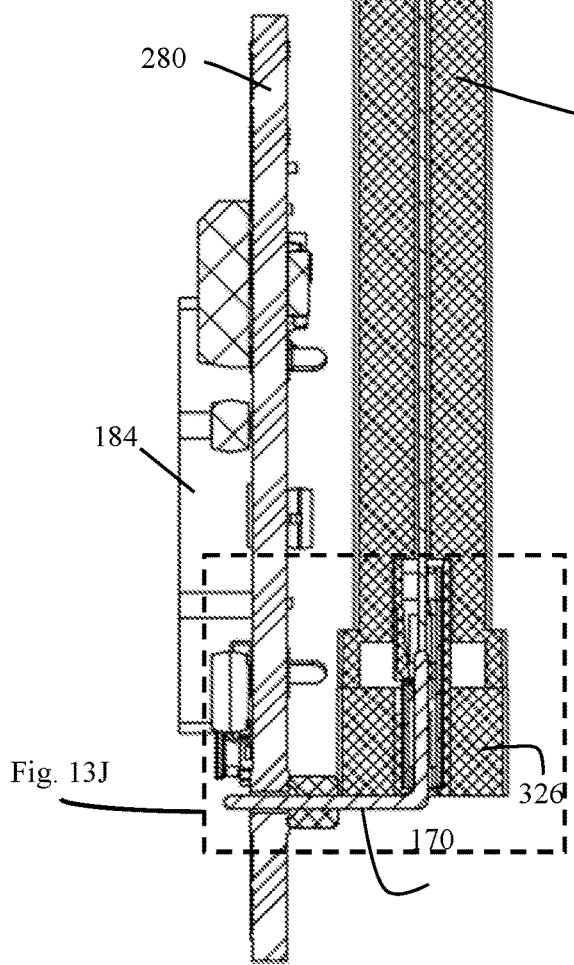
Figure 13J:
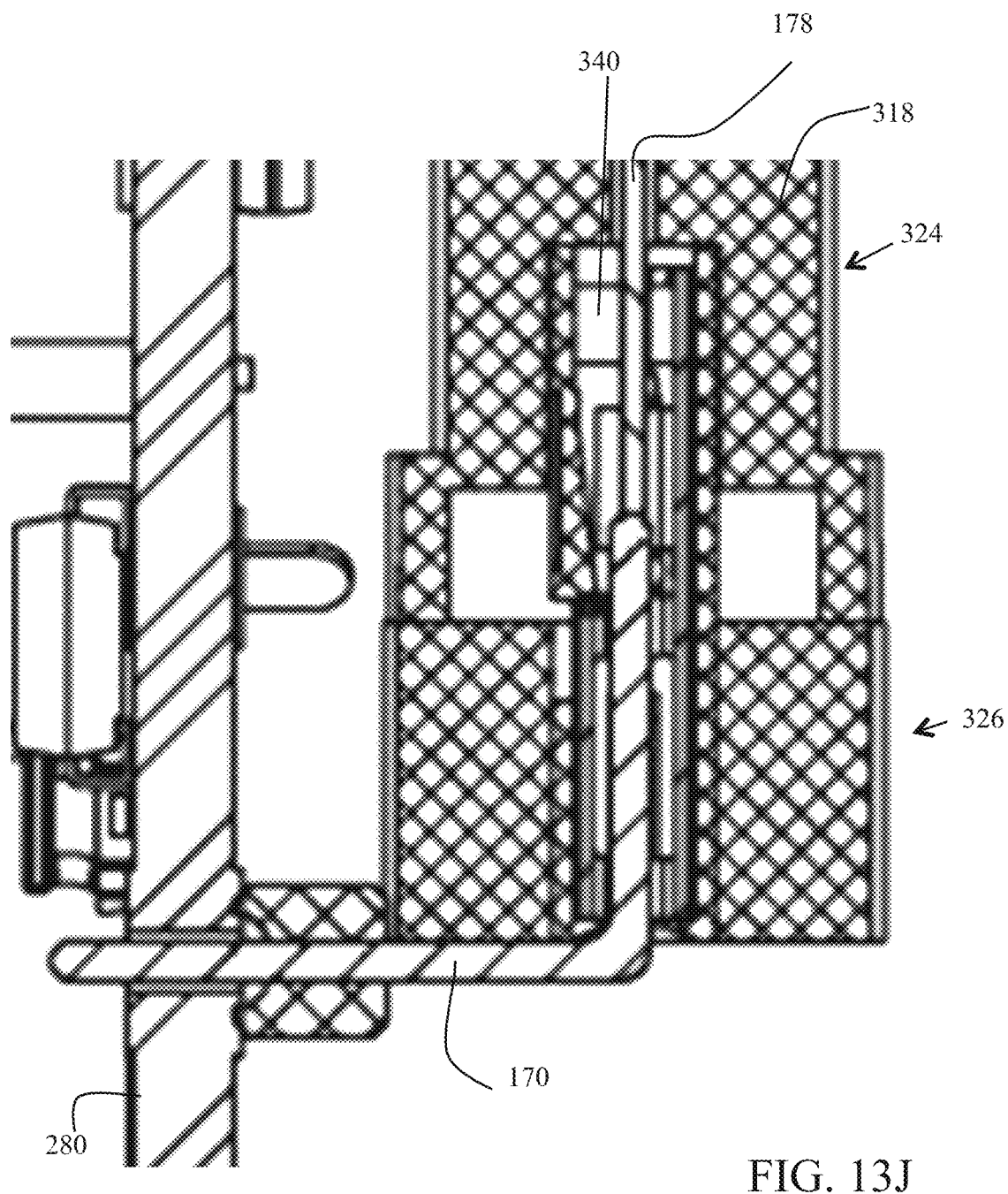
Figure 13K:
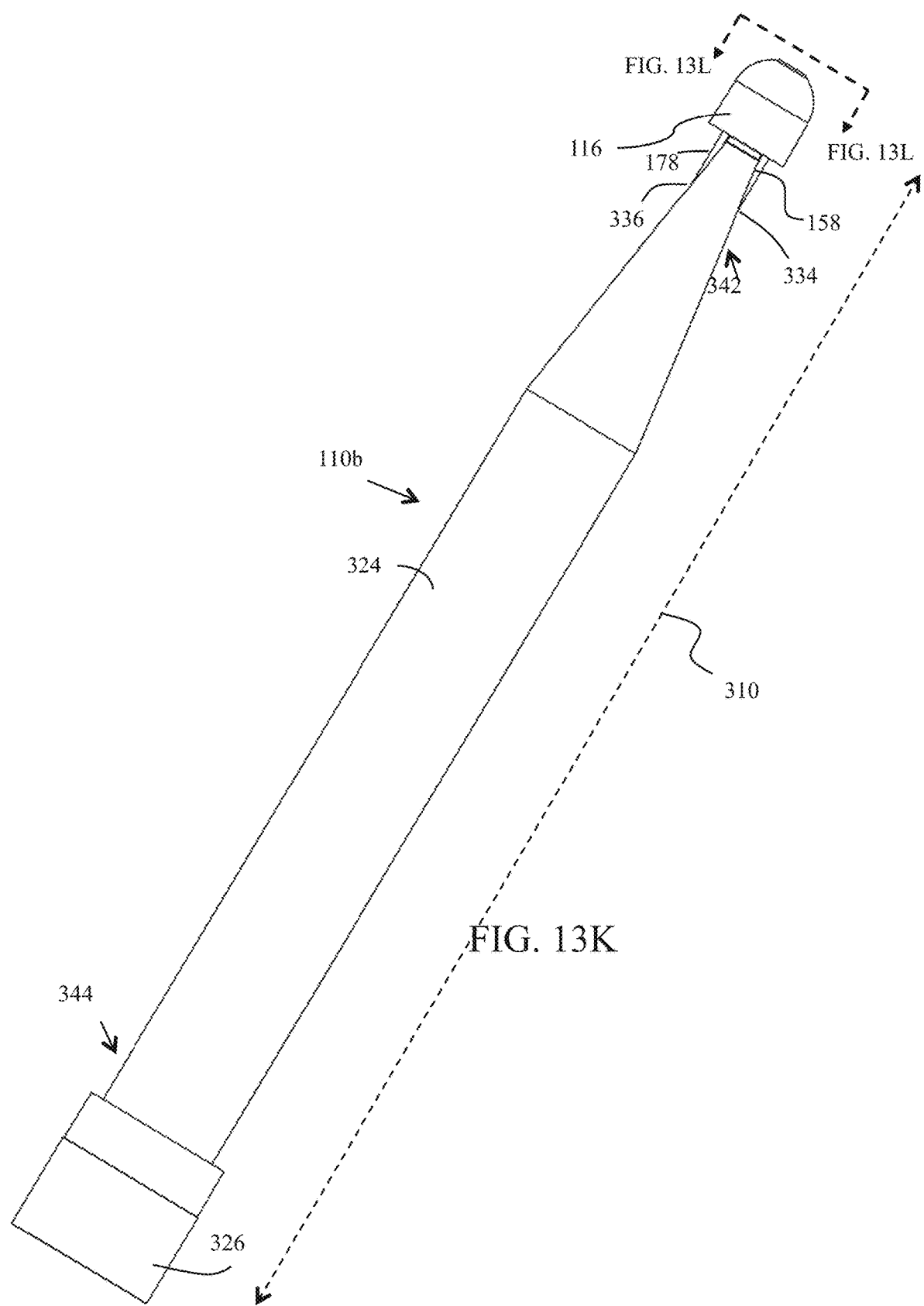
Figures 3, 13L:
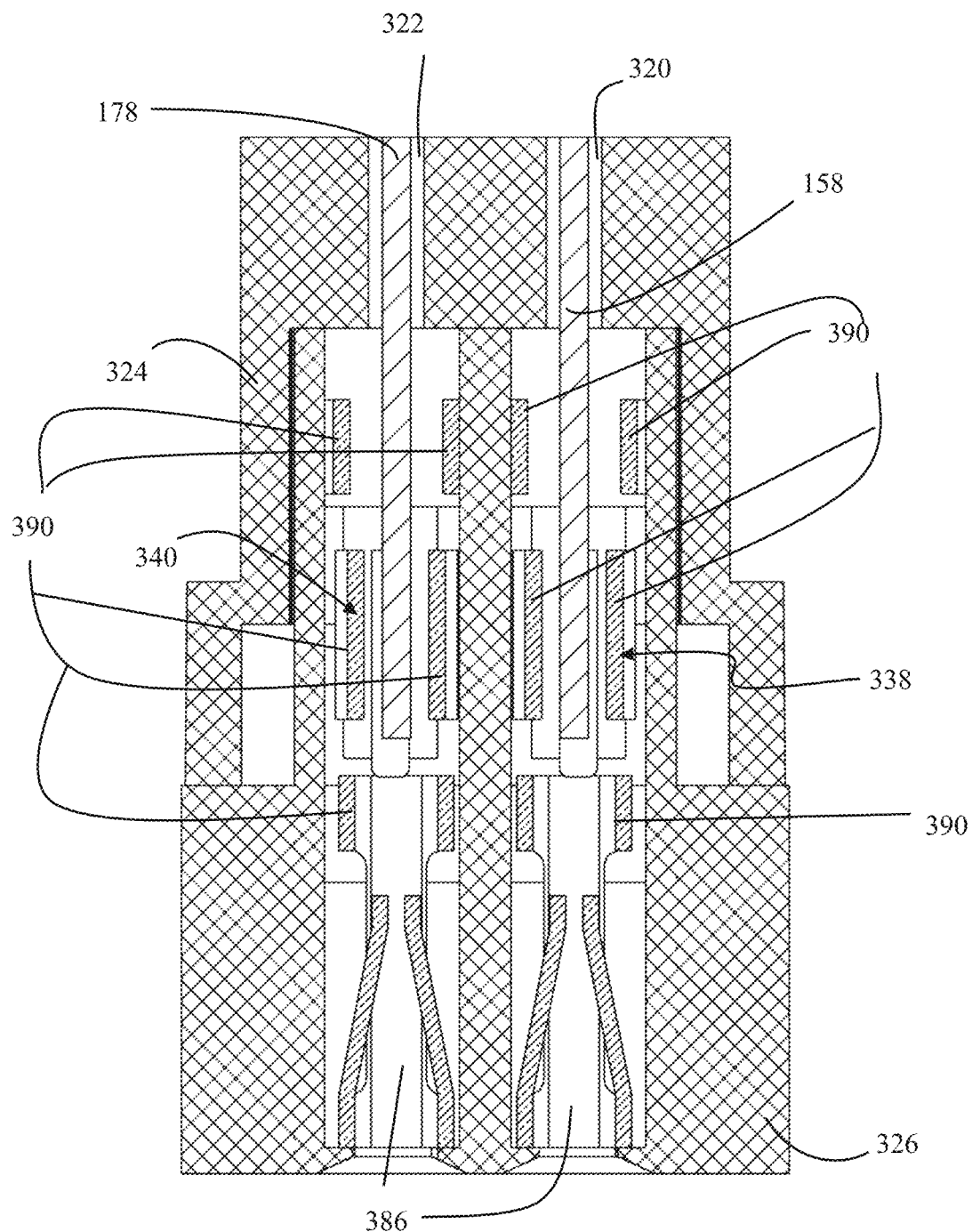
Figure 13M:
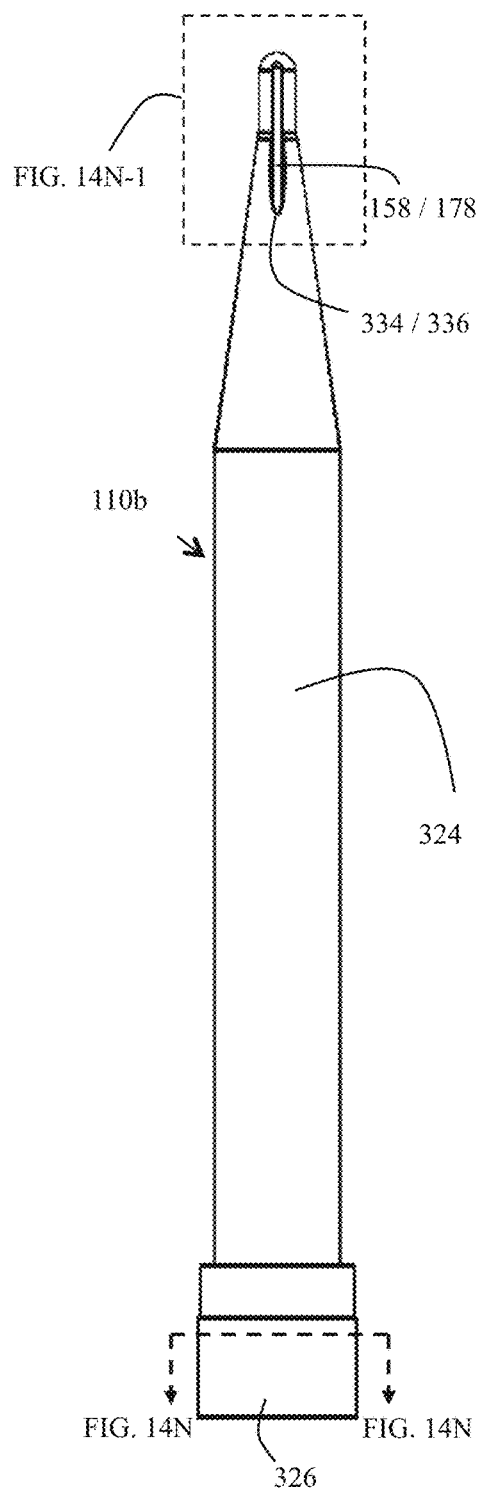
Figures 1, 13N:
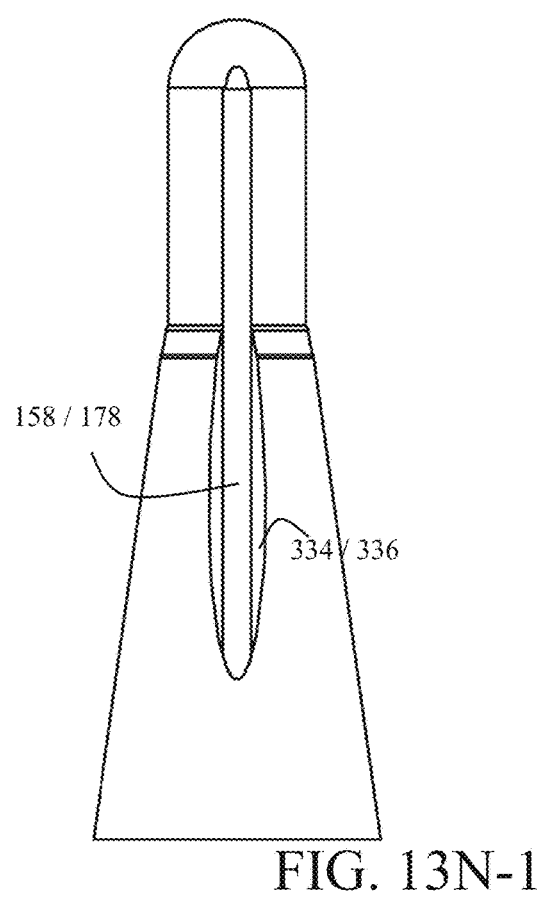
Figure 13N:
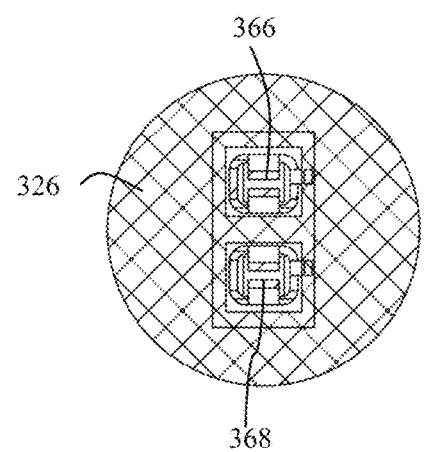
Figure 14A:
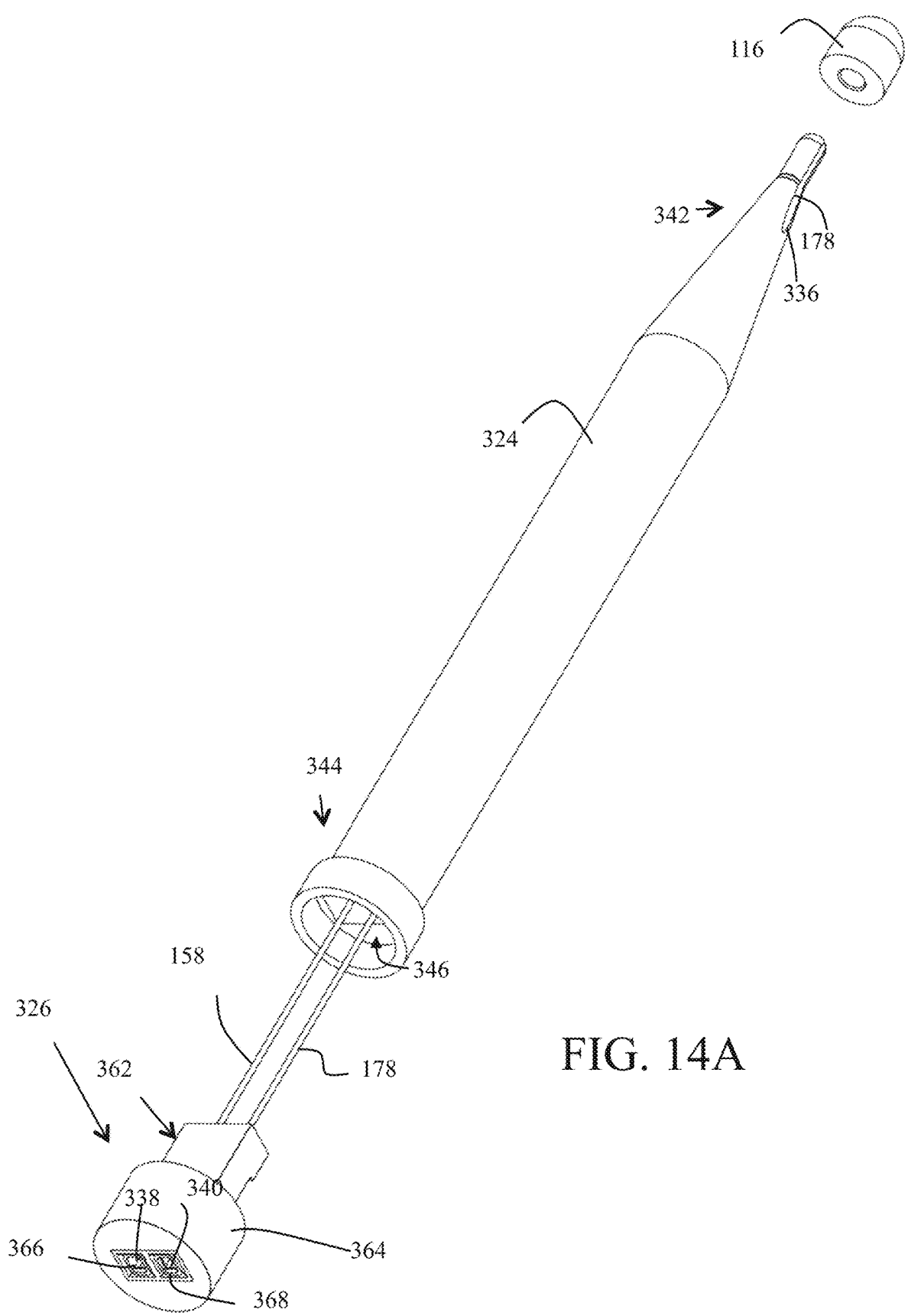
Figure 14B:
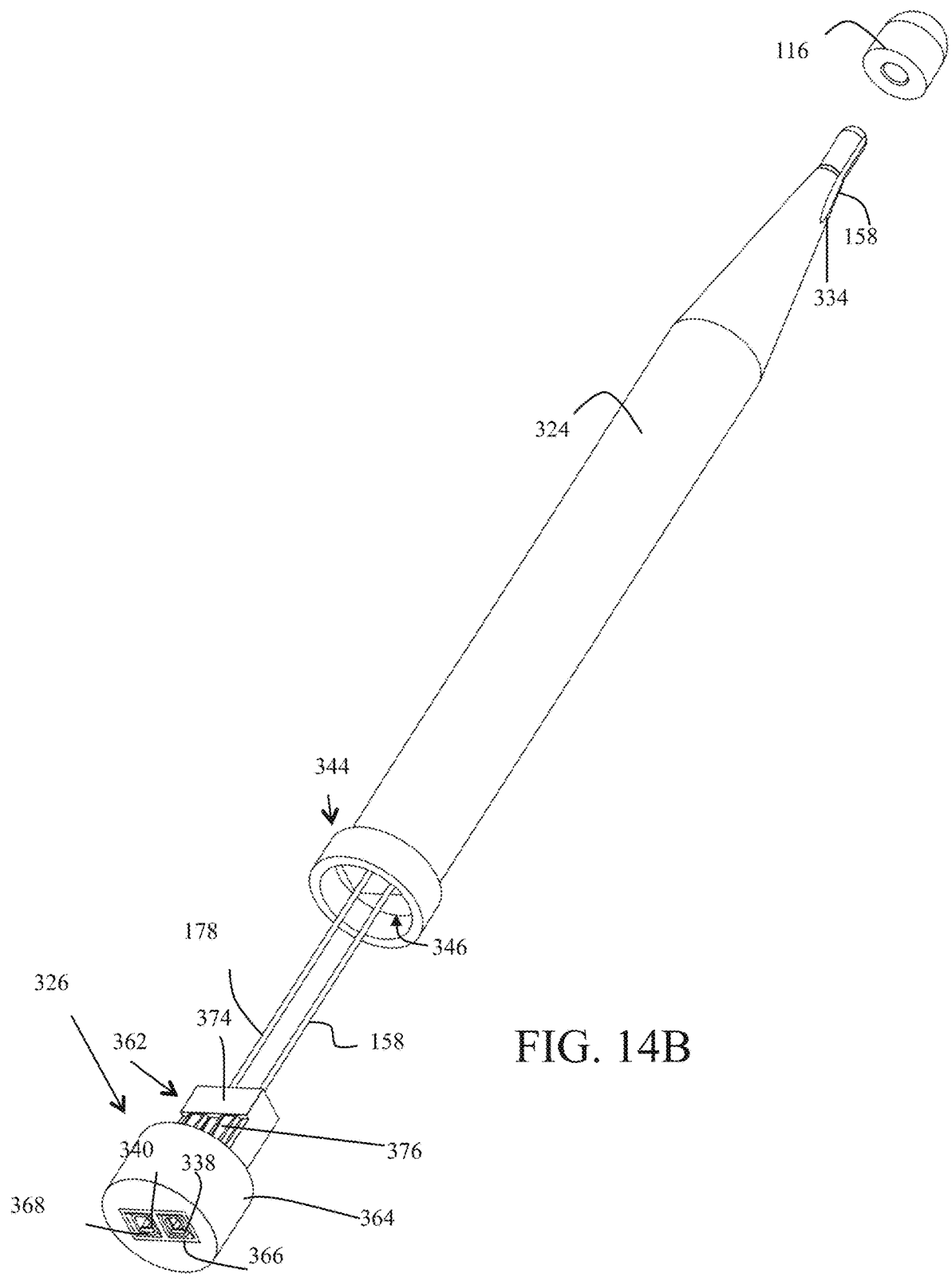
Figures 1, 14C:
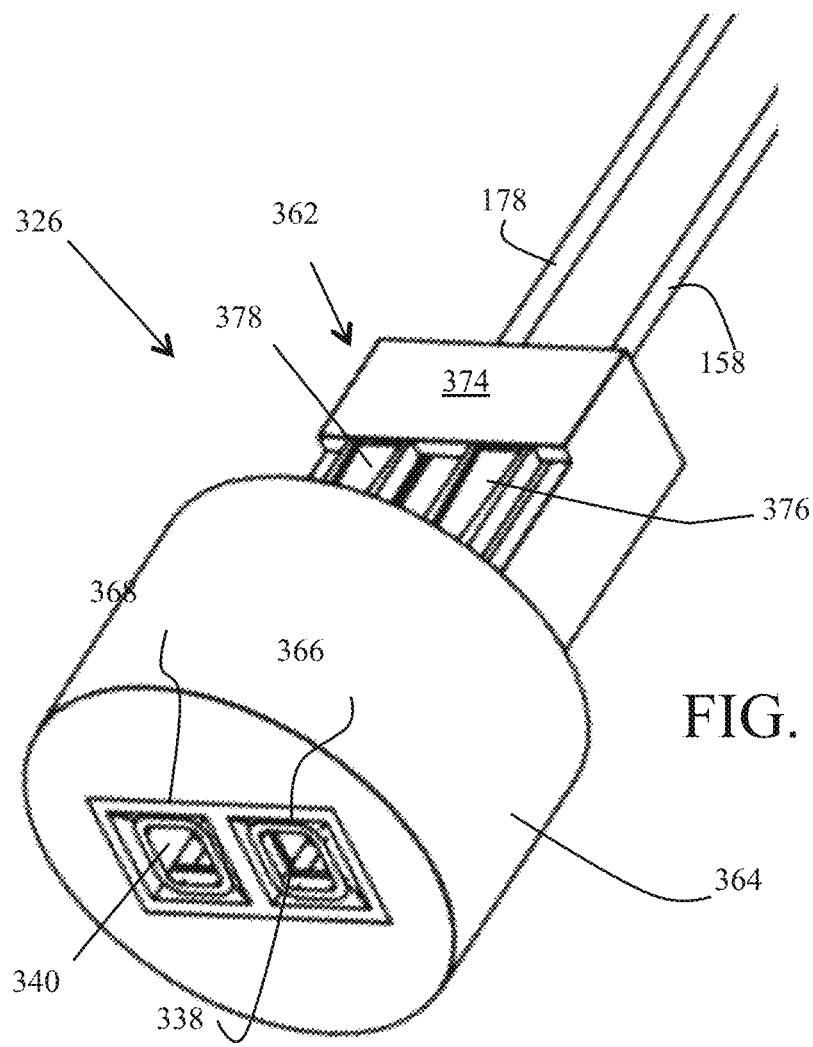
Figures 2, 14C:
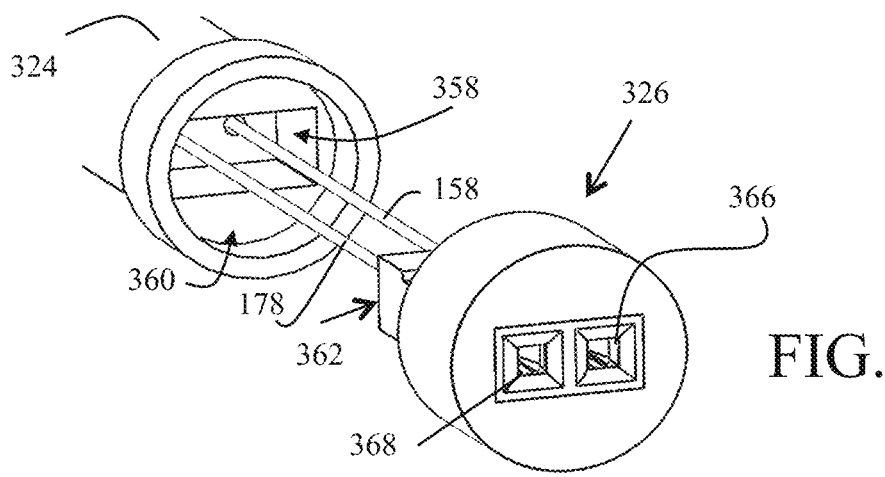

FIGS. 13A to 13N-1 are non-limiting, exemplary illustrations of a housing, handler probes, and recorder (mounted on PCB) shown in FIGS. 10A to 12B in accordance with one or more embodiments of the present invention. More specifically, FIGS. 13A to 13C illustrate fully assembled handler probes 110b and 262a in relation to housing 264 and PCB 280 and recorder 114e while FIGS. 13D to 13J illustrate fully assembled handler probe 110b in relation to PCB 280 and recorder 114e without showing cartridge 102b for clarity. FIGS. 13K to 13N-1 illustrate the various views of a fully assembled handler probe 110b. FIGS. 14A to 14R are non-limiting, exemplary semi-exploded and fully exploded view illustrations of handler probe 110b shown in FIGS. 10A to 13N-1 in accordance with one or more embodiments of the present invention.

In this non-limiting, exemplary embodiment at least one handler probe 110b is associated with recorder 114e while housed within cartridge 102b. In this embodiment as further detailed below, handler probe 110b is comprised of a main piece 324 and a connector-receptacle piece 326, with connector-receptacle 326 being friction-fit within main 324.

Main 324 of handler probe 110b illustrated in FIGS. 10A to 16B has a solid interior 318 (FIG. 13L-1) instead of being hallow as disclosed for handler probes 110a and 262a. Solid interior 318 of main 324 of handler probe 110b includes a first and a second parallel, longitudinally extending linear orifices 320 and 322.

The advantage of having a solid interior 318 in main 324 of handler probe 110b is that it facilitates for easier manufacture and assembly of electrode 158 and 178 within handler probe 110b and further, provides the least amount of movement (wiggle room) for electrodes 158 and 178 so that they do not accidentally disengage from absorbent member 116.

In this non-limiting, exemplary embodiment, electrodes 158 and 178 are no longer bent but are linearly positioned within orifices 320 and 322. In fact, electrodes 158 and 170 extend straight through lateral upper openings 334 and 336 and lower openings 314 and 316 (FIG. 14E) of the orifices 320 and 322 at respective first and second ends 342 and 344 of main 324 of handler probe 110b.

Further, hander probe 110b no longer has a non-conductive protective member 180 that was used with handler probe 110a since in this embodiment, electrodes 158 and 170 extend straight through lateral upper openings 334 and 336, and are inserted within absorbent member 116 (FIG. 13L-2). Accordingly, in this embodiment, absorbent member 116 directly, physically contacts and caps over electrodes 158 and 178 extending straight out of lateral upper openings 334 and 336 of first end 342 of main 324 of handler probe 110b.

Figure 14D:
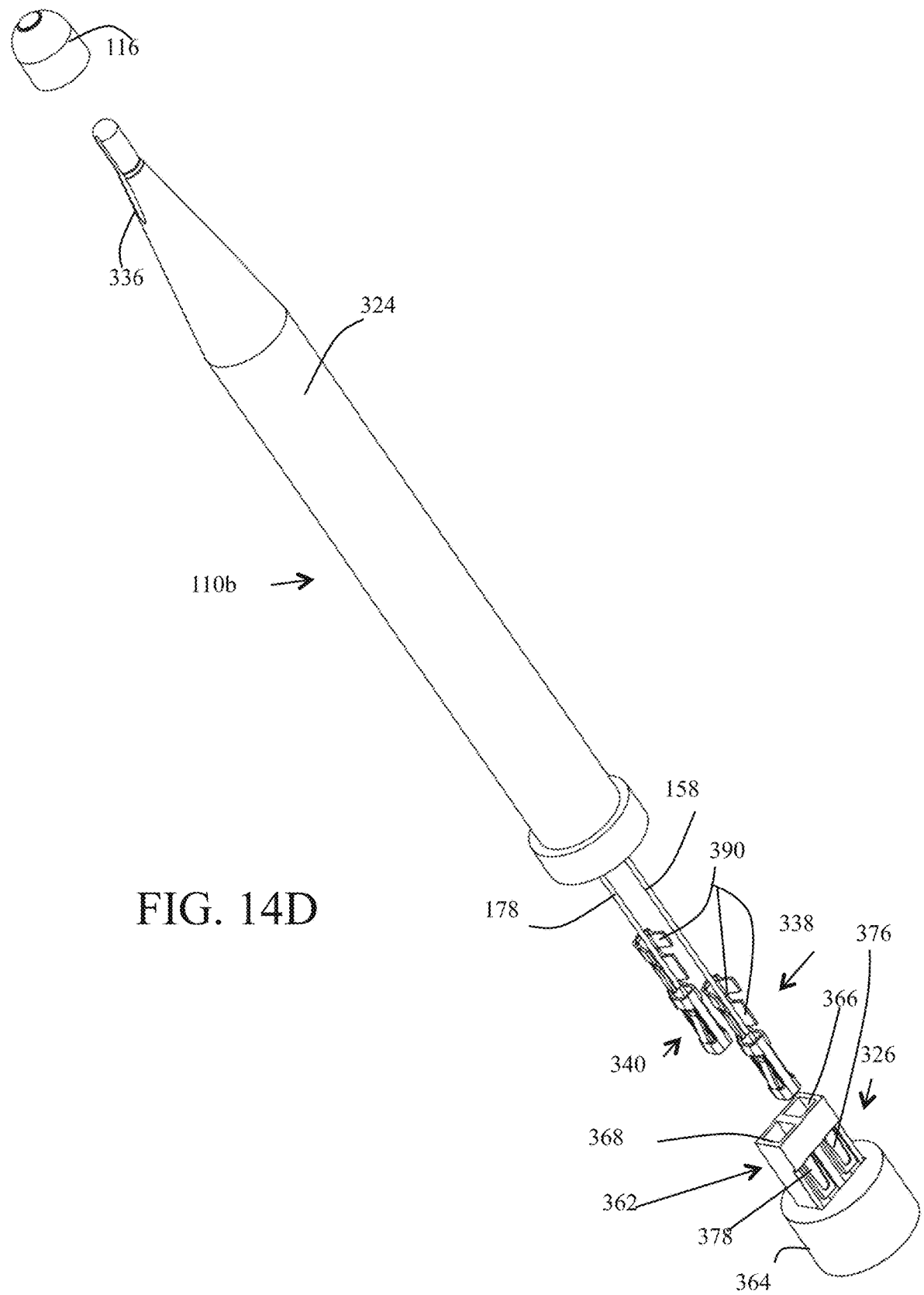
Figure 14F:
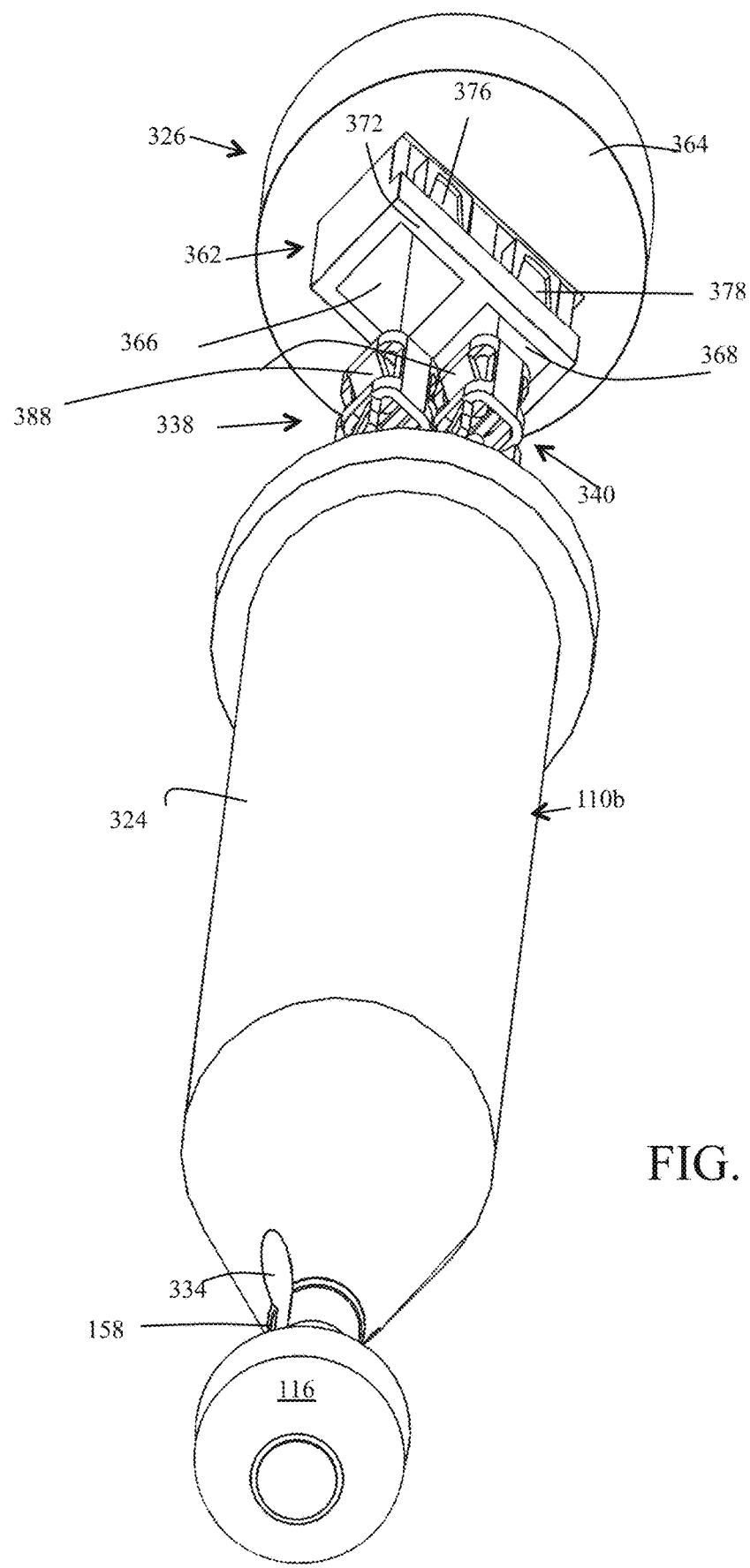
Figure 14G:
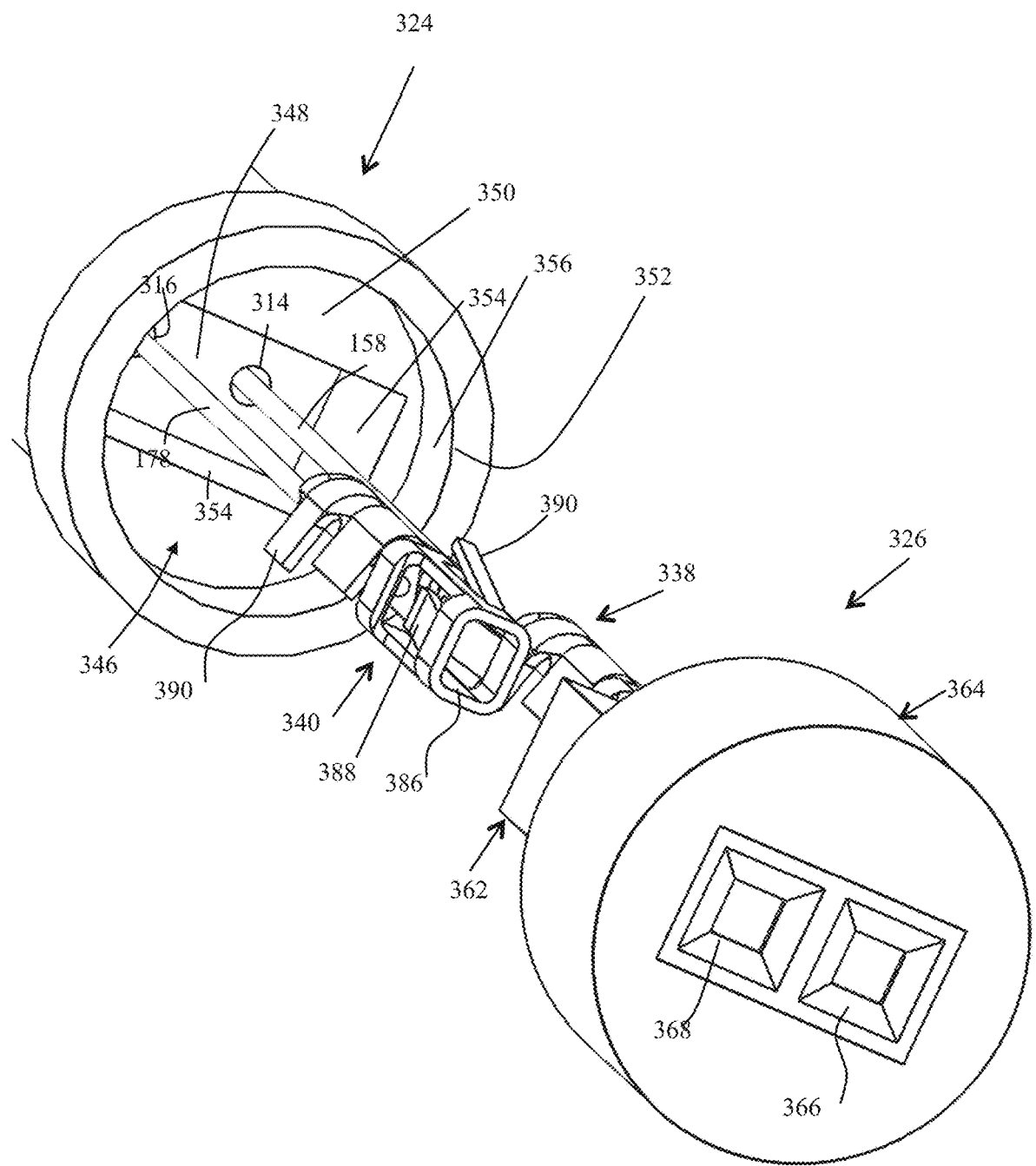
Figure 14J:
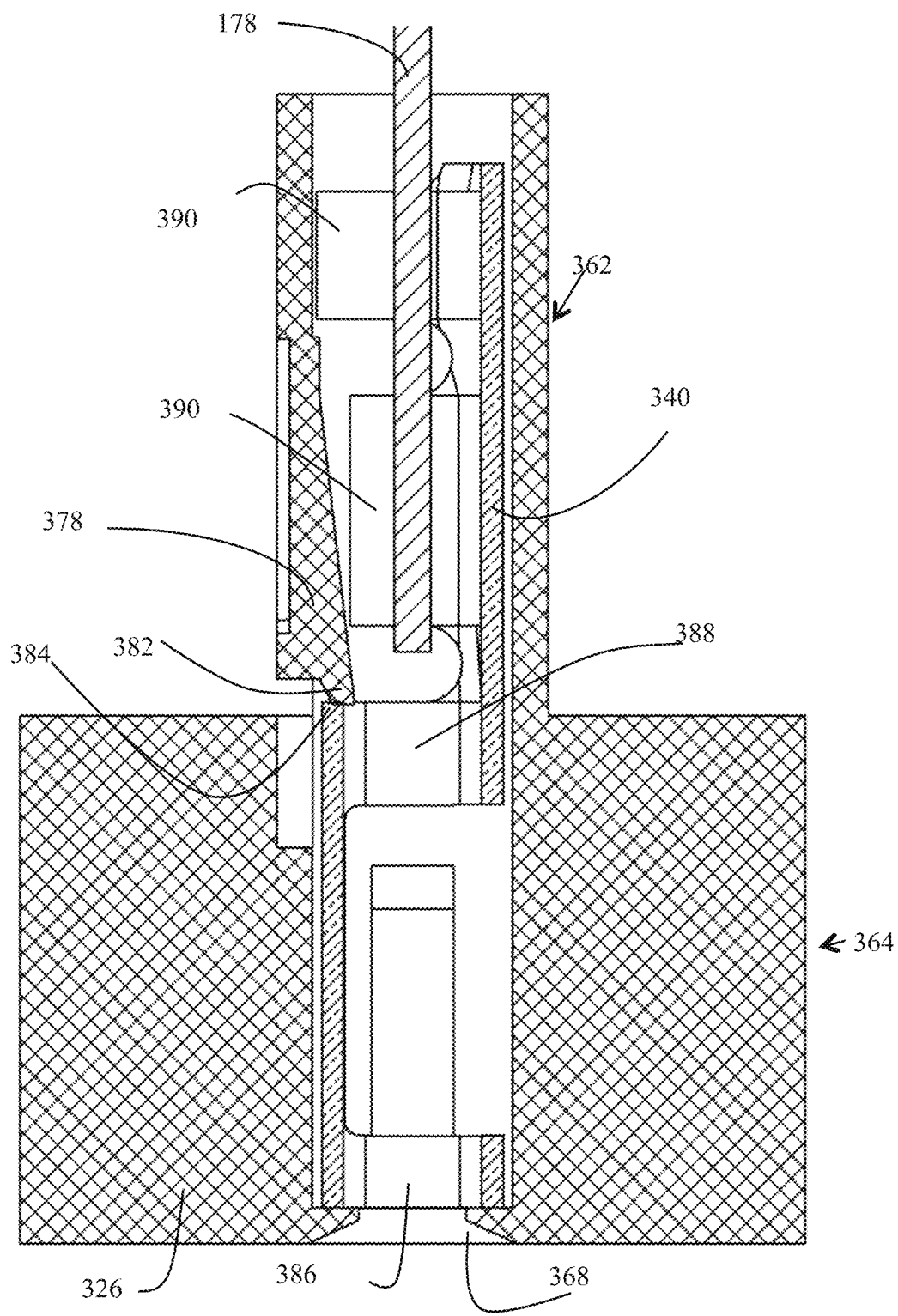
Figures 1, 2, 3, 14K:
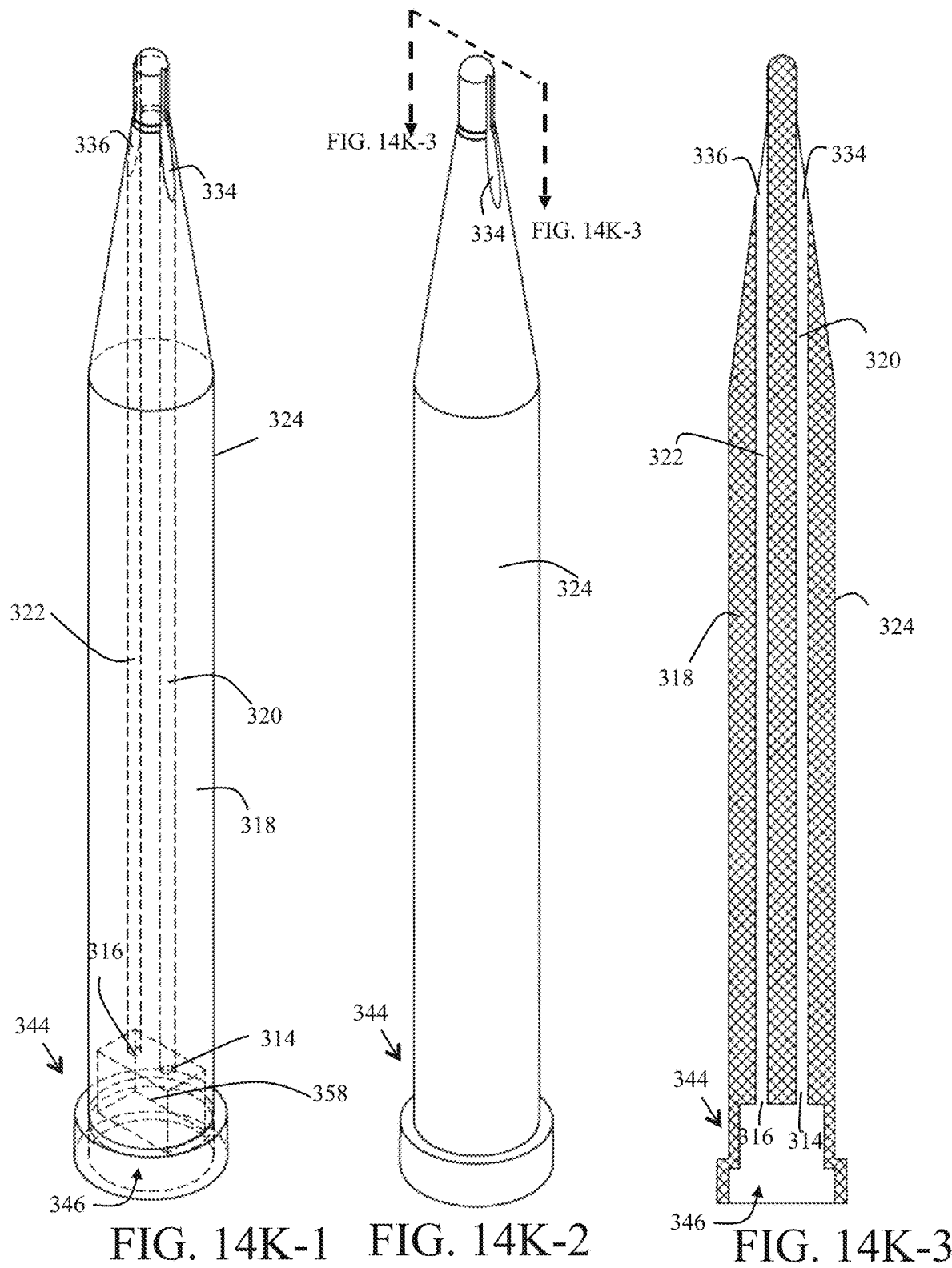
Figure 14L:
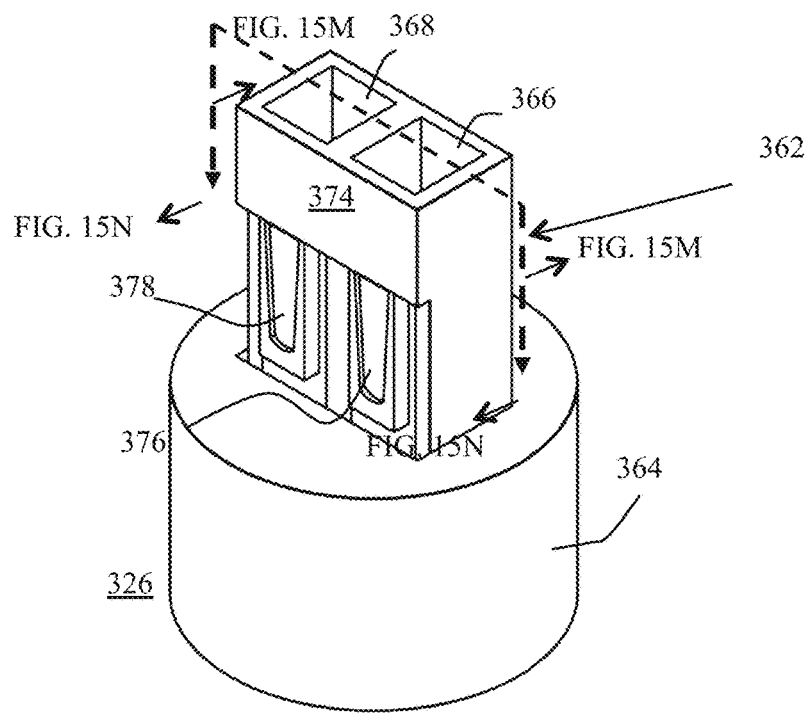
Figures 14M, 14N:
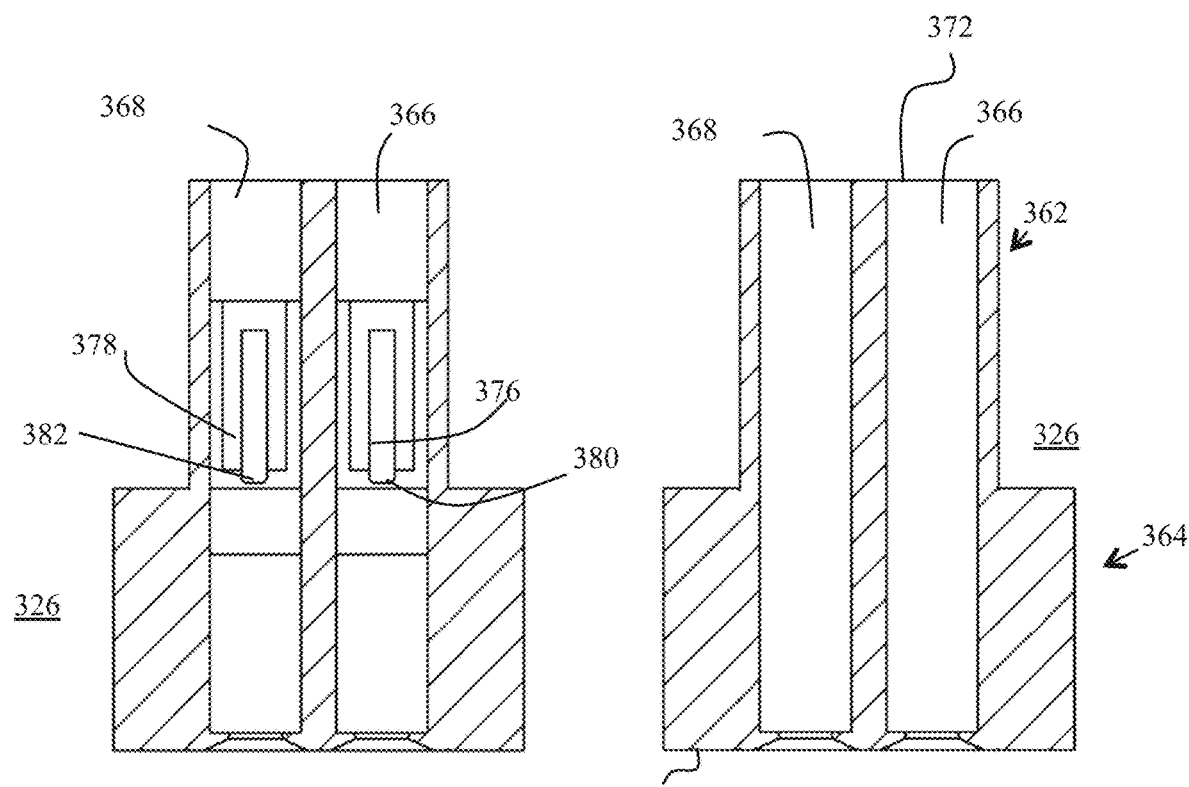
Figure 14O:
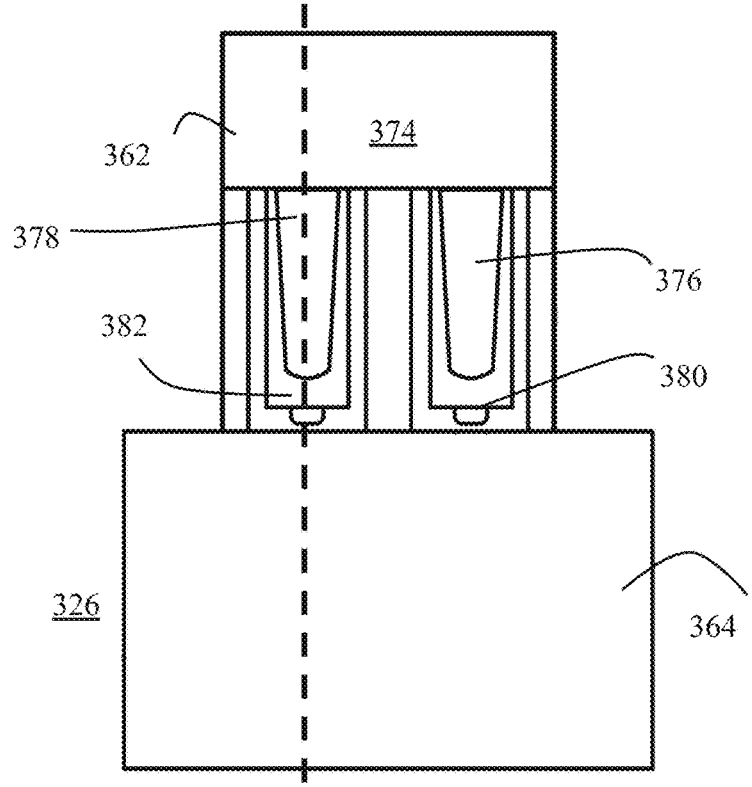
Figure 14P:
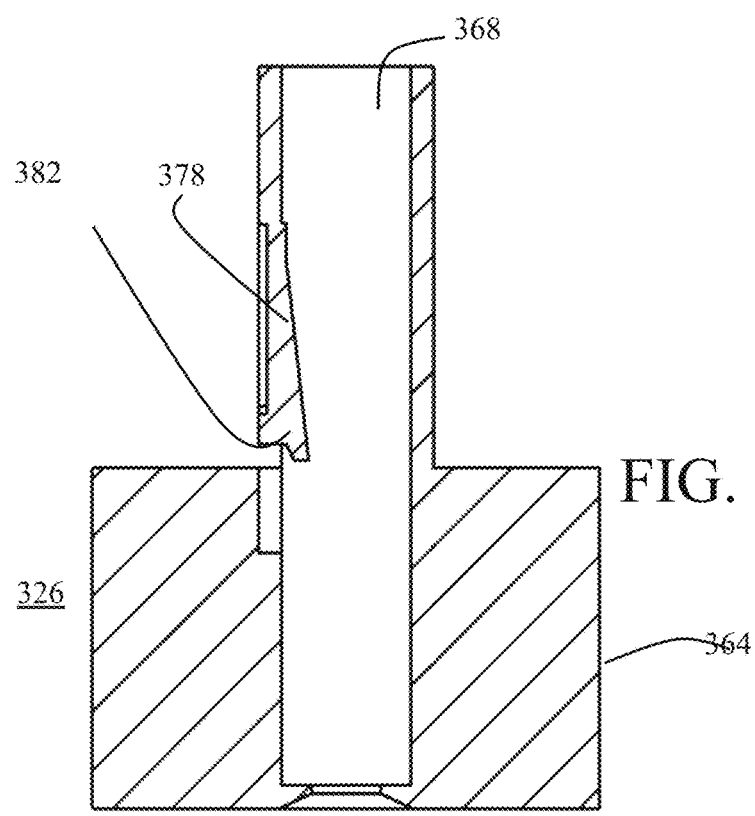
Figures 14Q, 14R, 15R:
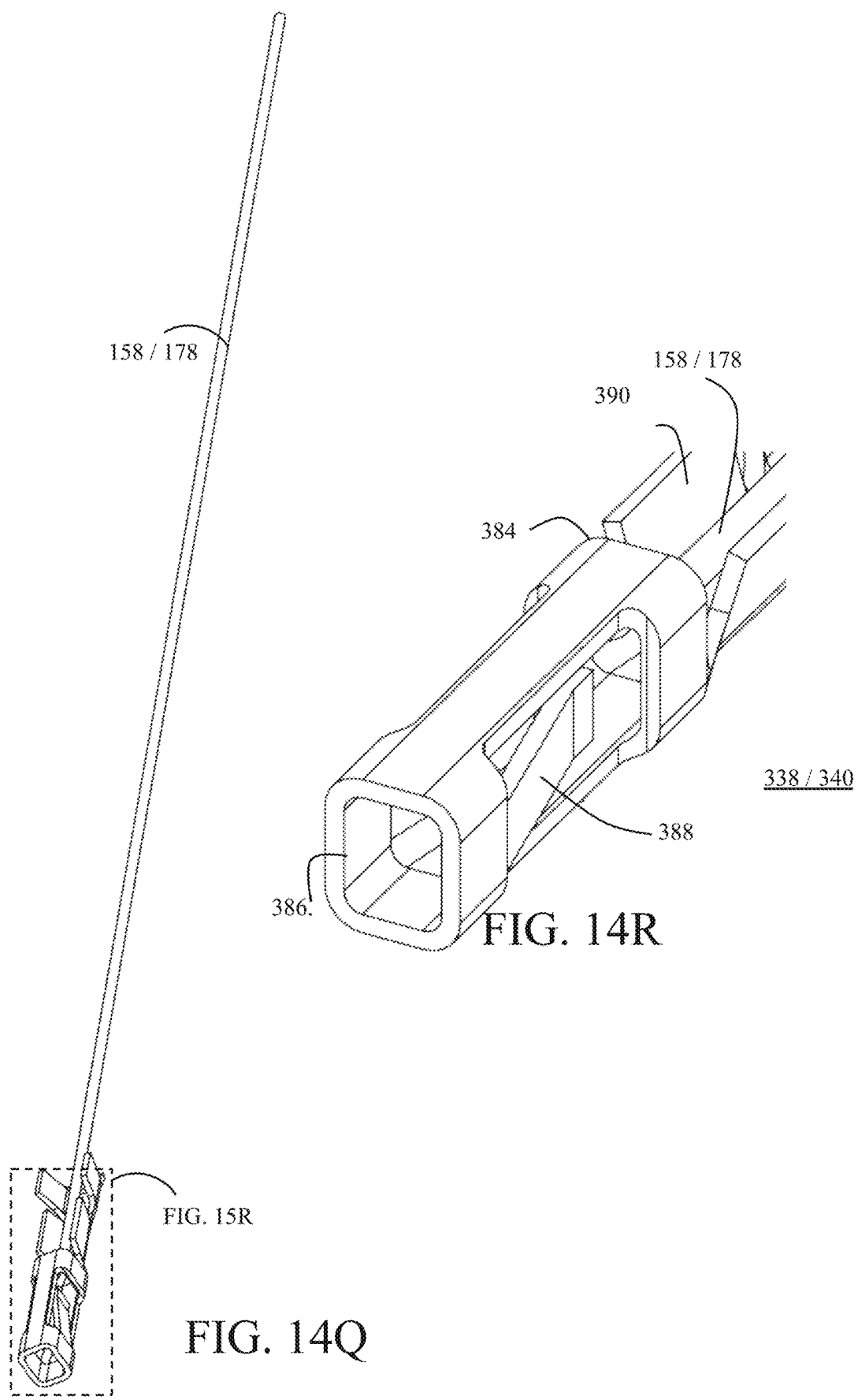

At second end 344, electrodes 158 and 178 extending straight out of lower openings 314 and 316 are also no longer bent, but also extend straight, and physically mechanically connected with a pair of identical female crimper-connectors 338 and 340 that receive engagement pin 168 and 170 from PCB 280 of recorder 114e (best shown in FIGS. 13L and 14D).

Second end 344 of main 324 of hander probe 110b includes lower openings 314 and 316 that lead to a cavity 346 configured to receive and friction-fit connector-receptacle 326. Cavity 346 is comprised of a topography that may be a generally negative topography of a surface of connector-receptacle 326 with which cavity 346 is associates. That is, cavity 346 topography may be defined by a plurality of offset surfaces 348, 350, 352 (FIG. 14G) that define raised edges 354, 356, with the offset surfaces and resulting raised edges forming cavity 346.

In this non-limiting, exemplary instance, cavity 346 is comprised of a lower portion 358 (FIG. 14C-2) with generally rectangular configuration and a higher elevation portion 360 of generally cylindrical configuration that mate with connector-receptacle 326. Connector-receptacle 326 is comprised of a first portion 362 (generally rectangular) that friction-fits within lower portion 358 of cavity 346, and second portion 364 (generally a cylindrical-disc), a general upper part of which friction-fits within higher elevation portion 360 of cavity 346.

Connector-receptacle 326 is further comprised of a first and second through-openings 366 and 368 (FIG. 14N) that are oriented parallel and longitudinally extend from bottom side 370 of second portion 364 and top end 372 of first portion 362. As further detailed below, female crimper-connectors 338 and 340 are housed within through-openings 366 and 368. Accordingly, through-openings 366 and 368 are commensurately configured to correspond with the general shape of female crimper-connectors 338 and 340.

First portion 362 further includes identical locking tabs 376 and 378 (FIG. 14M) on side 374 of first portion 362 of connector-receptacle 326. Locking tabs 376 and 378 include engagement ends 380 and 382 that engage a side 384 (FIG. 14J) of female crimper-connectors 338 and 340 to lock in female crimper-connectors 338 and 340 within through-openings 366 and 368. Accordingly, engagement pins 168 and 170 from PCB 280 are inserted within and form a mechanical contact with engagement portions 386 and 388 (best shown in FIG. 14R) of female crimper-connectors 338 and 340. As best shown in FIG. 13C, engagement pins 168 and 170 also contact ends 198 and 200 of electrodes 158 and 178 while securely housed within through-openings 366 and 368. Female crimper-connectors 338 and 340 further include one or more sets of crimping tabs 390 (FIGS. 13L-3 and 14R) that mechanically crimp ("pinch") electrodes 158 and 178.

Figure 15A:
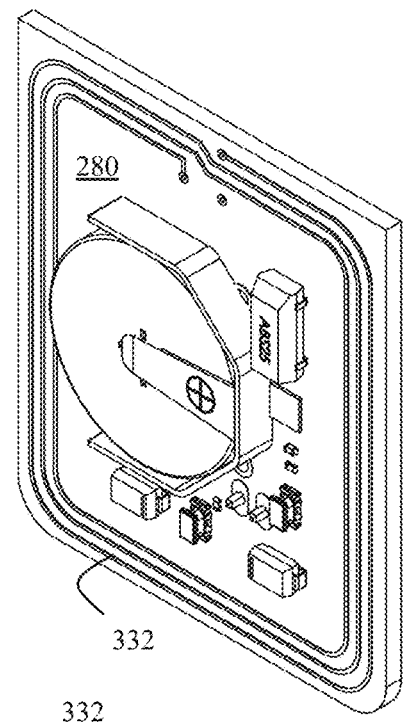
Figure 15B:
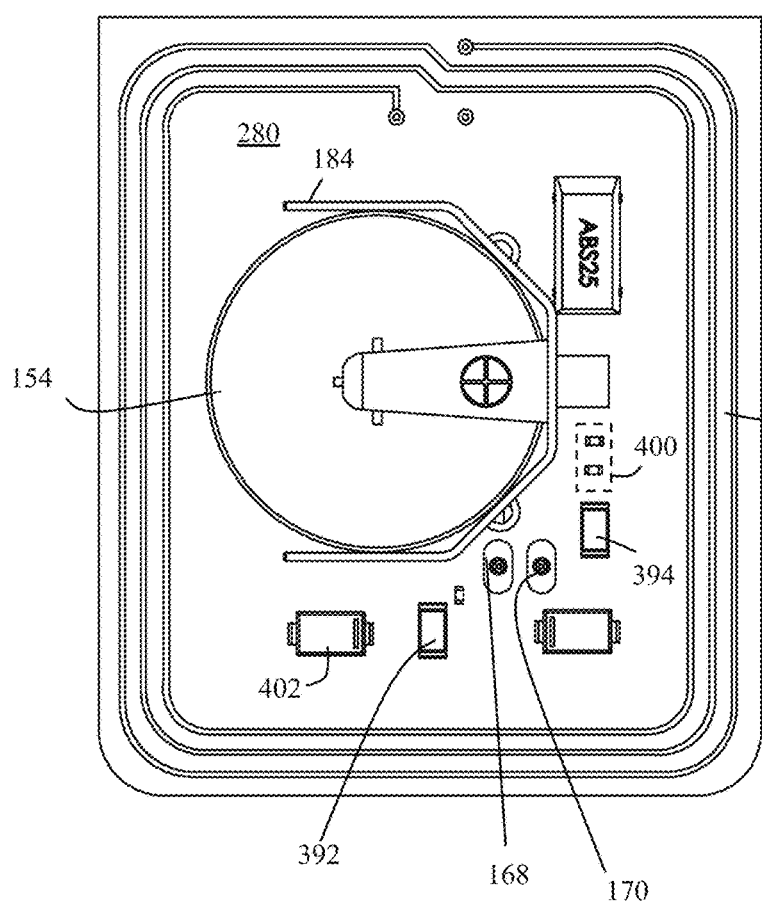
Figure 15C:
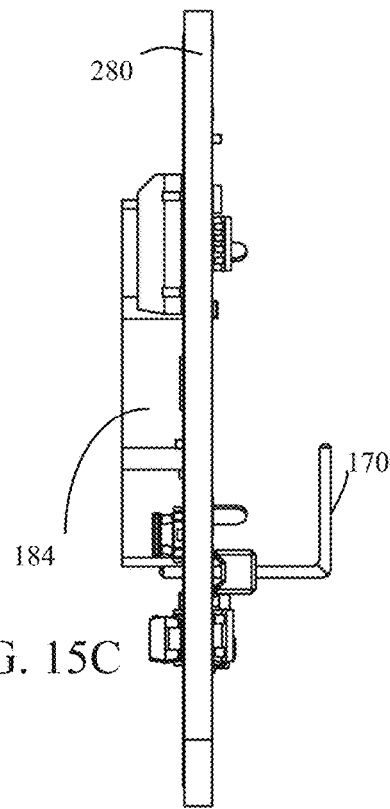
Figure 15D:
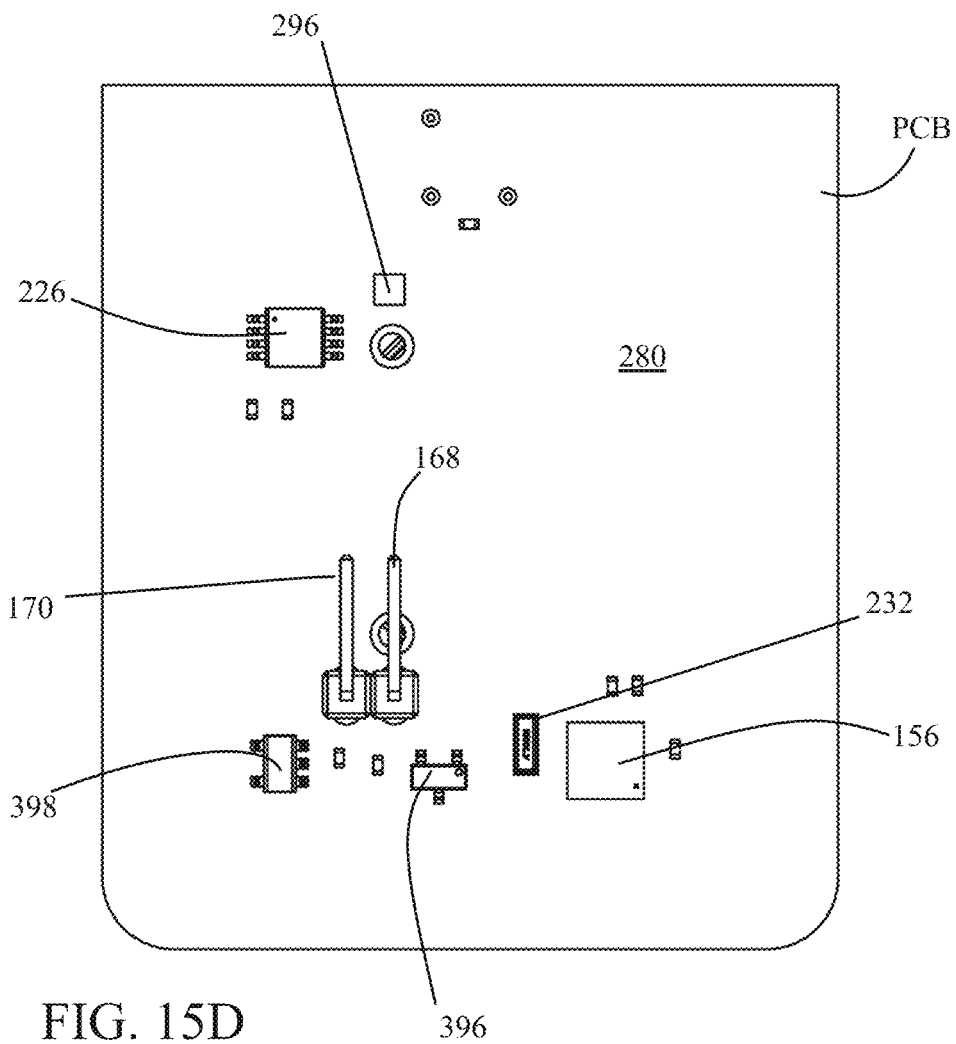
Figure 15E:
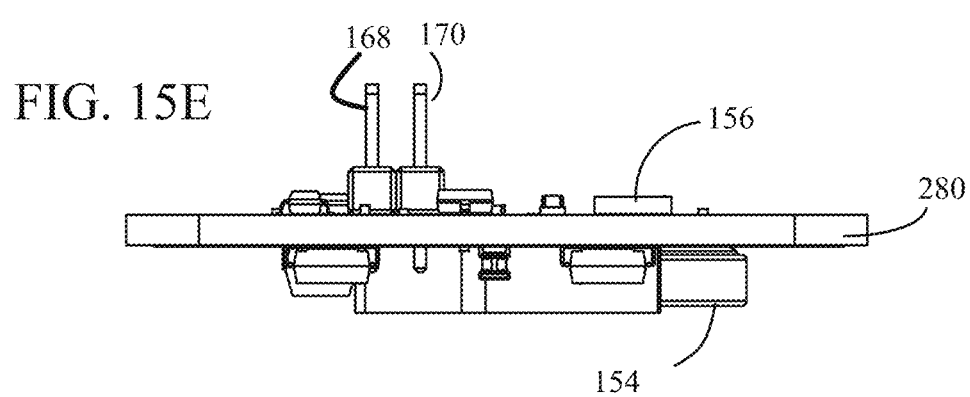

FIGS. 15A to 15E are non-limiting, exemplary illustrations of a non-limiting, exemplary Printed Circuit Board (PCB) of a recorder device in accordance with one or more embodiments of the present invention. As illustrated, in this non-limiting, exemplary embodiment, PCB 280 includes a D-NFC antenna 332, one or more signal processing filters 392, 394, and 400 on a first side of PCB 280 (FIG. 15B). PCB 280 further includes an active mode signal generator (e.g., a switch such as a MOSFET) 396, a voltage regulator 398, and a Dynamic-NFC chip 296 (DNFC) on a second side of PCB 280 (FIG. 15D). Further included are various other electronic components that constitute recorder 114e, details of which are provided below in relation to electrical schematic circuit diagram in relation to FIGS. 16A and 16B.

Figure 16B:
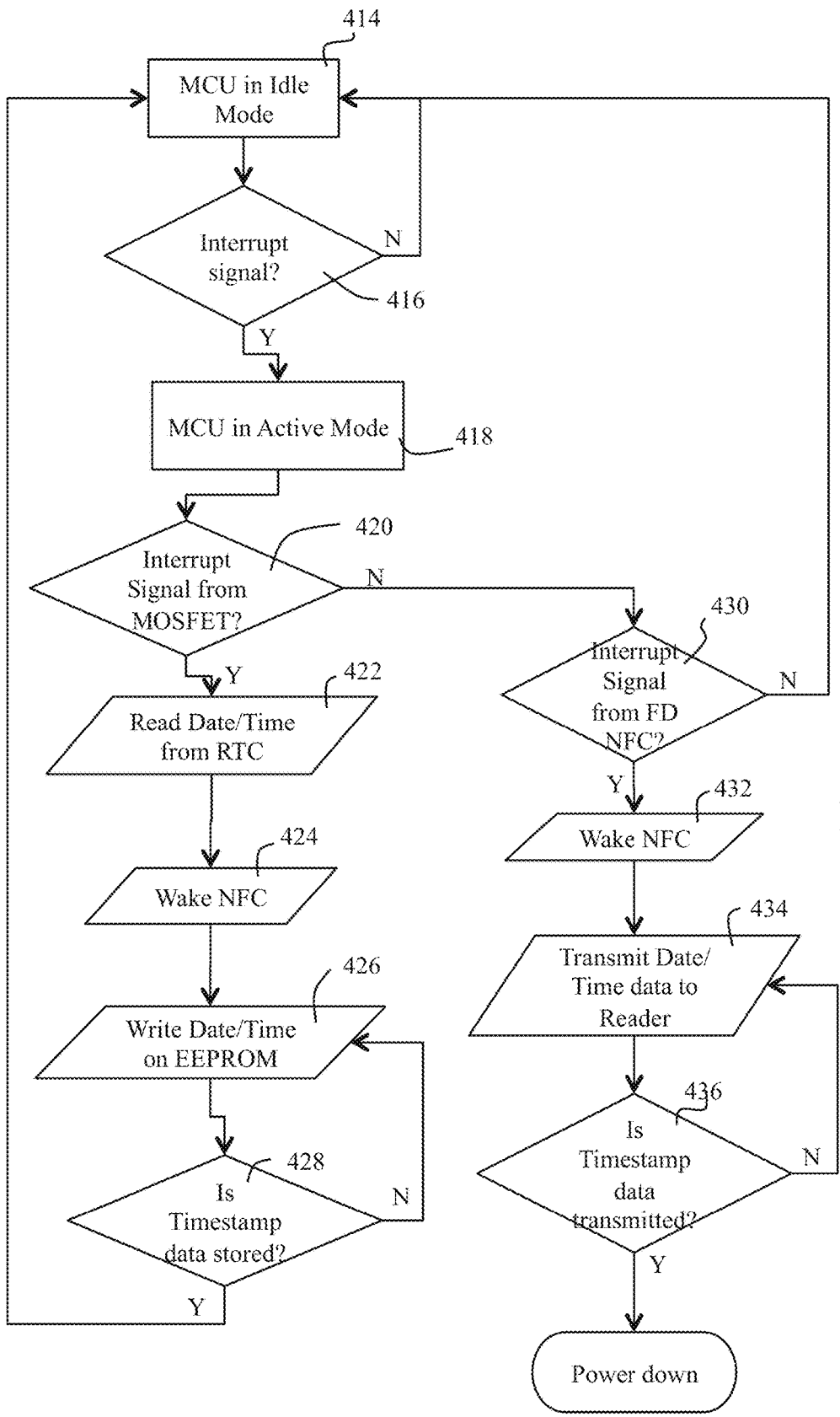

FIG. 16A is a non-limiting, exemplary illustration of an electrical schematic circuit diagram of a probe 110b and recorder 114e combination shown in FIGS. 10A to 15E in accordance with one or more embodiments of the present invention. FIG. 16B is a non-limiting, exemplary illustration of a flow diagram related to microcontroller unit (MCU) operations shown in FIGS. 10A to 16B in generating and saving of recorded data (e.g., timestamp data) in accordance with one or more embodiments of the present invention.

As illustrated in FIG. 16A, fluid sampling device 100b includes handler probe 110b with absorbent member 116. Further included is a pair of electrodes 158 and 178 that are associated with handler probe 110b and recorder device 114e. In this non-limiting, exemplary embodiment an active mode signal generator 396 is used to output an active mode signal to MCU 156 when the pair of electrodes 158 and 178 are bridged by a conductive fluid such as blood.

Recorder 114e further includes microcontroller unit (MCU) 156 that is driven from a non-active mode to an active mode by the active mode signal generated by active mode signal generator 396. Also included is a well known Real Time Clock (RTC) circuit 226 that outputs a timestamp information when instructed by MCU 156, which is stored in a non-volatile memory of DNFC chip 296, and output thereby as detailed in FIG. 16B.

As further illustrated in FIG. 16A, in this non-limiting exemplary embodiment, recorder 114e includes a first signal processing circuitry 400 and a second signal processing circuitry 402. First signal processing circuitry 400 is a signal filtering circuit comprised of a bypass capacitor to facilitate filtering electrical noise comprised of a pair of parallel connected bypass capacitors C3 and C4 having a first end connected to ground GND and a second end connected to power source Vcc and a power input terminal 408 of MCU 156.

The electrical noise filtered by bypass capacitor filter 400 may be caused by any other circuit element (e.g., RTC) of recorder device circuit 114e, creating fluctuations or ripple voltage or current that should be filtered out. The electrical noise (power voltage fluctuations or ripple) may potentially cause a false recording of timestamp data and hence, is filtered by first signal processing filter 400. Accordingly, first signal processing filter 400 is for protection against power voltage and current fluctuations or ripple that may be caused by other circuitry on PCB 280, which may cause a potential false reading and recording of time/date.

Second signal processing circuitry 402 includes identical Electromagnetic (EMI) Interference filters 392 and 394 to facilitate filtering of unwanted electromagnetic signals. An onboard Near Field Communication (NFC) antenna 332 or other communication devices (e.g., a Bluetooth antenna) that use wireless transmission of electromagnetic signaling may cause or generate EMI. The generated EMI may potential generate unwanted electromagnetic noise that may potentially cause a false recording of timestamp data and hence, the generated EMI is filtered by the second signal processing filter 402. Accordingly, second signal processing filter 402 is for protection against EMI, which may also cause a potential false reading and recording of time/date.

First and second EMI filters 392 and 394 are comprised of a series connected capacitor-inductor combinations. First EMI filter 392 is associated with first electrode 158 (via pin 168) and second EMI filter 394 is associated with second electrode 178 (via pin 170).

A first end 198 of first electrode 158 is associated (via pin 168) with GND via a Zener diode 404, first EMI filter 392, a current limiter 450, and active mode signal generator 396. A first end 200 of second electrode 178 is associated (via pin 170) with power source Vcc via a second EMI filter 394, and current limiter R4.

Active mode signal generator 396 is a switch (e.g., a MOSFET). Once electrodes are bridged together by fluid (e.g., a conductive fluid such as blood), the current generated within electrodes 158 and 178 drives MOSFET 396 to ON, generating a "HIGH" on MCU main signal input terminal 406. The generated HIGH at MCU main signal input terminal 406 activates MCU 156 from non-active mode to active mode, which in turn, enables MCU 156 to commence processing of timestamp data.

The addition of MOSFET 396 in this non-limiting, exemplary embodiment shown in FIG. 16A allows bypassing of internal ADC functionality of MCU 156, which saves in power usage. Accordingly, with the use of MOSFET 396, MCU 156 may be programmed to simply accept a "HIGH" voltage value at MCU main signal input terminal 406, and commence processing timestamp data. Therefore, the internal ADC functionality for converting analog signal to digital will not be used, which would substantially extend battery life. Current through electrodes 158 and 178 drives MOSFET 396 to ON, which in turn, places a "HIGH" voltage on MCU main signal input terminal 406. The "HIGH" received at MCU main signal input terminal 406 triggers MCU 156 to active mode and commence actual processing (e.g., generation) of timestamp data without the need or requirement for an analog to digital data conversion.

In this non-limiting, exemplary embodiment illustrated in FIG. 16A, the output device used is a well known, conventional Dynamic Near Field Communication (NFC) 296 that includes an internal EEPROM, with DNFC also functioning as energy harvester in a well known conventional manner.

DNFC includes a Field Detect (FD) output terminal 410 that is associated with input terminal 412 of MCU 156. That is, the illustrated ADC1 I/O is reconfigured as an FD input in the software. FD output terminal 410 of DNFC outputs a HIGH on input terminal 412 of MCU 156 when fluid sampling device 100b is positioned within an interrogation zone of a conventional NFC reader (not shown). This enables MCU 156 to instruct DNFC 296 to actual transmit timestamp data to an NFC reader. MCU 156 retrieves date/time from RTC 226, and writes timestamp information on NFC EEPROM via well known serial clock (SCL) and serial data (SDA) connectivity between RTC 226, MCU 156, and DNFC 296 as illustrated in detail in FIG. 16A.

In this non-limiting, exemplary embodiment shown in FIG. 16A, timestamp data is sourced from and generated by RTC 226, independent of internal clocking signals of MCU 156. Use of external clocking (such as RTC 226), enables programming of MCU 156 to remain in non-active mode until MOSFET switch 396 is driven to ON to enable MCU 156 to switch to an active mode. This scheme substantially reduces power usage and hence, extending battery life, and eliminate the need fro a power pull-tab as in previous embodiments. It should be noted that in this non-limiting, exemplar embodiment shown in FIG. 16A, only a single power source 154 is used for all components that require power, including RTC 226.

RTC 226 continuously remains active (or ON), keeping track of time using power source 154. RTC 226 uses substantially less power than MCU 156, with RTC 226 using only fraction of power used by MCU 156. For example, RTC 226 may potentially draw only about 450 nanoamps of current from power source 154. This conservation of power extends the shelf life of fluid sampling device 100b by a number of years whereas the use of internal clock of MCU 156 would place a very large drain on power consumption, substantially reducing shelf-life.

In this non-limiting, exemplary embodiment shown in FIG. 16A, power circuit 154 may include a voltage and current protection circuitry comprised of a Zener diode and a bypass capacitor as shown to provide clean power in a well known conventional manner. Additionally, a conventional voltage regulator 398 is also provided in this non-limiting, exemplary embodiment, which regulates the voltage range supplied to MCU 156 for proper operation of MCU 156 in a well-known manner.

As best illustrated in the flow chart diagram of FIG. 16B, MCU 156 at operation 414 is in idle mode, waiting for receipt of an interrupt signal at operation 416. At operation 416 MCU 156 determines if an interrupt signal is received in one of its input terminals.

If MCU 156 determines that an interrupt signal is received at one of its input terminals at operation 416, MCU 156 at operation 418 is switched from idle mode to active mode of operation. MCU 156 at operation 420 determines if interrupt signal is from active mode signal generator (or MOSFET) 396.

If MCU 156 determines that the interrupt signal is from active mode signal generator (or MOSFET) 396 (at MCU 156 input terminal 406), at operation 422 MCU 156 reads date/time from RTC 226 (via SCL/SDA lines), and activates DNFC 296 at operation 424. At operation 426 MCU 156 write data/time on DNFC 296 EEPOM, and at operation 428 MCU 156 determines proper storage of data in the EEPROM. If MCU 156 determines that the data is properly stored, MCU 156 reverts to idle mode at operation 414.

If at operation 420 MCU 156 determines that the interrupt signal is not from MOSFET 396, MCU 156 determines if interrupt signal is a Field Detect (FD) signal at its input terminal 412 at operation 430. If at operation 430 MCU 156 determines that the interrupt signal is a Field Detect (FD) interrupt at its input terminal 412, MCU 156 activates DNFC at operation 432, and instructs DNFC 296 to transmit date/time data to an NFC reader at operation 434. For example, fluid sampling device 100*b* may have been brought within the interrogation zone of an NFC reader. At operation 436 MCU 156 determines proper transmission of data. If MCU 156 determines that the data is properly transmitted, MCU 156 powers down. It should be noted that if an interrupt signal is received that is not recognized by MCU 156 (for example at end of operation 430), MCU 156 returns to idle mode at operation 414.

FIGS. 17A to 17I are non-limiting, exemplary illustrations of a fluid sampling device in accordance with another embodiment of the present invention. The fluid sampling device 100*c* illustrated in FIGS. 17A to 17I includes similar corresponding or equivalent components, interconnections, functional, operational, and or cooperative relationships as the devices 100*a* and 100*b* that are shown in FIGS. 1A to 16B, and described above. Therefore, for the sake of brevity, clarity, convenience, and to avoid duplication, the general description of FIGS. 17A to 17I will not repeat every corresponding or equivalent component, interconnections, functional, operational, and or cooperative relationships that has already been described above in relation to devices 100*a* and 100*b* that are shown in FIGS. 1A to 16B but instead, are incorporated by reference herein.

In this non-limiting, exemplary embodiment, electrodes 158 and 170 are no longer directly, mechanically in contact with absorbent member 116 and hence, eliminating concerns regarding potential leaching from electrodes to absorbent member 116. Instead, as detailed below, a non-leaching medium 442 is used to provide an electrical continuity between electrodes 158, 170, and absorbent member 116 when absorbent member 116 is loaded with fluid. Further, since leaching is no longer an issue, all handler probes 110*c* may optionally be associated with recorder 114*f* as detailed below.

Figure 17A:
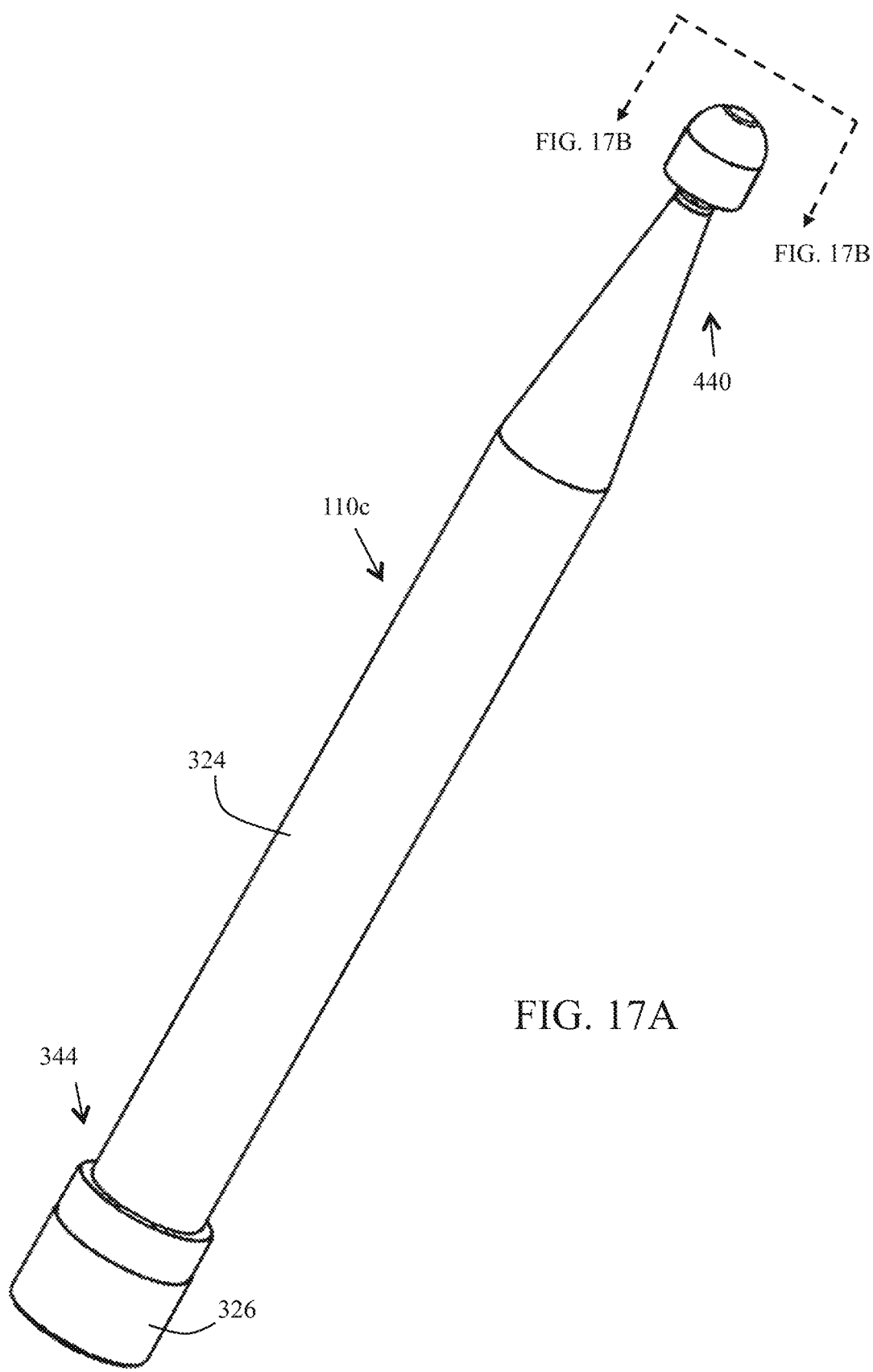
Figure 17C:
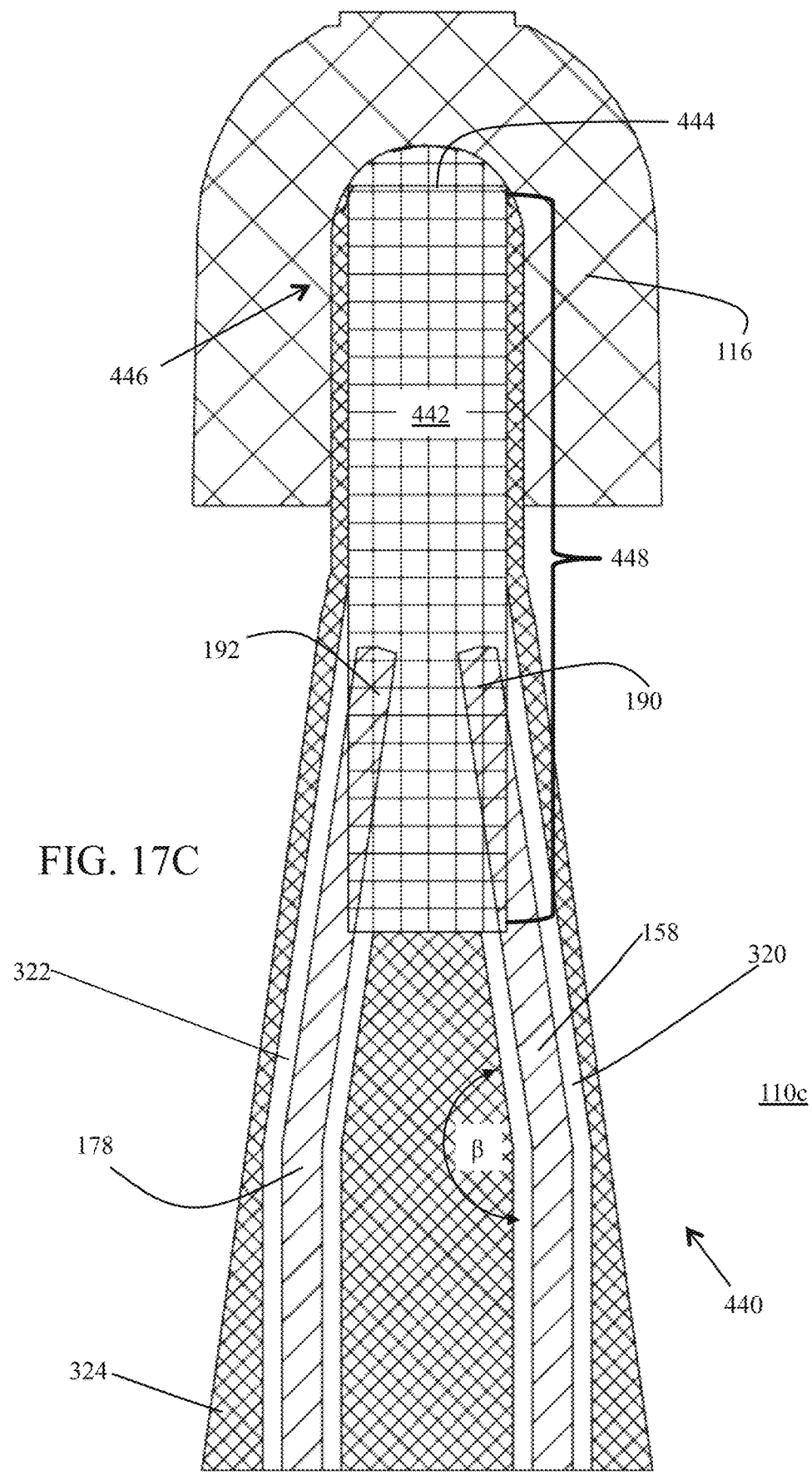

FIGS. 17A to 17C are non-limiting, exemplary illustrations of a handler probe in accordance with one or more embodiments of the present invention. As illustrated, handler probe 110*c* is comprised of a first end 440 that accommodates absorbent member 116 and second end 344 that is identical to the second end of handler probes 110*b* of fluid sampling device 100*b*.

As best illustrated in FIG. 17C, first end 440 of main 324 of handler probe 110*c* includes top opening 444 at top distal end 446, and a cavity 448, for insertion and housing of a cylindrically shaped medium 442. Absorbent member 116 caps over top opening 444 in full contact with medium 442, and securely mounted onto handler probe 110*c*.

In this non-limiting, exemplary embodiments, orifices 320 and 322 no longer include lateral openings 334 and 336 but instead are oriented (bent) inward at an angle β towards cavity 448, with distal ends 190 and 192 of inserted electrodes 158 and 178 in full contact with medium 442. Non-limiting, non-exhaustive listing of examples of medium 442 that may be used may include any one or more of Polyolefin, Polyethylene (PE), Polyethylene terephthalate (PET), Polypropylene, Cellulose, Nylon, glass fiber, hydrophilic material, etc.

As with previously disclosed embodiments above, users may simply dip absorbent member 116 of any handler probe 110*c* into fluid sample source 118 to sample fluid. Wicked fluid loaded on absorbent member 116 would continue to be wicked by medium 442. Since medium 442 is in full contact with distal ends 190 and 192 of electrodes 158 and 178, the fluid therein would bridge gap between electrodes 158 and 178 and create an electrical "closed-circuit" condition to trigger a reading of timestamp.

Figure 10A:
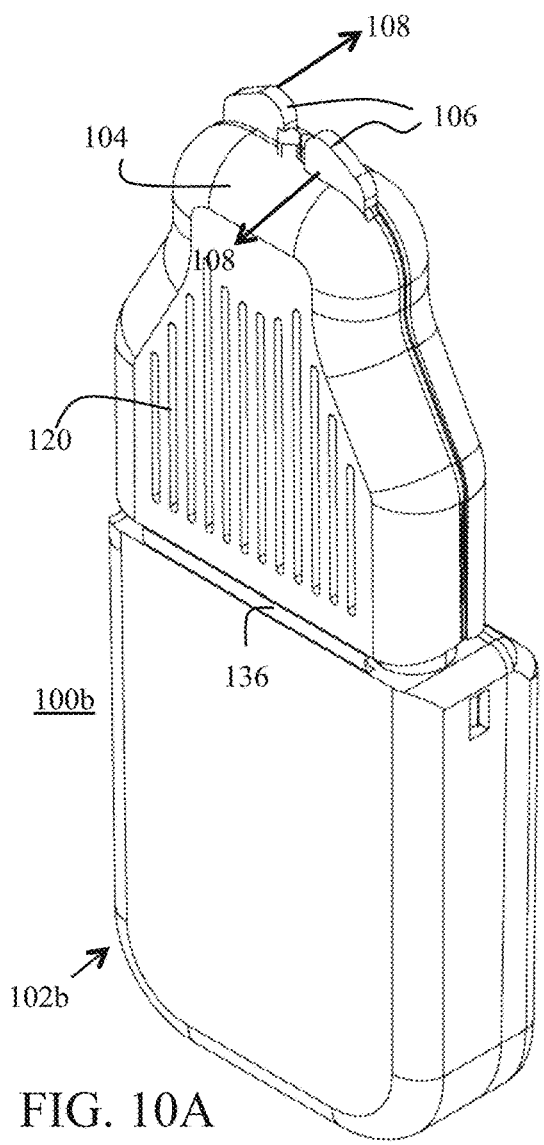
FIGS. 10A to 16B are non-limiting, exemplary illustrations of a fluid sampling device in accordance with another embodiment of the present invention.
Figure 10B:
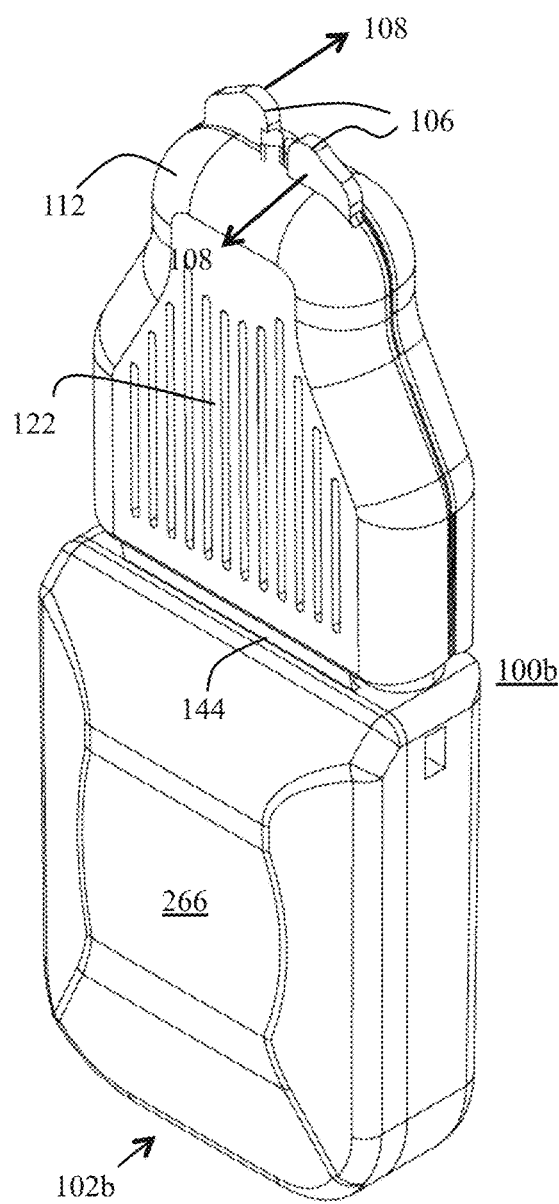
Figure 11A:
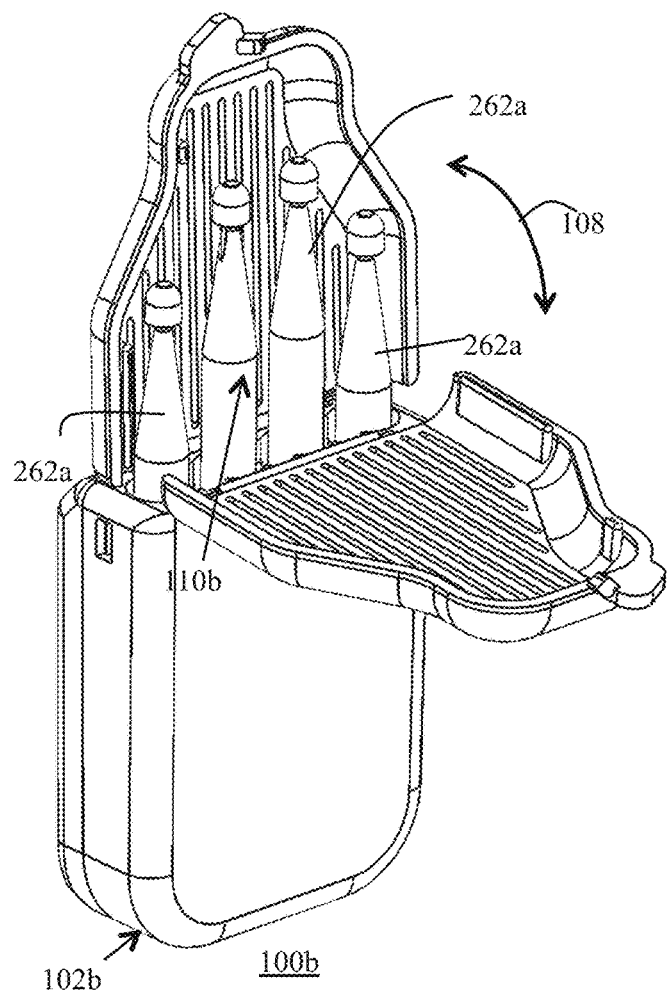
Figure 11B:
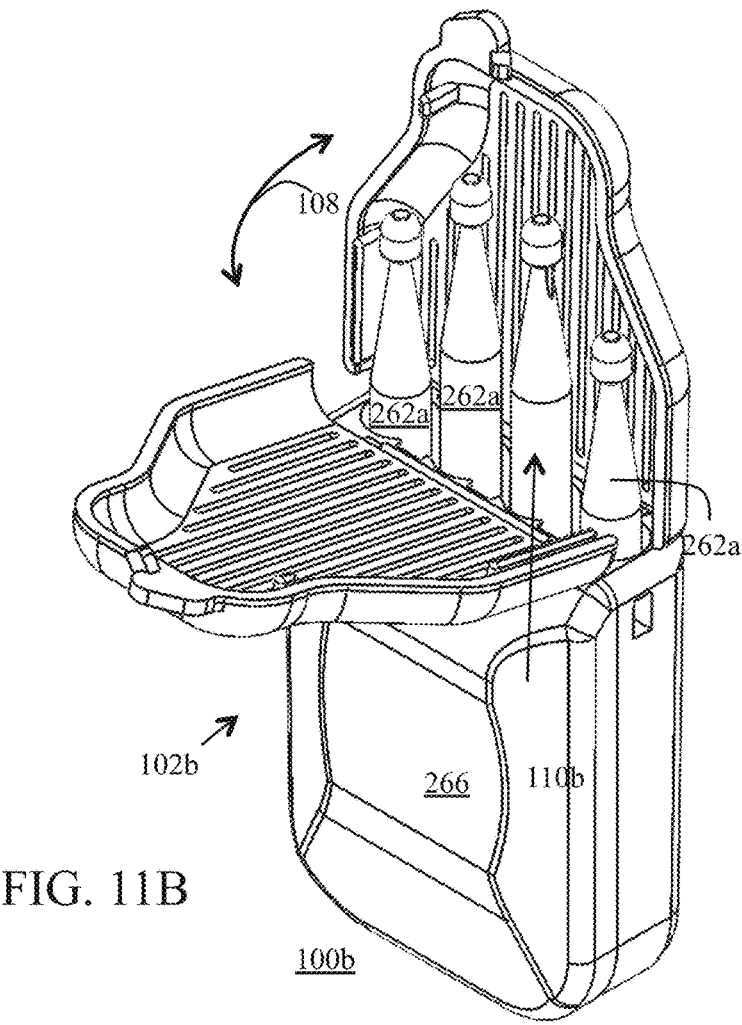
Figure 11C:
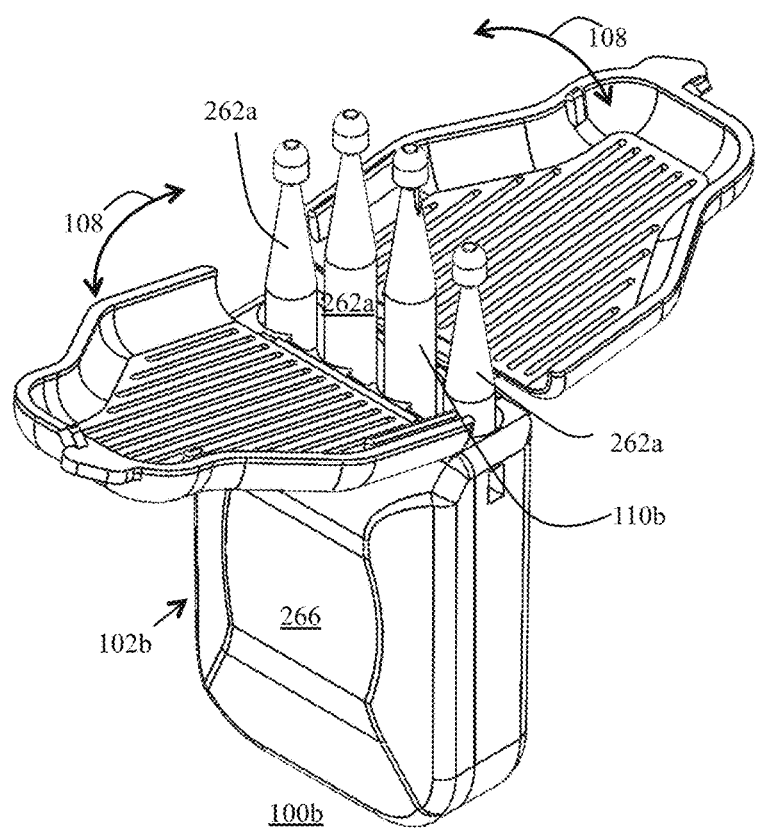
Figure 11D:
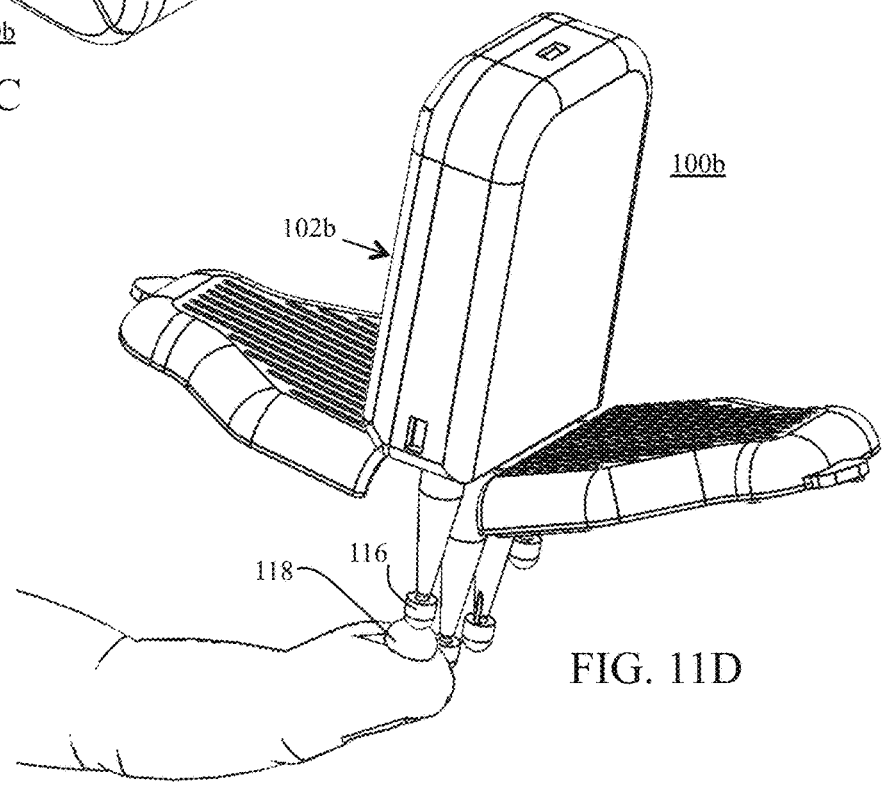
Figure 17E:
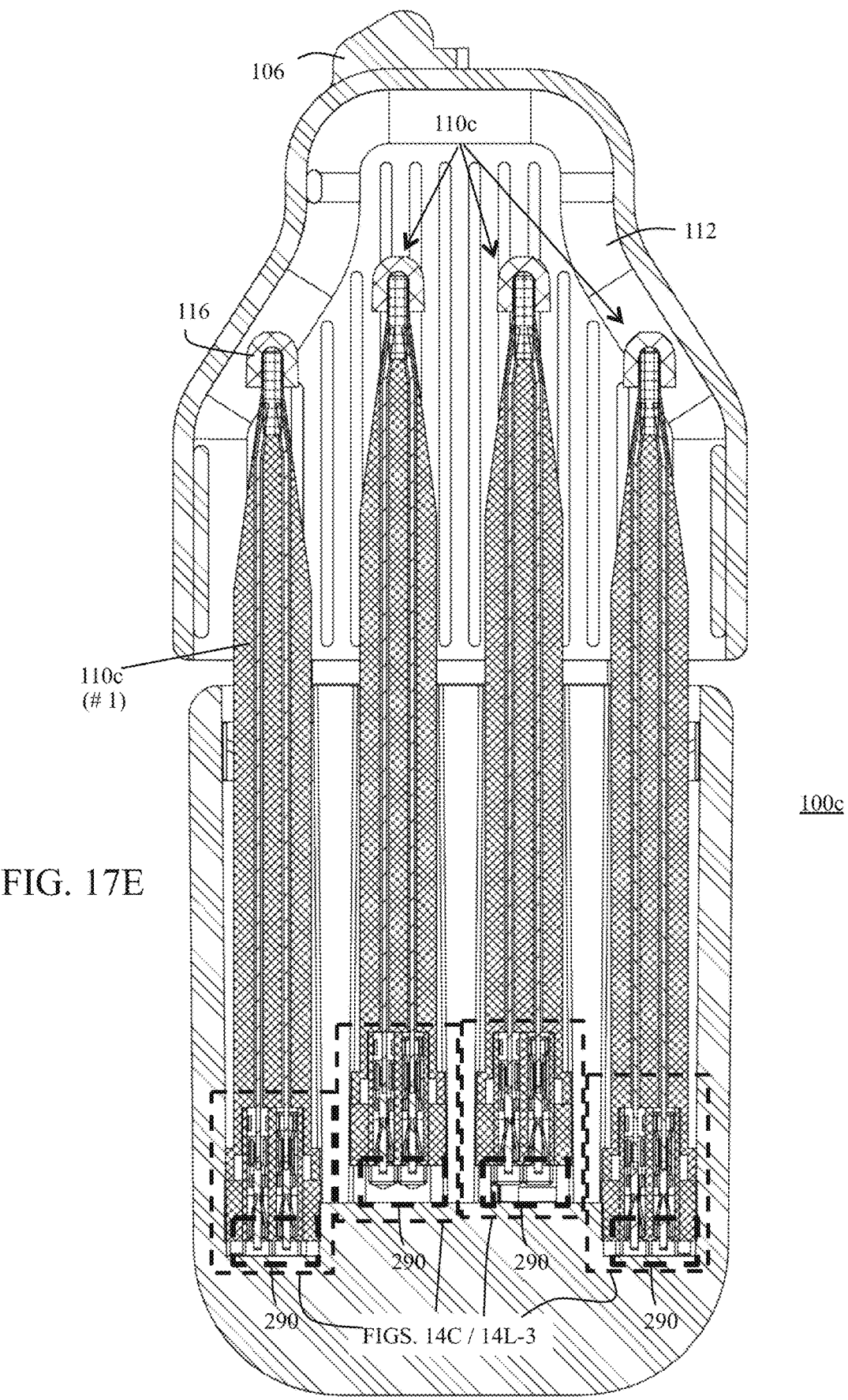

FIG. 17D illustrates fully assembled handler probes 110*c* in relation to housing 264, including a sectional view thereof in FIG. 17E in accordance with one or more embodiments of the present invention. As indicated above, since leaching is no longer an issue, all handler probes 110*c* may optionally be associated with recorder 114*f* and hence, all handler probes 110*c* include connectivity with recorder 114*f* as best shown in FIGS. 10A and 17I.

In this embodiment, side 278 of housing 264 may comprise of a plurality of openings 290 (FIG. 17E) or a single larger opening that enable access to recorder 114*f* (and hence, interior side 276). Openings 290 or one larger opening would allow a plurality of paired pins 168 and 170 from recorder 114*f* (on a PCB) extend out through openings 290 or one larger opening, with each pair of pins 168 and 170 connecting with their respective handler probes 110*c*. Accordingly, since four handler probes 110*c* are used in this non-limiting, exemplary instance, there may be up to four pairs of pins 168 and 170, with each pair 168, 170 connecting to one respective handler probe 110*c* through openings 290 on side 278.

Figure 17G:
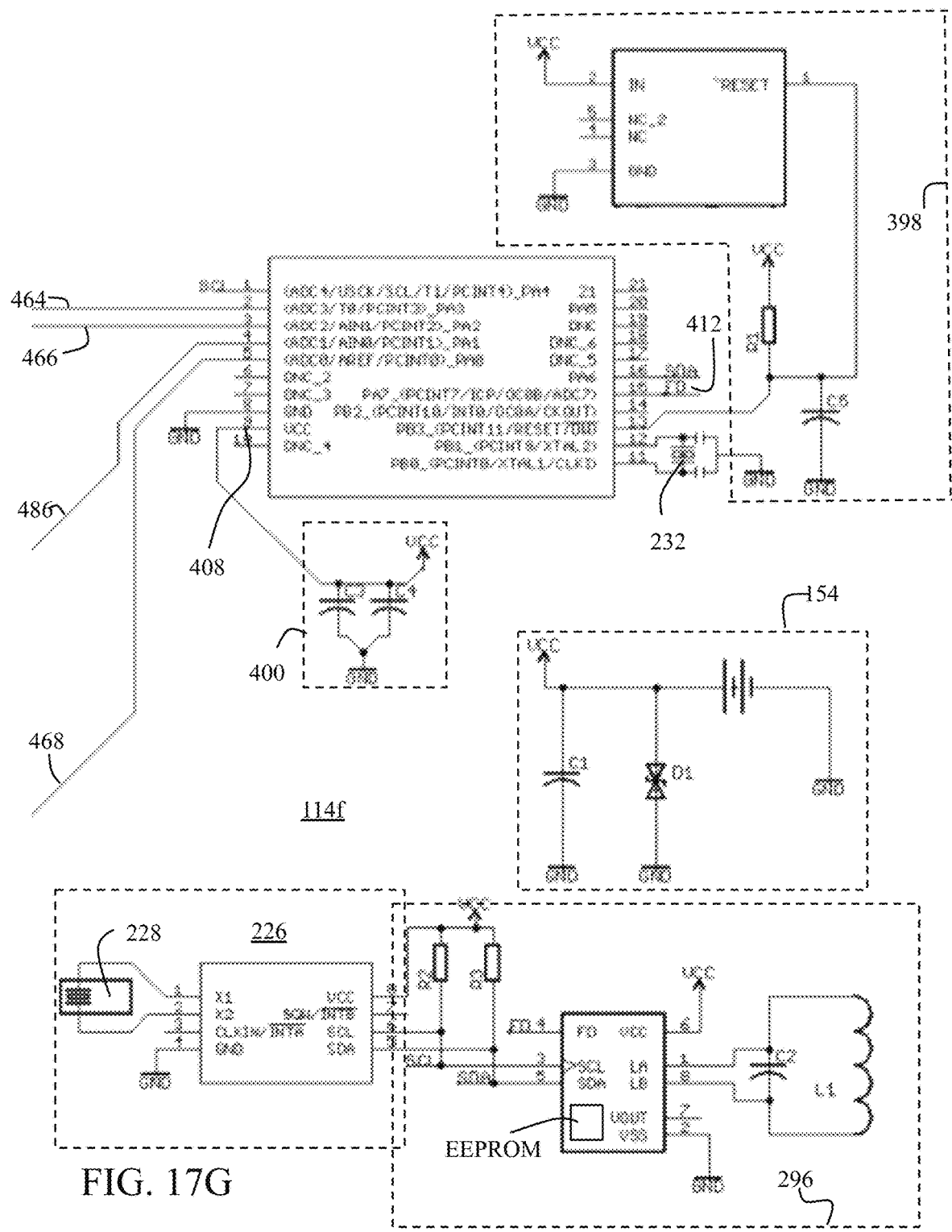
Figure 17H:
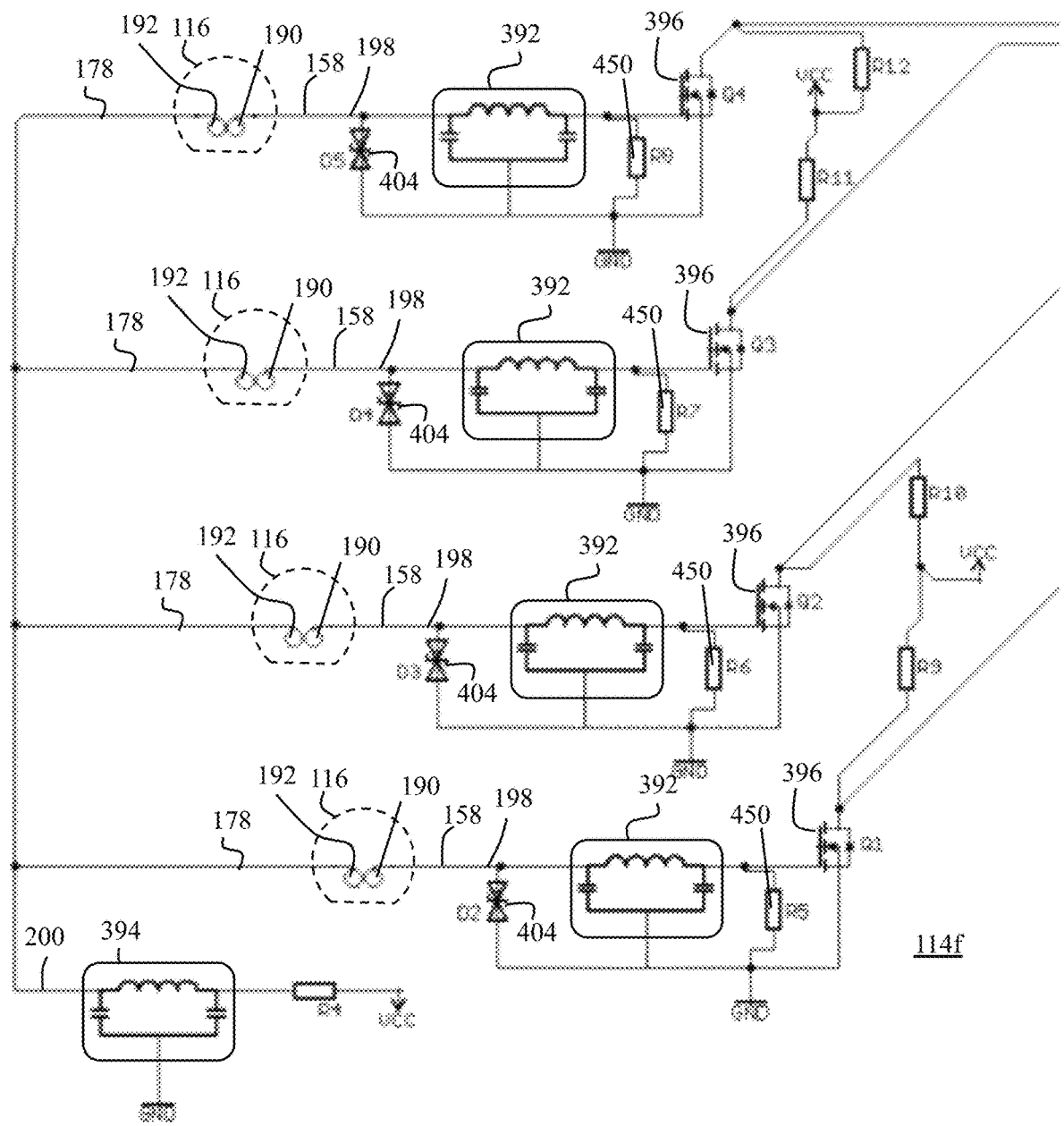
Figure 17I:
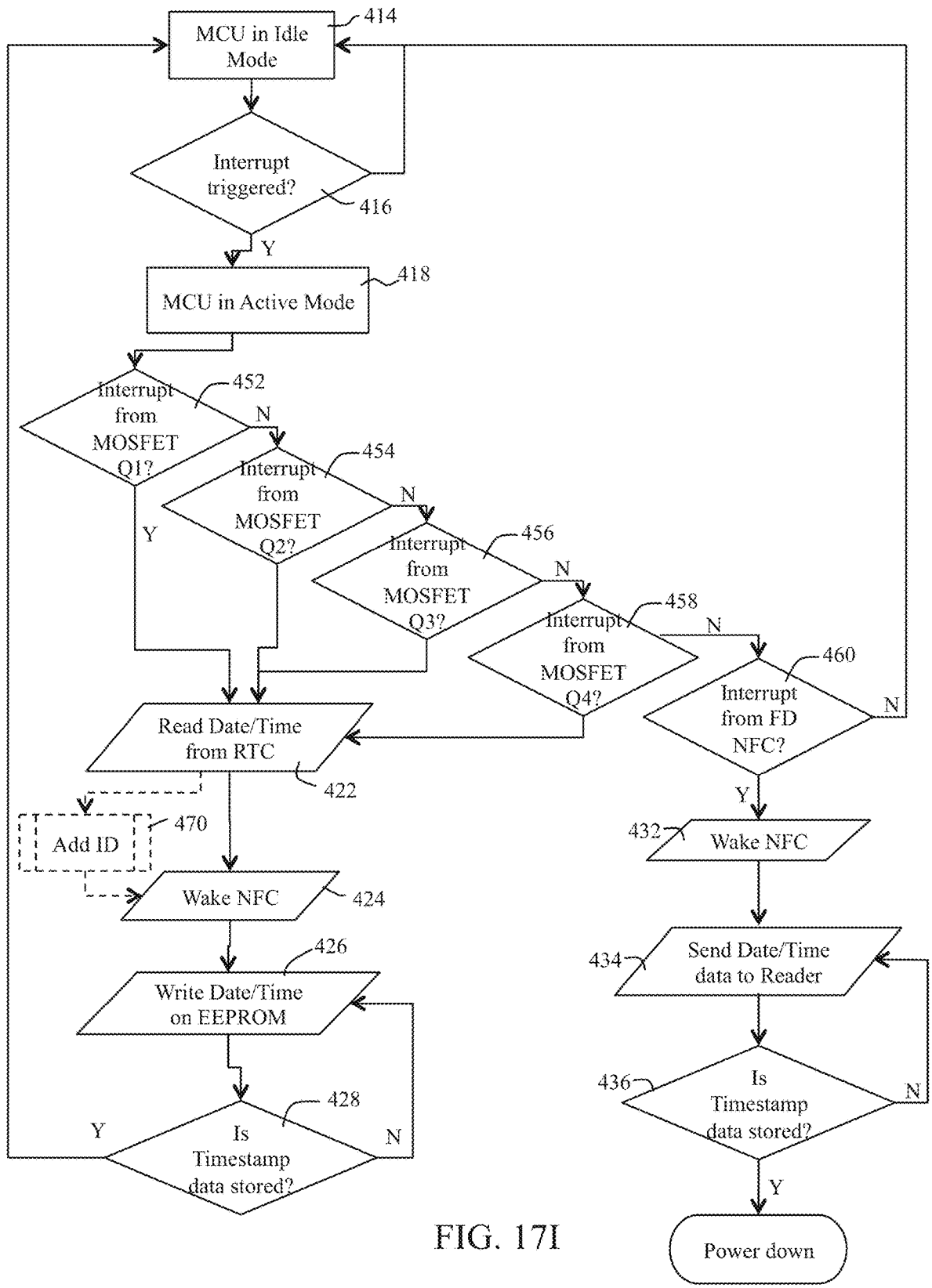

FIG. 17F to 17H are non-limiting, exemplary illustration of an electrical schematic circuit diagram of handler probes 110*c* and recorder 114*f* combination shown in FIGS. 17A to 17E in accordance with one or more embodiments of the present invention. FIG. 17I is a non-limiting, exemplary illustration of a flow diagram related to microcontroller unit (MCU) operations shown in FIGS. 17F to 17H in generating and saving of recorded data (e.g., timestamp data) in accordance with one or more embodiments of the present invention.

As illustrated in FIG. 17F to 17H, fluid sampling device 100*c* includes a plurality of handler probe 110*c* with absorbent member 116. In this non-limiting, exemplary instance there are four handler probes 110*c*. The schematic circuit diagram illustrated in FIGS. 17F to 17H is substantially identical to that shown in FIG. 16A with the exception that instead of having a single handler probe 110*b* with its single set of EMI filters 392, 394, and its connection with a single MOSFET 396, etc., there are now multiple duplicates of such connectivity provided as detailed below.

In this non-limiting, embodiment there are four pairs of electrodes 158 and 178, with each pair associated with one handler probe 110*c* and recorder device 114*f* In this non-limiting, exemplary embodiment four active mode signal generators 396 are used to output four separate active mode signals to MCU 156 when a pair of electrode 158 and 178 for a particular handler probe 110*c* are bridged by a conductive fluid such as blood. Microcontroller unit (MCU) 156 is driven from a non-active mode (e.g., idle) to an active mode by any one of the pluralities of active mode signals generated by any one of the plurality of active mode signal generators 396 or DNFC 296.

As further illustrated in FIG. 17F to 17H, in this non-limiting exemplary embodiment, recorder 114*f* includes a plurality of second signal processing circuitry. Second signal processing circuitry includes a plurality of identical Electromagnetic (EMI) Interference filters 392, and a single Electromagnetic (EMI) Interference filter 394 (also identical to EMI filters 392).

In this embodiment, MCU 156 input terminals 464 is connected to MOSFET Q4, MCU 156 input terminal 466 is connected to MOSFET Q3, MCU 156 input terminal 486 is connected to MOSFET Q2, and MCU 156 input terminal 468 is connected to MOSFET Q1.

As illustrated in the flow chart diagram of FIG. 17I, MCU 156 at operation 416 determines if an interrupt signal is received in one of its input terminals. If MCU 156 determines that an interrupt signal is received at one of its input terminals at operation 416, MCU 156 at operation 418 is switched from idle mode to active mode of operation. MCU 156 at operations 452 to 460 determines if the interrupt signal is from one of the many active mode signal generators (or MOSFET) 396 at one of its input terminals 464, 466, 486, 468, or DNFC 296 at input terminal 412.

If MCU 156 determines that the interrupt signal is from any one of the plurality of active mode signal generators (or MOSFETs Q1 to Q4) 396, at operation 422 MCU 156 reads date/time from RTC 226 (via SCL/SDA lines), and activates DNFC 296 at operation 424. At operation 426 MCU 156 writes data/time on DNFC 296 EEPOM, optionally associating the timestamp with the particular handler probe 110c that triggered the timestamp, and at operation 428 MCU 156 determines proper storage of data in the EEPROM. If MCU 156 determines that the data is properly stored, MCU 156 reverts to idle mode at operation 414. Accordingly, in this embodiment, there would be four stored timestamp data, with each optionally associated with one of the four handler probes 110c. The four timestamp data may be used to determine the duration from earliest time (e.g., 4 July 2016 13:00:00) when the first absorbent member 116 triggered the timestamp to the final time (e.g., 4 July 2016 13:01:30) when the last or fourth absorbent member 116 triggered the timestamp.

Alternatively, the four handler probes 110c associated with their respective MOSFETs Q1 to Q4 may optionally include identifications that associate a particularly generated timestamp with a specific, corresponding absorbent member 116 that triggered that timestamp. For example, handler probe 110c at position #1 (FIG. 17E) may be associated with MOSFET Q4, which may be hardwired to MCU 156 input terminal 464. In this case, handler probe 110c and its absorbent member 116 at position #1 may be identified with ID=1, with generated timestamp that includes ID=1 as part of the timestamp data, and stored in the DNFC 296 EEPROM. Therefore, referring back to FIG. 17I, optionally, at optional operation 470 MCU 156 may add an ID to the read timestamp data prior to write operation 426. For example, since handler probe 110c at position 1 is connected to terminal 464, MCU would add ID=1 to timestamp data at operation 470 as a result of executing operation 458 (since MOSFET Q4 is associated with handler probe 110c at position #1 and MCU 156 terminal 464), after timestamp data is read at operation 422.

If MCU 156 determines that the interrupt signal is not from any one of the MOSFETs 396, MCU 156 determines if interrupt signal is a Field Detect (FD) signal at its input terminal 412 at operation 460. If at operation 460 MCU 156 determines that the interrupt signal is a Field Detect (FD) interrupt at its input terminal 412, MCU 156 activates DNFC at operation 432, and instructs DNFC 296 to transmit all four date/time data to an NFC reader at operation 434.

At operation 436 MCU 156 determines proper transmission of all four timestamp data. If MCU 156 determines that the data is properly transmitted, MCU 156 powers down. It should be noted that if an interrupt signal is received that is not recognized by MCU 156 (for example at end of operation 460), MCU 156 returns to idle mode at operation 414.

Figure 18A:
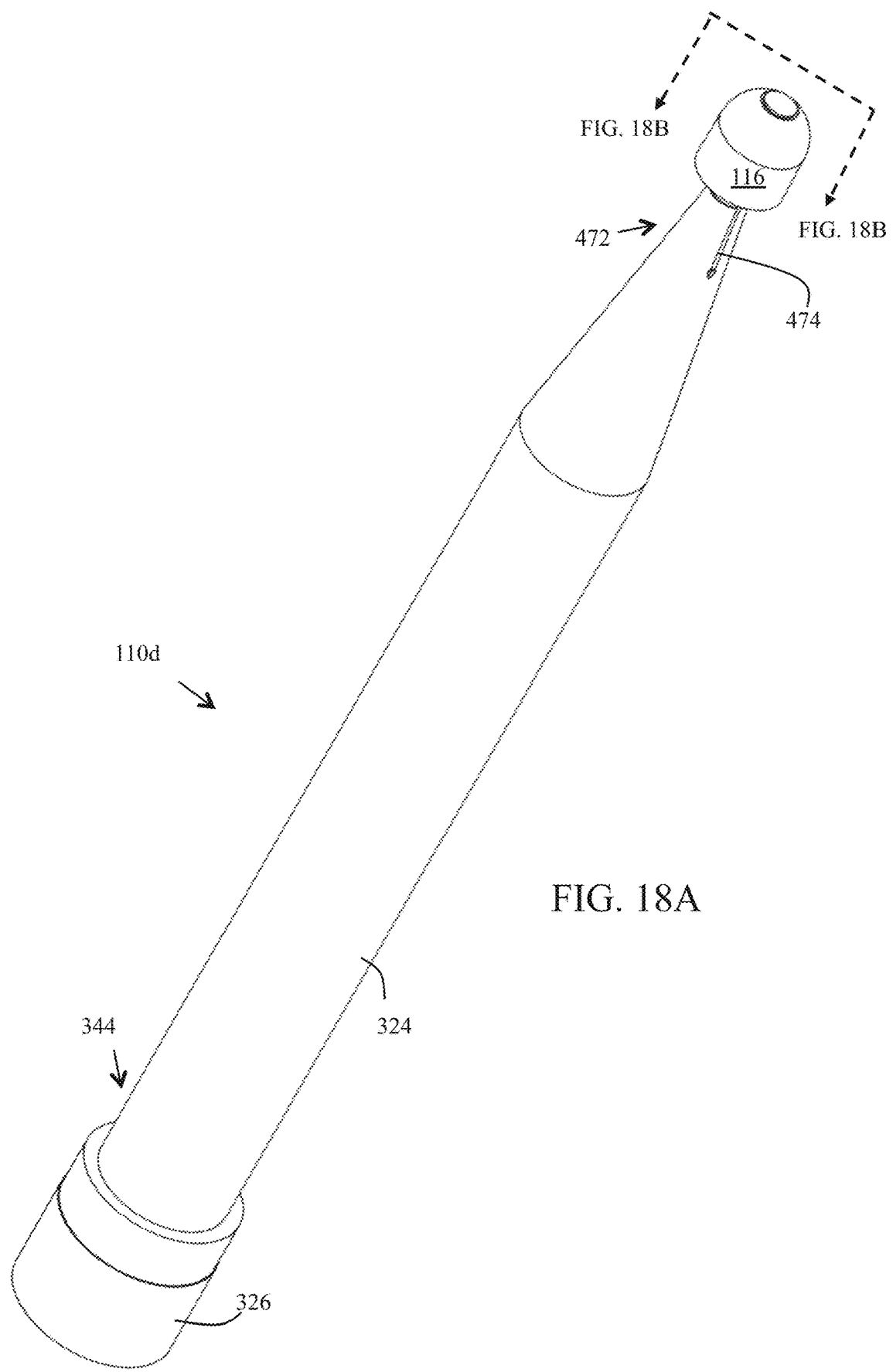
Figure 18C:
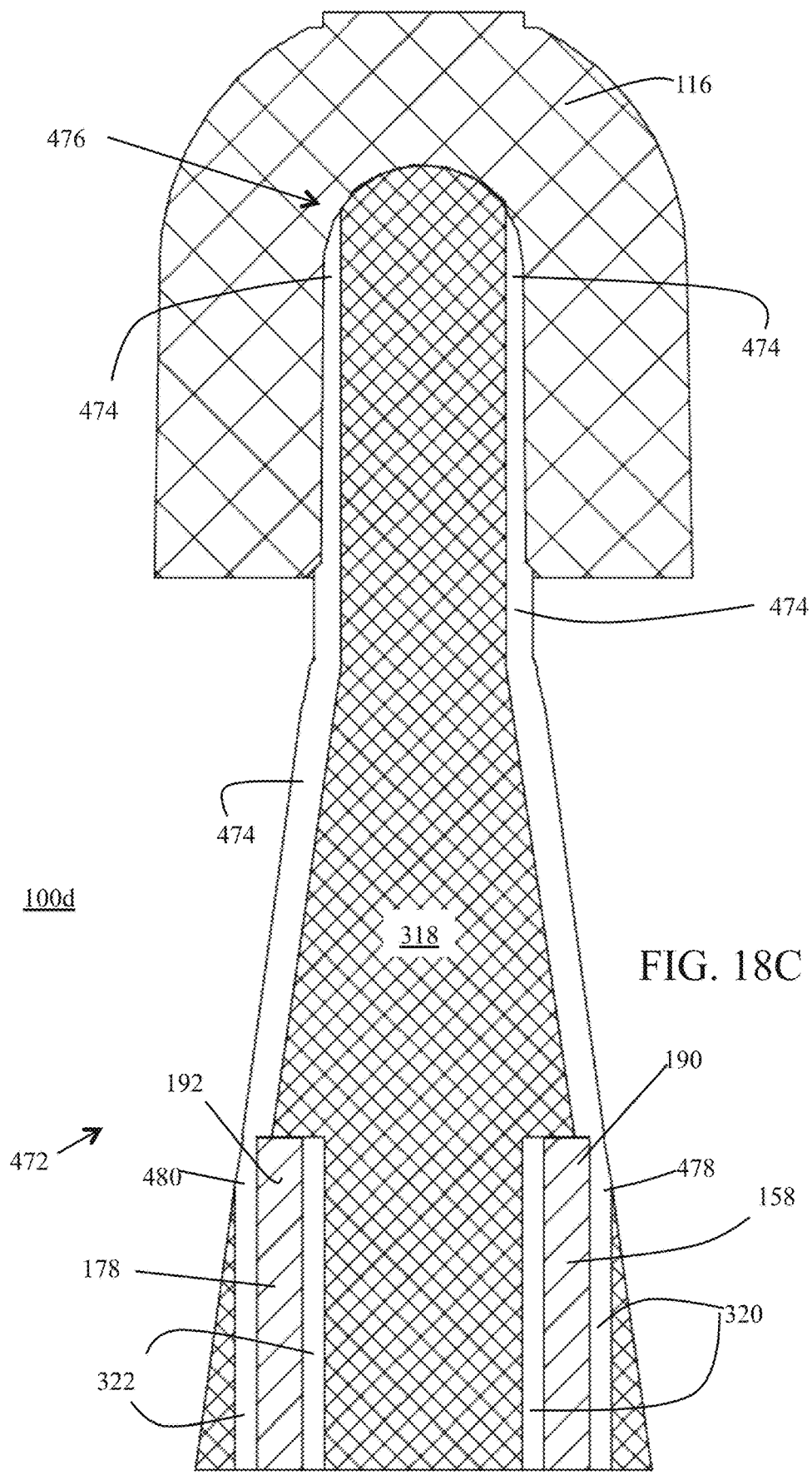

FIGS. 18A to 18C are non-limiting, exemplary illustrations of handler probe in accordance with another embodiment of the present invention. Handler probe 110d illustrated in FIGS. 18A to 18C includes similar corresponding or equivalent components, interconnections, functional, operational, and or cooperative relationships as handler probes 110a to 110c that are shown in FIGS. 1A to 17I, and described above. Therefore, for the sake of brevity, clarity, convenience, and to avoid duplication, the general description of FIGS. 18A to 18C will not repeat every corresponding or equivalent component, interconnections, functional, operational, and or cooperative relationships that has already been described above in relation to handler probes 110a to 110c that are shown in FIGS. 1A to 17I but instead, are incorporated by reference herein.

As illustrated, handler probe 110d in FIGS. 18A to 18C is comprised of a first end 472 that accommodates absorbent member 116 and second end 344 that is identical to the second ends of handler probes 110b and 110c of fluid sampling devices 100b and 100c. As detailed below, in this non-limiting, exemplary embodiment, instead of using a medium 442, the exterior of first end 472 is provided with well-known open micro-fluidic channels 474 that enable fluid to be moved from absorbent member 116 to electrodes 158 and 178 via capillary action and hence, eliminating potential leaching problems but without the use of an additional medium 442.

As best illustrated in FIG. 18C, exterior of first end 472 of main 324 of handler probe 110d is comprised of open micro-fluidic channels 474 that extend from tip 476 of main 324 to lateral opening 478 and 480 of orifices 320 and 322. Absorbent member 116 caps over tip 476 covering over and in full contact with open micro-fluidic channels 474, and securely mounted onto handler probe 110d. In this non-limiting, exemplary embodiment, electrodes 158 and 178 do not extend out of lateral openings 478 and 480 of orifices 320 and 322.

As with previously disclosed embodiments above, users may simply dip absorbent member 116 of any handler probe 110d into fluid sample source 118 to sample fluid. Wicked fluid loaded on absorbent member 116 would continue to be moved by capillary action through open micro-fluidic channels 474, leading to electrodes 158 and 178. Fluid in absorbent member 116, open micro-fluidic channels 474, and orifices 320 and 322 contacting distal ends 190 and 192 of electrodes 158 and 178 would bridge gap between electrodes 158 and 178 and create an electrical "closed-circuit" condition to trigger a reading of timestamp. As with handler probe 110c, since leaching is also no longer an issue with handler probe 110d, all handler probes 110d may optionally be associated with recorder 114f and hence, all handler probes 110d may include connectivity with recorder 114f.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Further, the specification is not confined to the disclosed embodiments. Therefore, while exemplary illustrative embodiments of the invention have been described, numerous variations and alternative embodiments will occur to those skilled in the art. For example, all input terminals of all of the illustrated microcontroller units may be reconfigured in software in well-known manner. As another example, it is only for convenience of example and discussion purposes that throughout the disclosure liquid source or fluid sample is indicated from a finger prick of a human. It will be quickly apparent that any one of the one or more embodiments disclosed may use fluid sample from other sources such as urine, saliva, including those from animals. Additionally, fluid sample may in fact be from other conductive fluid sources such as water, or other conductive fluids or liquid chemicals. In fact, any one of the one or more embodiments disclosed may easily be use in other non-medical, but industrial applications such as sampling a water source, conductive liquid chemicals, etc. As importantly, different types of absorbent members of different materials or composition may be used that may be best suited for the specific type of conductive fluid source being sampled. For example, a particular absorbent member of a certain material or composition may be better suited for sampling a specific type of conductive chemical liquid. The shape of the absorbent member may also be varied. Such variations and alternate embodiments are contemplated, and can be made without departing from the spirit and scope of the invention.

It should further be noted that throughout the entire disclosure, the labels such as left, right, front, back, top, inside, outside, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction, orientation, or position. Instead, they are used to reflect relative locations/positions and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

Further the terms "a" and "an" throughout the disclosure (and in particular, claims) do not denote a limitation of quantity, but rather denote the presence of at least one of the referenced item.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of in the claims herein is not intended to invoke the provisions of 35 U.S.C. 112, Paragraph 6.

What is claimed is:

1. A fluid sampling device, comprising:
   an absorbent member that directly absorbs a fluid unmediated and unaltered from a source of the fluid; and
   an onboard recorder that is triggered to generate data when the fluid is absorbed by the absorbent member;
   the data includes time and date of sample acquisition.

2. A fluid sampling device, comprising:
   an absorbent member that directly absorbs a fluid unmediated and unprocessed from a source of the fluid; and
   an onboard recorder that automatically identifies a time and a date of the fluid absorbed by the absorbent member at a time at which the fluid is absorbed.

3. A fluid sampling device, comprising:
   an absorbent member that directly absorbs a fluid unmediated and without alternation from a source of the fluid; and
   an onboard recorder associated with the absorbent member;
   wherein: the recorder is automatically triggered to generate data in relation to fluid absorbed by the absorbent member at a time at which the fluid is absorbed.

4. The fluid sampling device as set forth in claim 3, wherein:
   the generated data includes timestamp data, which includes actual time and date of the fluid absorbed by the absorbent member.

* * * * *